(12) United States Patent
Phallen et al.

(10) Patent No.: US 6,213,739 B1
(45) Date of Patent: Apr. 10, 2001

(54) LINEAR PERISTALTIC PUMP

(75) Inventors: Iver J. Phallen, Youngstown; Douglas N. Vogt, Pavilion, both of NY (US)

(73) Assignee: Niagara Pump Corporation, Buffalo, NY (US)

( * ) Notice: Subject to any disclaimer, the term of this patent is extended or adjusted under 35 U.S.C. 154(b) by 0 days.

(21) Appl. No.: 09/341,443

(22) PCT Filed: Jan. 16, 1998

(86) PCT No.: PCT/US98/00958

§ 371 Date: Jul. 9, 1999

§ 102(e) Date: Jul. 9, 1999

(87) PCT Pub. No.: WO98/31935

PCT Pub. Date: Jul. 23, 1998

Related U.S. Application Data

(60) Provisional application No. 60/036,115, filed on Jan. 17, 1997, and provisional application No. 60/040,232, filed on Mar. 11, 1997.

(51) Int. Cl.$^7$ .............................. F04B 43/08; A61M 1/00
(52) U.S. Cl. ........................ 417/478; 417/474; 604/153
(58) Field of Search ..................................... 417/474, 478, 417/475, 479, 476, 477.1, 477.3, 477.9; 604/153, 151

(56) References Cited

U.S. PATENT DOCUMENTS

| | | |
|---|---|---|
| 1,922,196 | 8/1933 | Butler . |
| 2,105,200 | 1/1938 | Phelps . |
| 2,393,838 | 1/1946 | Tarbox . |
| 2,412,397 | 12/1946 | Harper . |
| 2,926,614 | 3/1960 | Rose . |
| 2,971,471 | 2/1961 | Huebschman . |
| 3,046,903 | 7/1962 | Jones . |
| 3,048,121 | 8/1962 | Sheesley . |
| 3,154,021 | 10/1964 | Vick . |
| 3,158,104 | 11/1964 | Hutchinson . |
| 3,263,617 | 8/1966 | Johnson . |

(List continued on next page.)

FOREIGN PATENT DOCUMENTS

| | | |
|---|---|---|
| 74594/74 | 10/1974 | (AU) . |
| 32368/89 | 10/1989 | (AU) . |
| 1426963 | 3/1976 | (GB) . |
| 2020735 | 11/1979 | (GB) . |
| 2057067 | 3/1981 | (GB) . |
| 2257478 | 1/1993 | (GB) . |
| 92/16450 A1 | 10/1992 | (WO) . |
| 94/21918 A1 | 9/1994 | (WO) . |

*Primary Examiner*—Teresa Walberg
*Assistant Examiner*—Thor Campbell
(74) *Attorney, Agent, or Firm*—John C. Thompson

(57) ABSTRACT

A liquid pumping apparatus for pumping liquids, more specifically a linear peristaltic pump apparatus. The apparatus consists of a high durometer compressible elastomeric liquid flow tube (12), an infeed valve assembly (26), an outfeed valve assembly (38), an extensible and retractable actuator anvil (34) having a round surface which engages the flow tube (12) at all times, an opposed anvil (24.1) having a round surface in engagement with the flow tube at all times, the flow tube being held between the anvils (34, 24.1) in a slightly compressed state when the anvil (34) is retracted, and a control assembly (100) for causing the movable anvil to be sequentially extended and retracted to cause flow within the flow tube (12) from the infeed valve assembly (26) to the outfeed valve assembly (38). With this apparatus the lumen of the flow tube (12) to the sides of the anvils is not completely reduced to zero volume during displacement compression whereby gas embolisms do not erupt or explode when discharged. Two principal embodiments are disclosed, one having infeed and outfeed check valves which oclude the flow tube, and the other having check valves.

78 Claims, 40 Drawing Sheets

U.S. PATENT DOCUMENTS

| | | |
|---|---|---|
| 3,318,251 | 5/1967 | Smith . |
| 3,349,716 | 10/1967 | Weber . |
| 3,518,033 | 6/1970 | Anderson . |
| 3,724,973 | 4/1973 | Shill . |
| 3,811,800 | 5/1974 | Shill . |
| 3,822,720 | 7/1974 | Souza . |
| 3,829,249 | 8/1974 | Pursley . |
| 3,902,490 | 9/1975 | Jacobsen et al. . |
| 3,983,857 | 10/1976 | O'Connor . |
| 3,998,103 | 12/1976 | Björklund et al. . |
| 4,014,318 | 3/1977 | Dockum . |
| 4,360,324 | 11/1982 | Ohara et al. . |
| 4,410,322 | 10/1983 | Archibald . |
| 4,413,751 | 11/1983 | Tokorozawa . |
| 4,479,797 | 10/1984 | Kobayashi et al. . |
| 4,500,266 | 2/1985 | Cummins . |
| 4,501,405 | 2/1985 | Usry . |
| 4,558,989 | 12/1985 | Chappell . |
| 4,657,490 | 4/1987 | Abbott . |
| 4,722,372 | 2/1988 | Hoffman et al. . |
| 4,789,016 | 12/1988 | Mihail . |
| 4,886,432 | 12/1989 | Kimberlin . |
| 4,893,991 | 1/1990 | Heminway et al. . |
| 4,967,940 | 11/1990 | Blette et al. . |
| 5,011,378 | 4/1991 | Brown et al. . |
| 5,049,047 | 9/1991 | Polaschegg et al. . |
| 5,082,429 | 1/1992 | Soderquist et al. . |
| 5,088,522 | 2/1992 | Rath et al. . |
| 5,131,816 | 7/1992 | Brown et al. . |
| 5,151,019 | 9/1992 | Danby et al. . |
| 5,165,873 | 11/1992 | Meijer . |
| 5,199,852 | 4/1993 | Danby . |
| 5,209,654 | 5/1993 | Nilsson et al. . |
| 5,217,355 | 6/1993 | Hyman et al. . |
| 5,222,980 | 6/1993 | Gealow . |
| 5,242,083 | 9/1993 | Christine et al. . |
| 5,242,279 | 9/1993 | Knuth . |
| 5,252,044 | 10/1993 | Raines et al. . |
| 5,273,406 | 12/1993 | Feygin . |
| 5,290,158 | 3/1994 | Okada . |
| 5,302,093 | 4/1994 | Owens et al. . |
| 5,316,452 | 5/1994 | Bogen et al. . |
| 5,320,503 | 6/1994 | Davis . |
| 5,342,180 | 8/1994 | Daoud . |
| 5,349,825 | 9/1994 | Duke et al. . |
| 5,352,103 | 10/1994 | Auer . |
| 5,364,242 | 11/1994 | Olsen . |
| 5,370,510 | 12/1994 | Sinclair . |
| 5,380,172 | 1/1995 | Ulbing . |
| 5,401,139 | 3/1995 | Nabity et al. . |
| 5,405,252 | 4/1995 | Nikkanen . |
| 5,554,013 | 9/1996 | Owens et al. . |
| 5,556,258 | 9/1996 | Lange et al. . |
| 5,577,891 | 11/1996 | Loughnane et al. . |
| 5,584,667 | 12/1996 | Davis . |
| 5,588,816 | 12/1996 | Abbott et al. . |
| 5,593,290 | 1/1997 | Greisch et al. . |
| 5,964,583 * | 10/1999 | Danby .................................. 417/474 |
| 5,980,490 * | 11/1999 | Tsoukalis ............................ 604/151 |

* cited by examiner

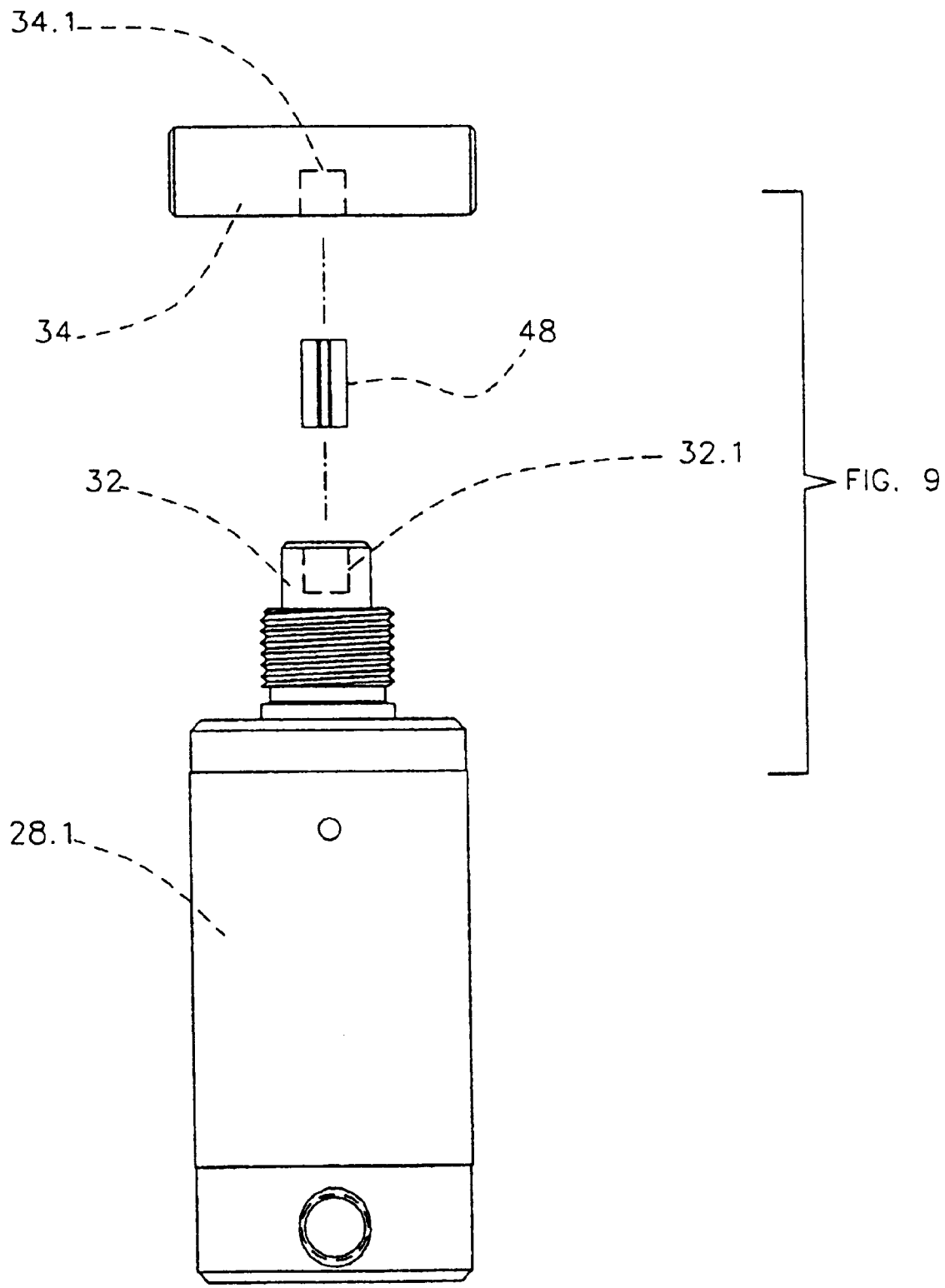

FIG. 10
FIG. 10A
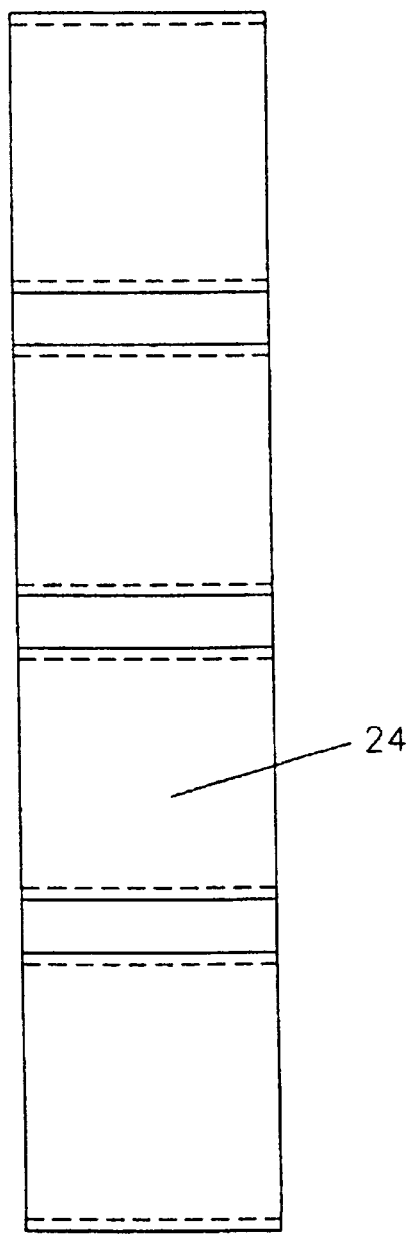
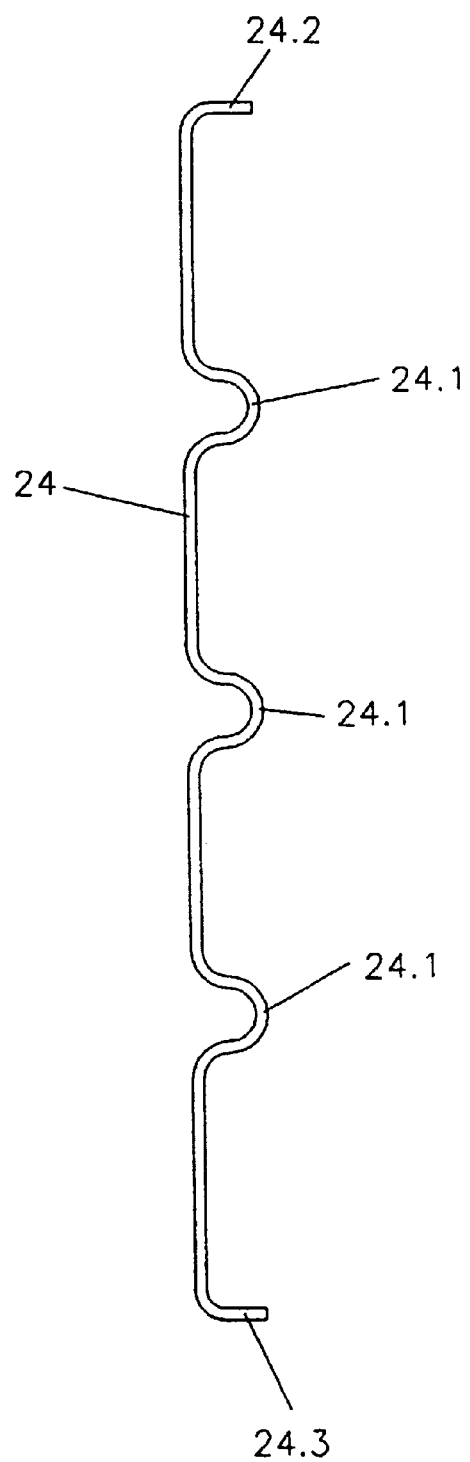

AT REST

CLOSE IFV

OPEN IFV

COMPRESS
DISPLACEMENT
SECTION

CLOSE OFV

OPEN IFV
AND
DISPLACEMENT
SECTION

PUMP OPERATING SEQUENCE
MULTIPLE DISPLACEMENT ACTUATORS
SIMULTANEOUS FULL COMPRESSION

AT REST

CLOSE IFV

OPEN IFV

COMPRESS
DISPLACEMENT
SECTION

CLOSE OFV

OPEN IFV
AND
DISPLACEMENT
SECTION

PUMP OPERATING SEQUENCE
MULTIPLE DISPLACEMENT ACTUATORS
SEQUENTIAL COMPRESSION
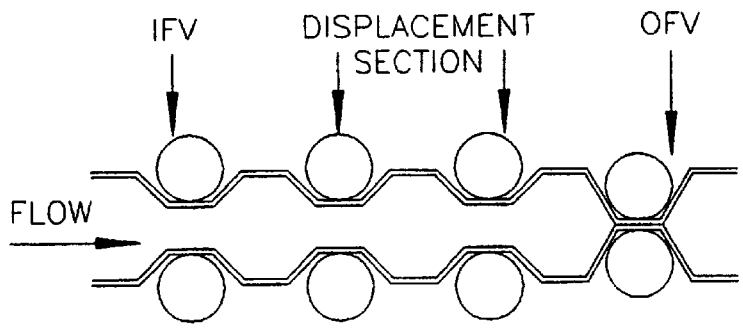
FIG. 16A
AT REST
FIG. 16B
CLOSE IFV
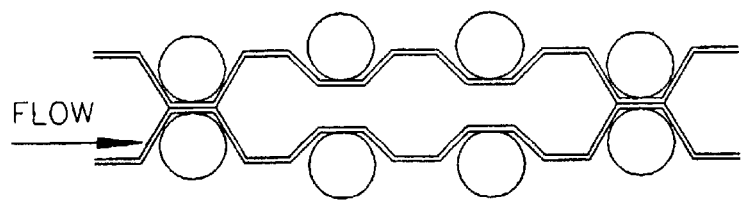
FIG. 16C
OPEN OFV
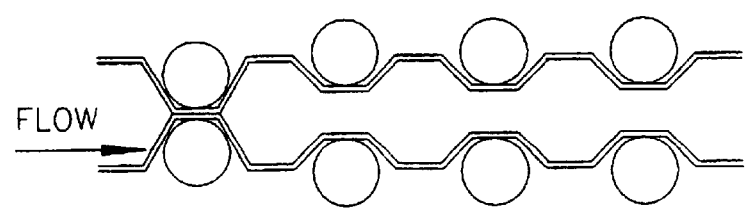
FIG. 16D
COMPRESS FIRST
DISPLACEMENT
ACTUATOR
FIG. 16E
COMPRESS SECOND
DISPLACEMENT
ACTUATOR
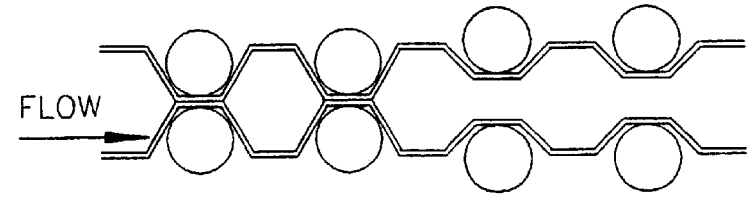
FIG. 16F
CLOSE OFV
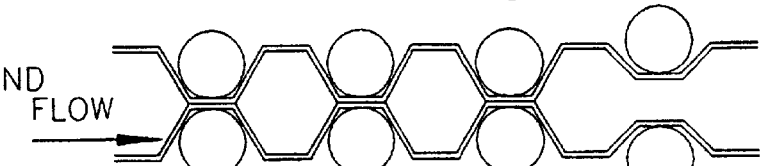
FIG. 16G
OPEN IFV
AND
DISPLACEMENT
SECTION
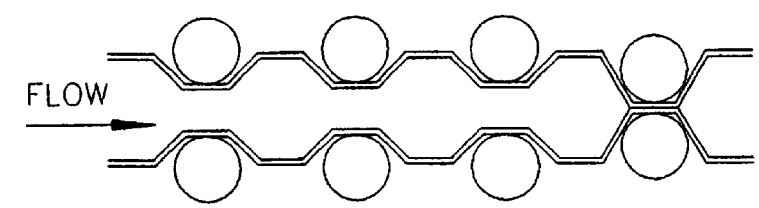

PUMP OPERATING SEQUENCE
MULTIPLE DISPLACEMENT ACTUATORS
SIMULTANEOUS ACTUATION— PARTIAL
COMPRESSION OF SECOND ACTUATOR
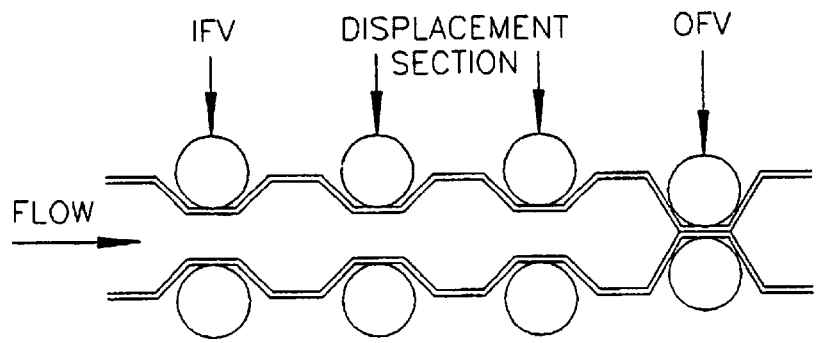
FIG. 17A
AT REST
FIG. 17B
CLOSE IFV
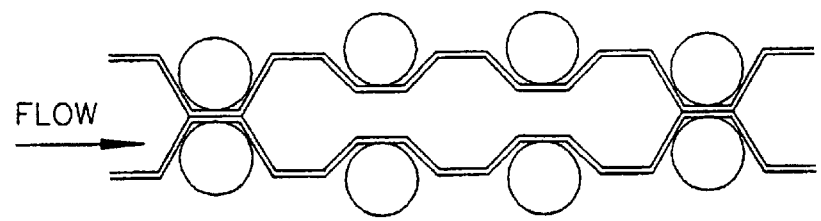
FIG. 17C
OPEN IFV
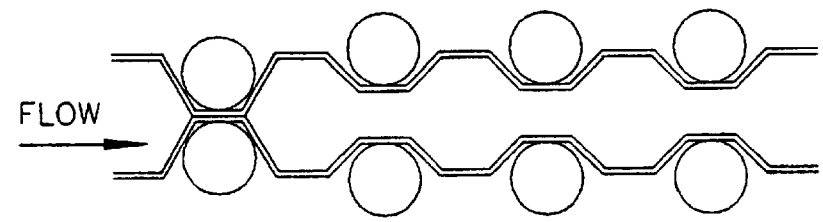
FIG. 17D
COMPRESS
DISPLACEMENT
SECTION
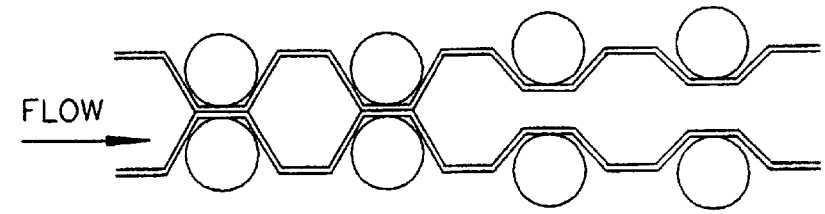
FIG. 17E
CLOSE OFV
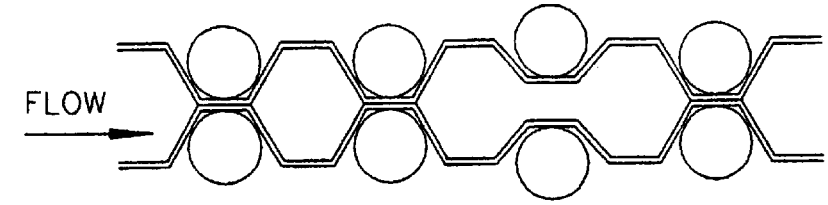
FIG. 17F
OPEN IFV
AND
DISPLACEMENT
SECTION
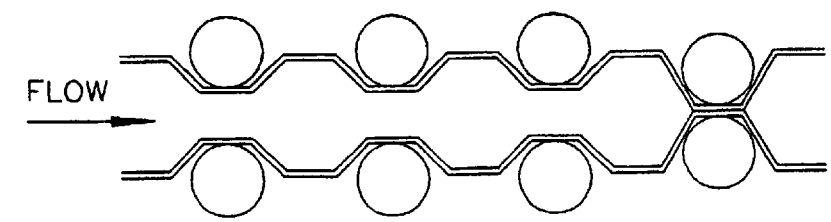

PUMP OPERATING SEQUENCE
MULTIPLE DISPLACEMENT ACTUATORS
SIMULTANEOUS PARTIAL COMPRESSION

AT REST

CLOSE IFV

OPEN IFV

COMPRESS
DISPLACEMENT
SECTION

CLOSE OFV

OPEN IFV
AND
DISPLACEMENT
SECTION

VARY THICKNESS TO DEFINE DISPLACEMENT

USE OF ELECTRONIC OUTPUT FIRING PULSE (EFP) FOR CONCURRENT METERING

A) PARALLEL DISTRIBUTION TO A PLURALITY OF PUMPS

B) CASCADING DISTRIBUTION TO A PLURALITY OF PUMPS

USE OF ELECTRONIC OUTPUT FIRING PULSE (EFP) FOR CONCURRENT DOSING

USE OF ELECTRONIC OUTPUT
FIRING PULSE (EFP) FOR
SIMULTANEOUS DOSING

USE OF ELECTRONIC OUTPUT
FIRING PULSE (EFP) FOR
SERIES PUMPING

LINEAR PERISTALTIC PUMP

This application claims benefit to Provisional Application 60/036,115 filed Jan. 17, 1997 which claims benefit to Provisional Application 60/040,232 filed Mar. 11, 1997.

TECHNICAL FIELD

The present invention relates generally to a liquid pumping apparatus. More specifically, it relates to a linear peristaltic pump apparatus, also termed a tube pump or a hose pump.

BACKGROUND OF THE INVENTION

Peristaltic pumps may be conveniently subdivided into two major types, rotary or roller types, and linear or in-line types. Rotary types are frequently encountered in laboratory, instrumentation and light commercial settings. Rotary peristaltic pumps, in which compressive elements, generally rollers, fully occlude a flexible tube as them move in a circumferential, circular arc over tubing which is supported by a circular backstop, are known to offer very limited tubing life and generally are capable of pumping only low viscosity liquids at very low discharge pressures and at very modest flow rates. As the compressive elements move over the tubing, the tubing is subjected not only to occlusive crushing but also to a stretching action along the flow axis of the tubing. This fundamental design characteristic further contributes to short tubing life and to unstable and decreasing flow characteristics of the pump over useful tubing life. There are a few commercial examples of larger hose pumps capable of broad industrial use which employ a sheathed and reinforced hose, operating in a lubricating bath, capable of pumping at higher flow rates and pressures, such as the Bredel pumps manufactured by Waukesha Fluid Handling of Delevan, Wis. However, these pumps are relatively large, expensive, and are controllable only in terms of their flow rate which is a function of the rotations per minute at which the pump is driven, and they are not usually suitable for sanitary applications such as pharmaceutical manufacturing or food processing.

Linear peristaltic pumps, or in-line designs, are unlike the rotary types in that the flow tube is acted upon only at right angles to the direction of flow of liquid through the tube. This single compressive motion eliminates the stretching and torquing forces of the rotary approach. The simplest in-line design requires a minimum of three elements, typically active, acting in a defined sequence to produce positive displacement volumetric liquid pumping action. In general terms, pumping is induced by arranging an occlusive liquid infeed valve on one end of a length of flexible tubing, placing a compressive volume displacement structure after the infeed valve, and placing an occlusive outfeed valve at the end of the tube opposite the infeed valve, such that the pump displacement element is in-between the two valves. Flow is induced when the infeed valve and displacement elements are released from compression and allowed to fill with liquid either as a result of the suction action resulting from the creation of a lumen, or by an external feed means. During this priming phase, the outfeed valve remains occluded. The infeed valve is then closed, after which the outfeed valve is opened, after which the displacement element is compressed. The cycle is then repeated.

Linear peristaltic pumps, or in-line peristaltic pumps, are commercially largely confined to medical applications such as intravenous pumps and infusion pumps, but have a long and substantial history in the patent art. Phelps (U.S. Pat. No. 2,105,200; 1938) teaches a pump with three compressive blade-like elements, one serving as an infeed valve, one serving as a volume displacement element, and one serving as an outfeed valve. The flow tube is placed on a flat surface and all three actuators act upon the tubing only from one side. Tarbox (U.S. Pat. No. 2,393,838; 1946) teaches a three element linear design in which the infeed and outfeed valves act from opposite sides of the flow tube, the compressive section is an elongated structure, and the occlusive motion imposed upon the flow tube is entirely from one side or the other. Harper (U.S. Pat. No. 2,412,397; 1946) discloses a three element linear design in which the flow tube is on a flat surface and acted upon by all three actuators from the same side. Anderson (U.S. Pat. No. 3,518,033; 1970) teaches a three element linear peristaltic pump with two blade-like valves and a displacement compression plate, all operating upon a flexible tubing on a flat substrate and from the same side. Each of these cited designs utilizes a motor and cam arrangement to sequence and activate the three pump elements. Schill (U.S. Pat. No. 3,811,800; 1974) shows a three element pump wherein the infeed and outfeed valves are cone nosed rods actuated by pneumatic cylinders while the pump displacement actuator consists of another inflatable tube bearing upon the flexible liquid flow tube, all elements acting upon the same side of the flow tube. In U.K. Patent 1,426,963 (1976), Makarov discloses a linear pump, pneumatically operated, and sequenced, wherein pneumatically pressurizable chambers surrounding the liquid flow tube act to occlude the liquid flow tube. Björklund (U.S. Pat. No. 3,998,104; 1976) teaches a three element cam driven linear design where wedge shaped anvils serve as valves, a larger wedge serves as the displacement element, and all are acting upon the tube from the same side, the tube being supported upon a flat surface, and all occlusive motion is imparted to the tube entirely from one side. In U.K. Patent 2,020,735 A (1979), Schal discloses still another three element cam driven peristaltic design with two finger-like valves and an elongated center compression plate, all acting from one side of a tube supported against an abutment. In U.K. Patent 2,057,067 (1980) Moore teaches a design in which the flow tube is occluded in three successive pressure compartments by hydraulic pressure to create a linear peristaltic pump consisting of an inlet valve, an outlet valve and a displacement member. Kobayashi (U.S. Pat. No. 4,479,797; 1984) discloses a three element linear peristaltic pump consisting of cantilevered fingers, each cam driven from the same side of the tube against the straight flow tube. Blette (U.S. Pat. No. 4,967,940; 1990) presents a cam driven three element linear peristaltic pump with a fourth element added, termed a compensator, to provide a reverse flow such back in a dispensing arrangement. In U.S. Pat. No. 5,131,816 (1992), Brown teaches a cam driven three element pump with an infeed valve, an outfeed valve and a larger pump displacement element interposed between them. All elements bear upon the pump tube from one side, with the tube supported upon a flat surface. In PCT Publication WO 94/21918 Grapes discloses a three element linear peristaltic pump in which pneumatic cylinders and solenoid valves are utilized. The volumetric displacement section consists of a compression plate pressed upon by two pneumatic pistons which are, in turn, operated upon by a single solenoid valve. An infeed valve is occluded by a spring mechanism and opened by a pneumatic cylinder. An outfeed valve is formed by a V-shaped anvil pressed upon the flexible pump tube by a fourth pneumatic piston. The tubing rests upon a flat surface and tubing occlusion is from one side of the tube only, such that only one wall of the tube flexes across the entire internal diameter to effect occlusion.

Although the general form of the three element linear peristaltic pump has been widely applied in the prior art, many limitations and shortcomings of these designs are evident. Some of these will now be listed and briefly discussed:

1. Inability of prior designs to pump liquids at comparatively high pressures. Nearly all of the previous designs utilize a small scale and method of construction unsuited to provide the power needed for high pressure pumping. The liquid flow tubes are generally soft comparatively flexible material unable to contain high differential pressures and they are not typically contained to prevent pressure distortion or rupture. The compressive elements are most typically of a geometry unsuited to high force application to the tube wall in order to create the high pressure pinch valving required of a high pressure pump. Where high pressure linear peristaltic designs have been attempted, they have utilized hydraulic actuation, requiring expensive pump construction and limiting utility because of the requirement for a high capacity and pressure hydraulic supply.

2. Inability of prior designs to pump high viscosity liquids. Pumping high viscosity liquids will generate high pump discharge pressures. The inability of known types to pump at high pressures has previously been discussed. In addition, to pump high viscosity liquids a competent and useful pump must be capable, by its own action, of priming such liquids into the pump at start-up and during continuous running. The devices of the prior art are not generally suited to this in that the rebound capability of the liquid flow tube is extremely inadequate to such service. Further, there are usually no provisions or ability to allow independent control and adjustment of the priming function within the pump cycle, and the compression anvils which are in contact with the tubing are not geometrically suited to the high force operation required for such service.

3. Inability of prior designs to pump liquids at comparatively high flow rates. Three element designs of the prior art are typically designed for low flow medical or laboratory applications, or for dosing of very small volumetric quantities. The designs of the prior art are not suited to high flow applications due to the prevalent use of thin walled, relatively soft tubing which cannot rebound with sufficient speed to re-prime the pump with adequate speed to allow the fast cycle speeds necessary for high flow rates.

4. Inability of prior art linear three element peristaltic pump designs to provide long term pump tube service capability. Known designs are frequently intended for service where the pump tube is considered disposable and such disposal occurs frequently. In other cases, the liquid bearing tube is of single walled thin section construction and not able to withstand hundreds of thousands or millions of repeated flexure cycles in the same location on the tube wall without physical degradation or rupture. In most cases, other design elements of the prior art pumps, such as the tube compression elements or actuators or drive elements, are not sufficiently robust for long term service in general pumping applications.

5. Inability of prior art designs to be capable of increasing liquid flow rates by increasing the area of displacement compression on the flow tube without loss of pump pressure capability. Designs of known type do not disclose means for increasing the total compression force acting upon the flow tube in order to maintain the force per unit area as is required in order to allow for the increase in the square area of tube compression needed for increased pump flow rates without loss of pump discharge pressure capability.

6. Inability of designs of the prior art to provide a high degree of flexibility and versatility of service in the same embodiment, including the ability to provide sustained pumping, precision metering, and full dosing capability with electronic interface and control capability including independent adjustment of pump operating parameters such as pumping pressure, liquid flow rate, pumping frequency, and viscous priming capability, particularly while the pump is operating.

7. Inability of prior designs to provide long term stability and predictability of pumping performance. Designs of the prior art are known to exhibit a substantial decrease in volumetric flow rates over time as a function of the fatigue and compression set effects of the pump flow tubes and the mechanisms applied to these tubes. Designs of the prior art do not disclose mechanical or electronic means to monitor, extend and maintain pumping performance capability over the life of the device.

OBJECTS AND SUMMARY OF THE INVENTION

It is a primary object of the present invention to overcome the numerous limitations and disadvantages of linear peristaltic pumps of known type, as set forth above. Moreover, it is a primary object of the present invention to present a unique design for a linear peristaltic pump, the particulars of which allow many new and novel features and capabilities as will be set forth in detail further on.

It is a further object of the present invention to provide a linear peristaltic pumping apparatus for pumping liquids which includes a high durometer compressible elastomeric liquid flow tube, an infeed valve assembly, an outfeed valve assembly, an extensible and retractable actuator anvil having a round surface which engages the flow tube at all times, an opposed anvil having a round surface in engagement with the flow tube at all times, the flow tube being held between the anvils in a slightly compressed state when the actuator anvil is retracted, and control means for causing the movable anvil to be sequentially extended and retracted to cause flow within the flow tube from the infeed valve assembly to the outfeed valve assembly. With this apparatus the lumen of the flow tube to the sides of the anvils is not completely reduced to zero volume during displacement compression whereby gas embolisms do not erupt or explode when discharged.

In summary, the in-line or linear three element electronically controlled peristaltic pump of this invention is provided with linear actuators, typically pneumatic, each actuator capable of driving dual symmetrical pump tube compression anvils which compress a high durometer reinforced multi-layer flow tube from each side such that a higher liquid pumping pressure can be produced than the pneumatic pressure applied to the actuators. The high durometer flow tube allows priming and pumping of liquids at viscosities and pressures not previously possible with a linear peristaltic pump. The dual symmetrical anvil arrangement greatly extends useful pump tube life. Additional displacement actuators may be added in modules to increase flow range without loss of pressure or viscosity capability.

The pump infeed valve is constructed to provide necessary higher differential pressure capability than any other pump element, further improving high pressure performance, and the infeed valve is uniquely maintained in an open and uncompressed condition when the pump is not pumping, preventing long term fatigue of the priming section of the pump. Pneumatic solenoid control valves which are directly coupled to the actuators in the preferred embodiment minimize pressurized gas consumption and contribute to high speed operation by eliminating system gas volume latency. The invention has a capability to pump, without degradation, large solids included or entrained in the liquid. The pump tube is surrounded with rigid cylindrical pressure rings between the compressive anvils, further increasing high pressure capability and speeding tubing rebound to open the pump tube lumen after compression. The actuators can be sensor encoded for each end of their stroke thus allowing closed loop and optimized electronic position and sequence control for varying conditions and for flexible and versatile pump usage. Pump flow rate may be directly electronically controlled in several ways, including by the use of a linear encoder on the displacement actuator, and pump discharge pressure is controllable over a broad range. Bidirectional pumping capability is inherent to the design as is dosing capability with essentially infinitely variable dose volume setting. Control electronics, typically a microcontroller, allows high versatility of application and great ease of use, as well as substantial diagnostic capabilities.

The above will be more fully understood after a consideration of the following detailed description taken in conjunction with the accompanying drawings in which preferred forms of this invention are illustrated.

BRIEF DESCRIPTION OF THE DRAWINGS

FIG. 7A is a detail view of a portion of the structure shown in FIG. 7.

FIG. 9 is an exploded view of an actuator, operating rod, and anvil.

FIGS. 10 and 10A are front and right side views of the cover plate or anvil plate.

FIGS. 15A–15F, 16A–16F, 17A–17F, and 18A–18F illustrate schematically various manners in which the pump of FIGS. 13A and 14A may be operated.

DETAILED DESCRIPTION

IN GENERAL—FIRST EMBODIMENT

Figure 1:
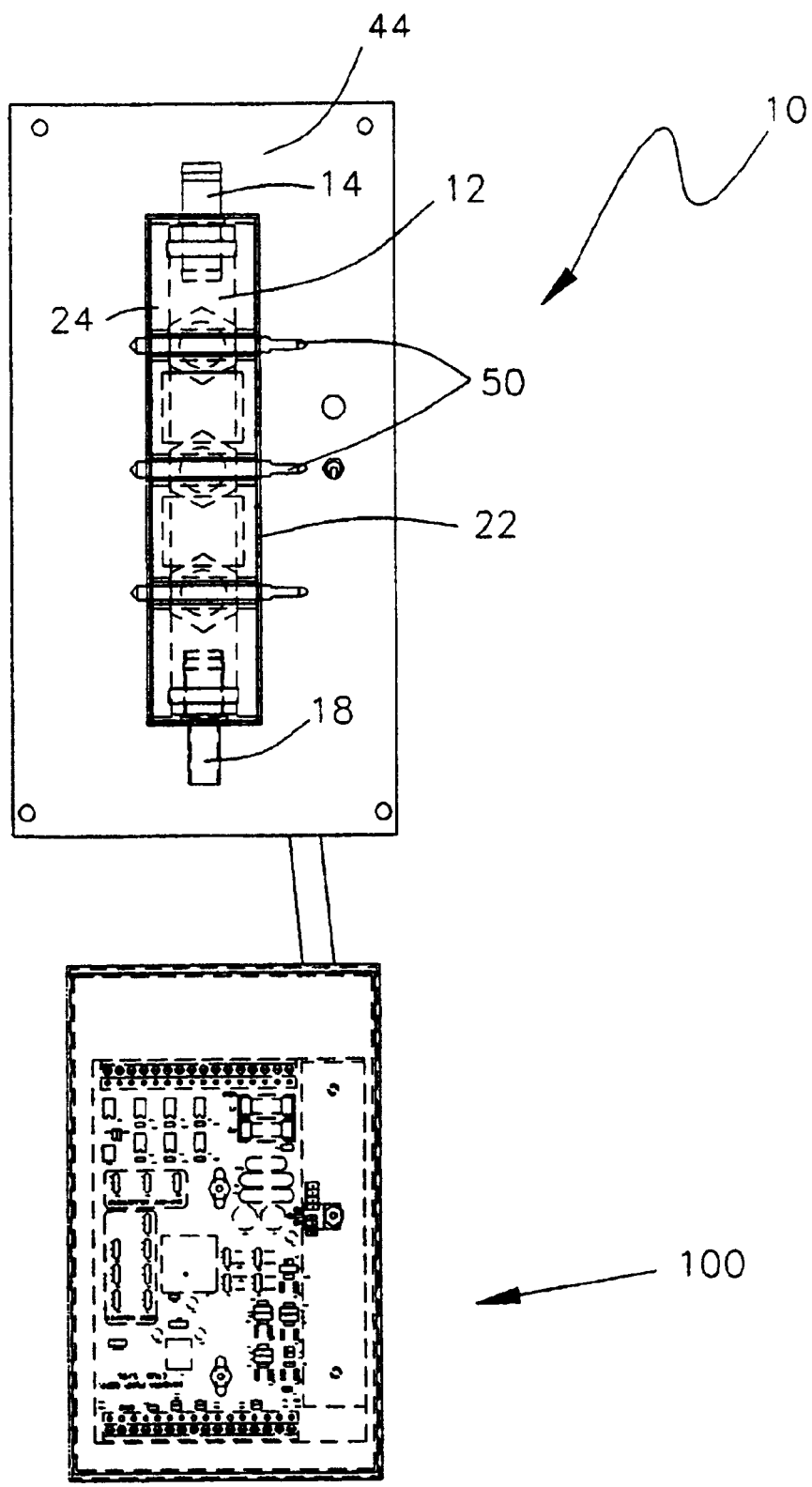
FIGS. 1 and 2 are front and right side views of the first embodiment of the linear peristaltic pump of this invention including its electronic control module.
Figure 2:
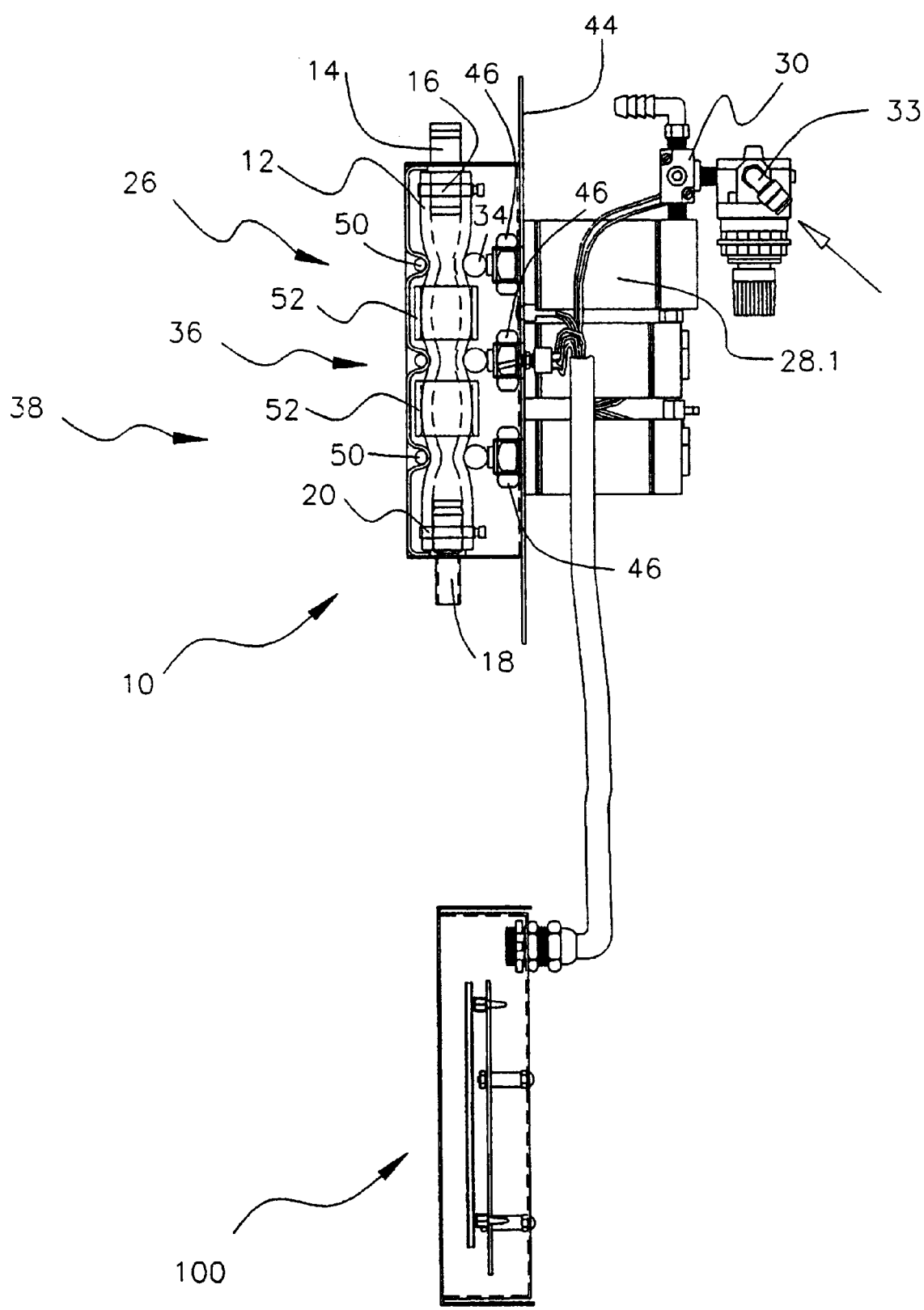
Figure 3:
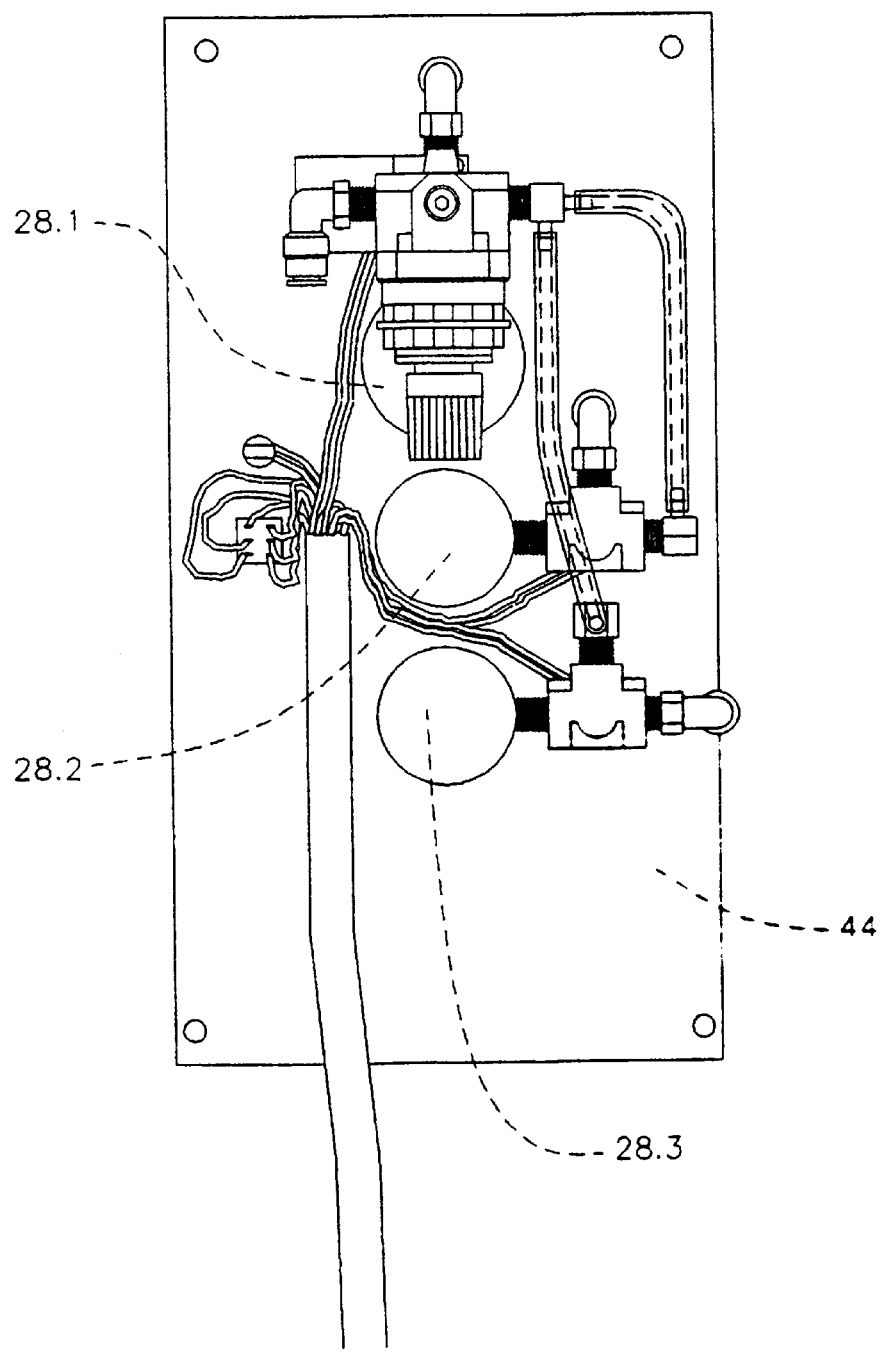
FIGS. 3 and 4 are back and left side views of the pump of this invention, the control module being not shown.
Figure 4:
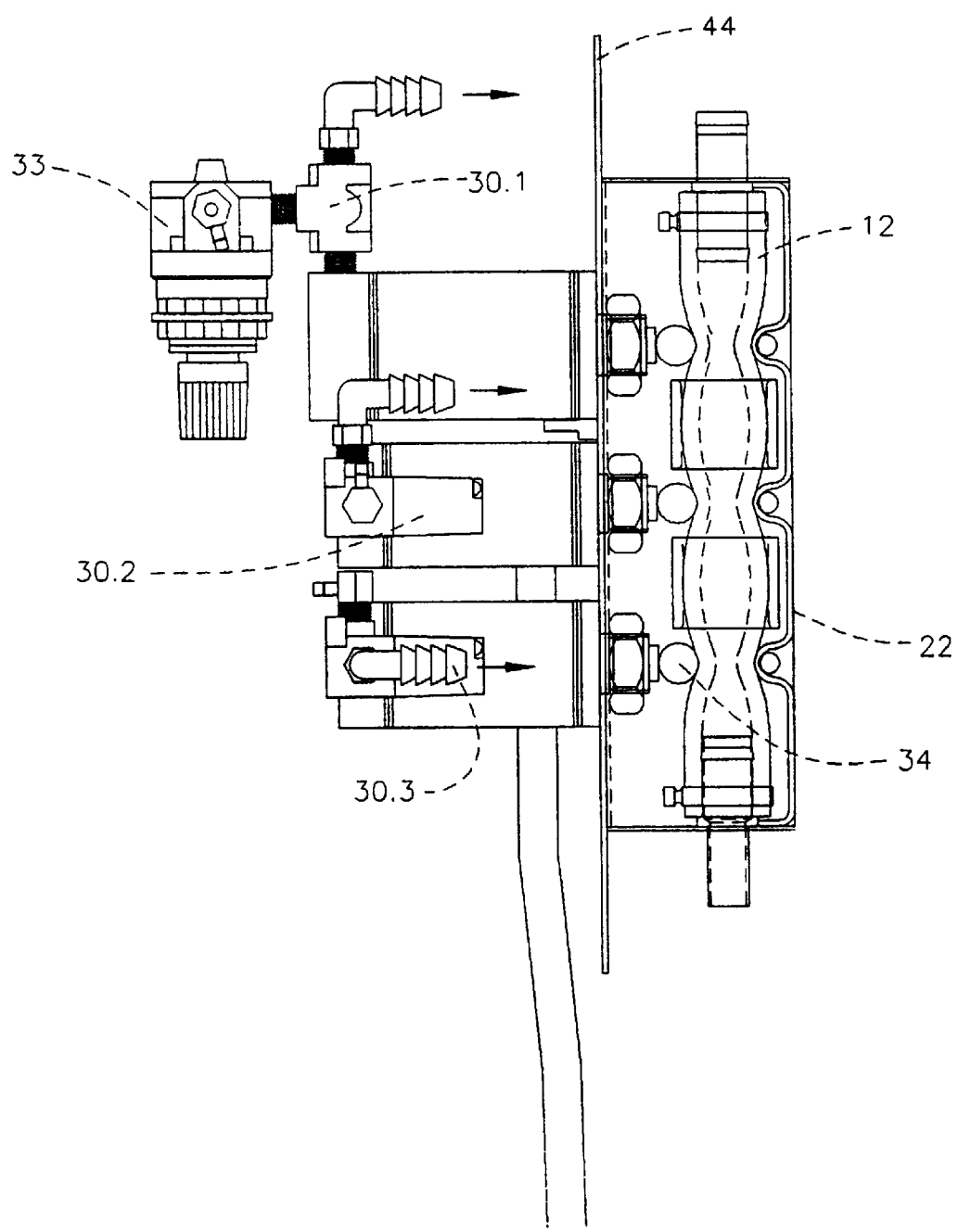

The present invention consists of a linear or in-line three element peristaltic pump, indicated generally at 10 in FIGS. 1–4, the peristaltic pump also being known as a tube pump or hose pump. In general, the pump consists of a pump liquid flow tube 12 which is suitably acted upon to create flow, the inlet end of the pump tube 12 being connected to an inlet tube (not shown) via an inlet hose barb 14 which is held in place by a clamp 16. The outlet end of the pump tube 12 is connected to an outlet tube (not shown) via an outlet hose barb 18 which is held in place by a clamp 20. The pump tube is mounted within a U-shaped pump housing or support channel 22 which is closed by an anvil plate 24 having spaced apart integrally formed anvils 24.1. The U-shaped channel has a bight portion 22.1, and spaced apart side walls 22.2 and 22.3.

The three element pump includes three principal active or actuating assemblies (or elements) which act upon the pump tube 12. The first principal or active element in the hose pump of the present invention is the occlusive infeed valve assembly indicated generally at 26. The infeed valve assembly consists of a linear actuator or force applying means, typically a pneumatic cylinder 28.1 having a pneumatic port 29, closely connected to a solenoid operated pneumatic valve 30.1 via a fitting 31. Affixed to the operating rod 32 (FIG. 9) of the actuator 28.1 is an anvil 34 of particular geometry which bears upon the pump liquid flow tube 12 in a particular way, all of which will be described in detail further on. The cylinder 28.1 control valve 30.1 and anvil 34 of the first actuating assembly, taken together, may be considered to be the infeed valve or infeed valve assembly, i.e., the first element of the three element pump. It is to be understood that the pneumatic cylinder 28.1 is the preferred force applying means. However, it could be replaced with other linear actuating or force applying means, including, but not limited to, hydraulic cylinders, electric solenoids, voice coil actuators, ball screw drives, rack and pinion drives, piezoelectric devices, and thermal expansion displacement devices. The infeed valve assembly may alternatively be termed the inlet valve, the suction valve, or the feed valve. For ease of discussion and usage, this valve assembly will be henceforth referred to as the IFV, a short form for infeed valve. The solenoid valve 30.1 which is connected to the cylinder 28.1 is a 2 position 3-way valve which is connected to a regulated source of air under pressure by a suitable line in such a manner that it will be normally closed. Air is regulated by an adjustable regulator 33. When the valve 30.1 is in its normally closed position, the cylinder 28.1 is pneumatically connected to exhaust. When electrically actuated, the valve 30.1 is shifted to its second position, and the cylinder 28.1 is pneumatically connected with the regulated source of air pressure through an air pressure line or the like.

The second principal or active element in the hose pump of the present invention is the displacement assembly, indicated generally at 36. (It is also referred to as the pumping element or the displacement element, the pumping section, or the compression section). It consists principally of the same constituents as the IFV, specifically an actuator 28.2, a valve 30.2, an operating rod 32, and an anvil 34. It is important to note that, as will be explained further on, the second principal or active element in the hose assembly, namely the displacement assembly or pumping element can consist of one complete actuator assembly, or it can consist of more than one. When more than one actuator contributes to the pumping element, all such actuators taken together, may be referred to as the pumping element or displacement assembly or element. Also detailed further on, the pumping element may be valved in a different manner than the IFV to achieve particular benefits.

Figure 12A:
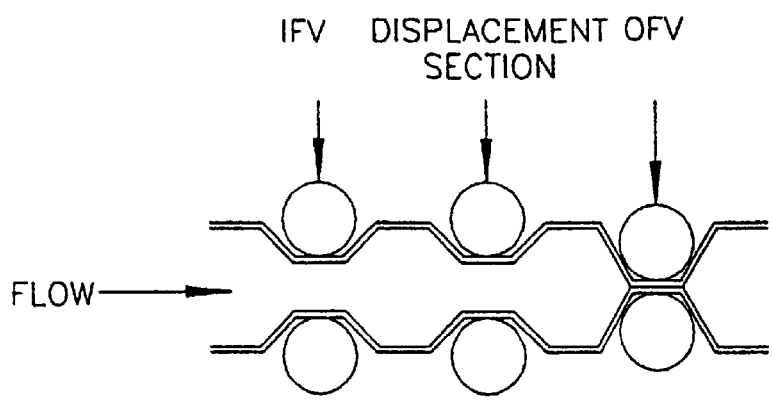
FIGS. 12A–12F illustrate schematically the manner in which the pump tube is acted upon to cause pumping.
Figure 12B:
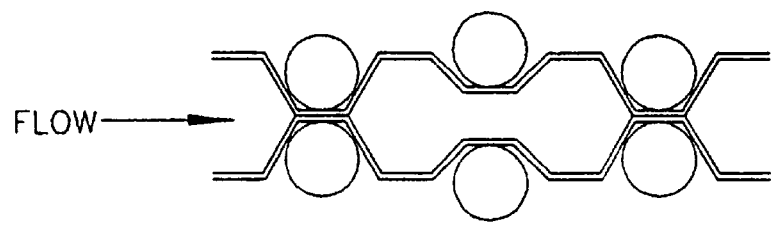
Figure 12C:
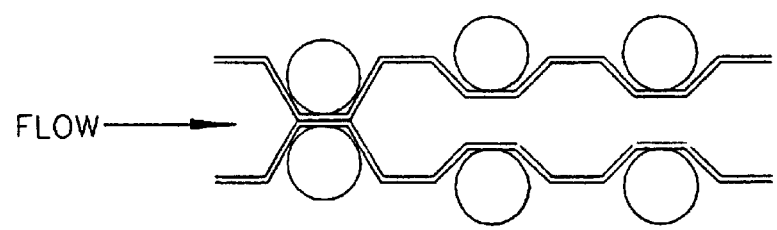
Figure 12D:
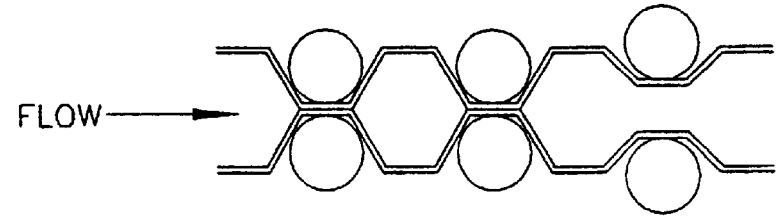
Figure 12E:
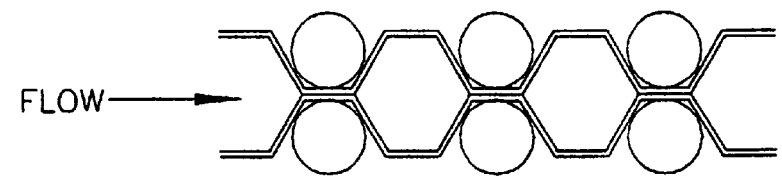
Figure 12F:
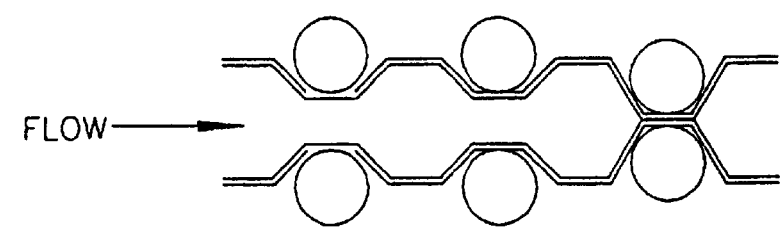

The third principal or active element is the occlusive outfeed valve assembly indicated generally at 38. The outfeed valve consists of the same principal components as described for the IFV and pumping element, namely a linear actuator or force applying means 28.3, a valve 30.3, and an anvil 34. The outfeed valve may alternatively be termed the outlet valve, the discharge valve or the delivery valve. For simplicity, hereafter it will be referred to as the OFV, a short term for outfeed valve. As can be appreciated from an inspection of FIG. 12A, the valve 30.3 will be plumbed so that in its normal at rest position, the cylinder 28.3 will be connected with the source of regulated air so that the rod 32 is extended.

Sensors 35.1 and 35.2 may, in one preferred embodiment, be affixed to the actuator or its moving elements in order to derive position information regarding the actuator for control purposes, as for example from a magnetic sensing strip 35.3 carried by the piston of an actuator. Alternatively, sensors may be mounted to sense a moving element of the actuator. The unique use and benefits of these sensors will be detailed further on.

The novel and unique features of the pump will now be listed and detailed and the particular benefits derived therefrom will be discussed.

FIRST NOVEL FEATURE

In the preferred embodiments, the method of construction is unique and serves to allow many of the novel design and performance features to be implemented to good effect. In the embodiment illustrated in FIGS. 1 to 12 the U-shaped channel is preferably constructed of stainless steel sheet, but may be fabricated of many other materials as well, including molded plastic. Inlet and outlet slotted end plates 40, 42, respectively, which are formed from extensions of the bight portion 22.1 of the U-shaped channel, are secured to the ends of the U-shaped channel in any conventional manner, such as be welding if the parts are made of stainless steel. As the barbs 14, 18 are of differing diameters, the slots 40.1 and 42.1 in plates 40, 42, respectively are also of differing widths. The U-shaped channel provides a very strong and rigid structure which is necessary to the design while preserving an economy of construction. It also contributes to the ability of the design to provide extended long term durability and stability of pumping performance.

The use of a stainless steel U-shaped channel 22 gives a simple, effective and low cost structure of high strength and rigidity suitable as a mount for the three actuator elements previously described, and serving, at the same time, as the constraining element for the actuator anvils 34 thus preventing their rotation about the actuator cylinder rods 32. As will be understood by one skilled in the art, air cylinder actuators are generally constructed such that the actuated piston rod 32 is free to rotate about its center. The U-shaped channel walls 22.2 and 22.3 are used as a means to prevent this, thus eliminating any other additional cost to achieve this necessary function. It is notable that the need to prevent anvil rotation such that each anvil is correctly oriented across the width of the channel only occurs while the pump liquid flow tube 12 is removed from the pump. Once installed into the pump, each rod carried anvil 34 is firmly pre-compressed against the wall of pump tube 12 and this strong engagement causes the anvils to show no tendency to rotate.

The three actuating elements 26, 36, 38 of the pump 10 are fastened into the U-shaped channel such that the rod end of each actuator protrudes into the U-shaped channel. The actuators are on the center line of the long axis of the channel. Captured between the bottom of the U-shaped channel and the nose of each actuator is a flat plate 44, typically a stainless steel sheet, which serves as a mounting plate for the assembled pump. In the basic three cylinder embodiment, only three nuts 46, one threaded onto the nose of each cylinder, hold the entire apparatus together. The anvils 34 typically made of stainless round bar stock, have a blind hole 34.1 on the circumference of the structure which is centered from each end. This allows the anvil to be attached to the end of the cylinder rod, using a spring pin 48 which is pressed into the anvil and into a matching hole 32.1 in the end of the cylinder rod 32.

The flow tube 12, with fittings 14, 18 attached, is sized to a length which allows it to simply drop into the U-shaped channel from the open side with the hose fittings being captured on three sides by the end slots. The width of the U-shaped channel is adequate to allow for the flow tube width without tube to wall contact when it is in its widest dimension which is when it is completely compressed such that the internal walls on opposite sides of the tube are in contact with each other.

As will be more fully explained later, the straight flow tube 12 is extremely rigid and thus self centers along the center line of the long axis of the U-shaped channel upon its insertion into the pump, and upon the entry of the fluid fittings 14, 18 affixed to each end of the tube into the end slots previously described.

Once the fluid flow tube is placed into the pump, with the linear actuators 28.1, 28.2, and 28.3 fully retracted away from the tube side of the pump, the cover or anvil plate 24, otherwise termed a top anvil plate, is fitted. The cover plate 24 is preferably fashioned from a comparatively rigid stainless sheet stock but could be constructed of other suitable material such as molded plastic. The cover plate is a serpentine shape and serves at once three distinct functions: to form a matching round top anvil shape 24.1 opposite from the anvil 34 affixed to each actuator 28.1, 28.2, and 28.3, to lock into position the pump hose fittings at each end of the pump by use of locking tongues 24.2 and 24.3; and to provide a secure cover for the complete pump assembly.

The cover plate is rigid and upon placement onto the U-shaped channel box structure which forms the pump body, it self positions in the long axis by virtue of the engagement of the locking tongue formed at each end of the cover plate, and this causes the rounded top anvils 24.1 to be approximately positioned opposite those anvils 34 on the actuators 28.1, 28.2, and 28.3. The cover plate is constrained from side movement along the long axis of the U-shaped channel by the side walls of the channel which are of sufficient height as to protrude beyond the anvil portions of the cover plate. The cover plate is symmetrical as a function of the spacing of the actuators which, in the preferred embodiment, are on repeating center dimensions. This symmetry allows the cover plate to be installed without concern for correct orientation, end to end. The pump cover plate is secured to the pump body in a particular manner, both simple and precise. In the preferred embodiment, the long sides of the U-shaped channel are cross drilled such that a hole is placed on each side in the centerline position of each actuator anvil 34, relative to its linear motion. The hole is spaced relative to the retracted actuator anvil so that when the cover plate is manually pushed down upon the liquid flow tube, a round pull pin 50, typically of stainless steel, is inserted into any one of the holes on one side of the pump, across the face of the cover plate coincident with a concave top anvil location as formed by the shape of the cover plate in that location, and into and through the matching hole on the opposite side of the U-channel.

The unique benefits of this method of construction of this first embodiment of the invention are several. First, when the top plate 24 is pushed down upon the pump hose 12, the hose is partially and symmetrically compressed between the anvils 34 and 24.1, as can best be seen from FIG. 5A. This firmly captures the tube 12 such that the ends are captured by the hose fittings, and intermediate portions of the tube at each matched and symmetrical anvil position. As will be shown, this partial symmetrical compression and highly defined capture of the tube at the points noted is critical to the beneficial operation of the present invention. Second, the means of attachment of the top plate also assures that the assembly is made to a precisely predetermined dimensional relationship relative to a particular size pump tube and a particularly sized embodiment of the pump. Third, the means of attachment also assures a very simple and self evident procedure for assembly and one which can be visually checked for correctness by direct observation. Fourth, the means of attachment in combination with the U-shaped channel method also assures an extremely rigid assembly capable of indefinitely withstanding the very high compressive forces, which can typically be in the hundreds or thousands of pounds, which will be applied by the actuators. This is particularly the case because each pull pin is attached at the center of the force axis applied by each actuator along the axis of the rod 32, the force axes corresponding to the center lines 26CL, 36CL, and 38CL. The necessity of a particularly strong structure for the pump of the present invention will be more evident further on. Fifth, the means of attachment of the top plate 24 readily and uniquely allows the use of a range of pump flow tube sizes within a given pump size. It is straight forward to install a tube of an outside and inside diameter smaller than that of the maximum size for which a particular sized embodiment is designed. This is simply done by either inserting a round or half round spacer (50.1 or 50.2, respectively) of suitable thickness about each of the pull pins 50 so that the cover plate anvils 24.1 are forced closer to the actuator anvils 34, thus establishing the desired and proper degree of symmetrical compression capture of the smaller tube. Alternatively, a unitized spacer 23 consisting of a single serpentine piece may be overlaid to match the original cover piece and then assembled as previously described. It is also possible to completely replace the cover piece with a thicker unit thus achieving the same effect.

In conjunction with the unique and novel construction of the pump of the present invention, it is important to note that the linear actuators utilized, typically and preferably pneumatic cylinders 28, are capable in typical and normal service of at least 100 million complete reciprocations. The pneumatic solenoid valves 30 utilized in the preferred embodiment are capable in typical and normal service of at least 250 million actuations. As will be explained, the durability of these devices, in conjunction with the robust and durable construction of the pump is important to the benefits to be derived from the present invention. In terms of overall construction of this embodiment, in comparison with known linear peristaltic pumps, it is evident that the design of the pump of the present invention uniquely provides a means to achieve high actuating forces within a robust and rigid structure, all with a high degree of longevity and durability.

SECOND NOVEL FEATURE

The second novel and unique feature of the present invention is derived from the method of construction of the preferred embodiment and consists of the symmetrical dual round tube compression anvil design.

Figure 5:
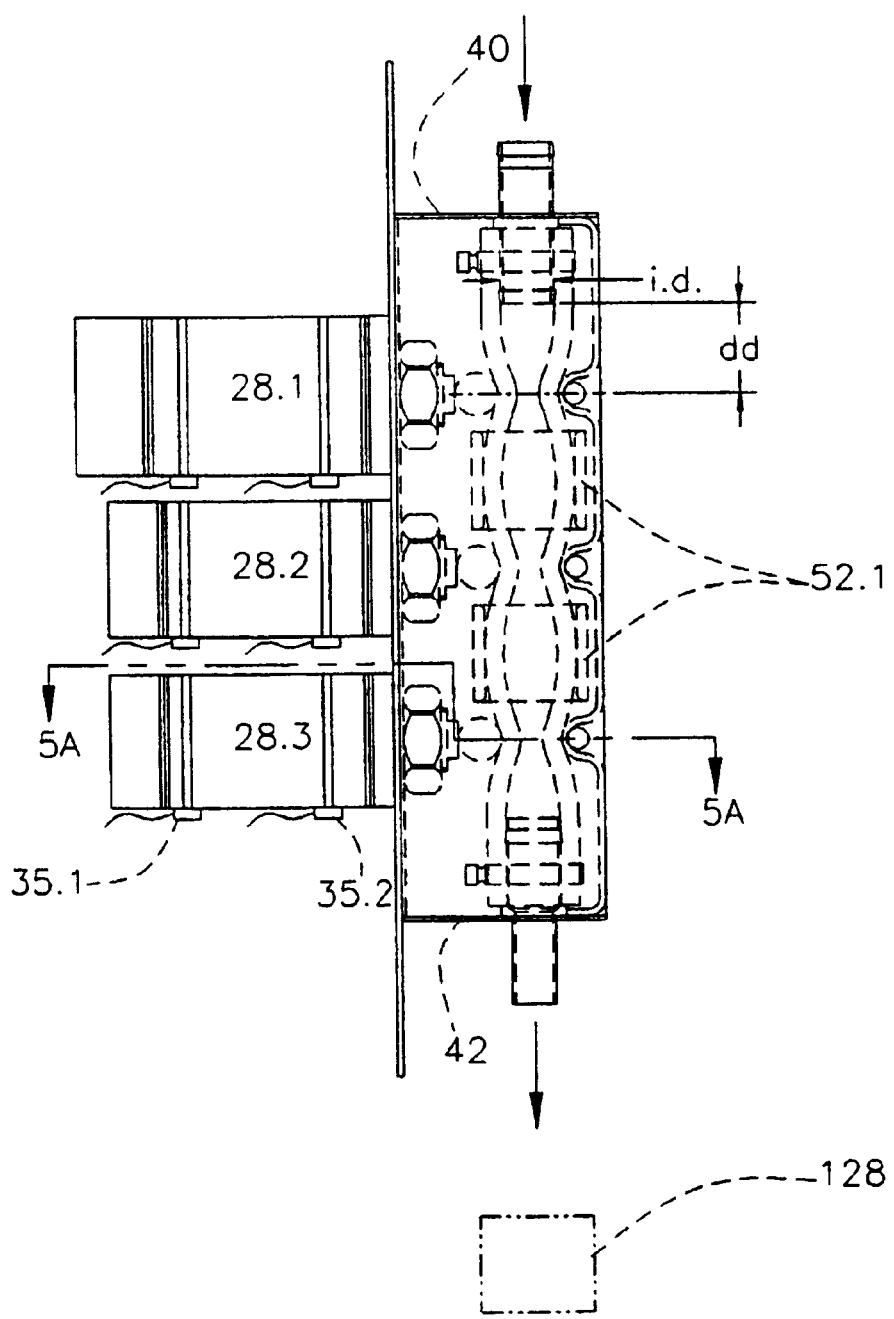
FIG. 5 is an view of the pump shown in FIG. 4, parts being eliminated for purposes of clarity.
Figure 5A:
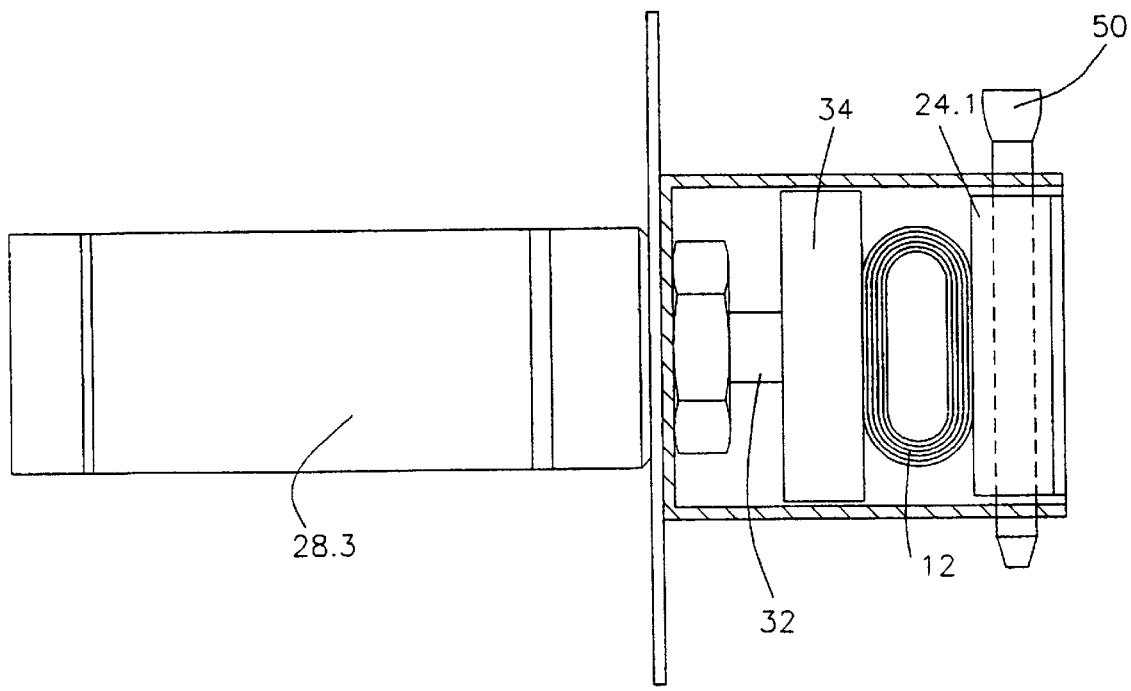
FIG. 5A is an enlarged section taken generally along the line 5A—5A in FIG. 5, the pump tube being shown prior to compression.

When assembled, and with all actuators retracted, the pump liquid flow tube is symmetrically partially compressed on opposite sides at each anvil location. This arrangement of symmetrical anvils with partial pre-compression allows the pump tube 12 to "float" in the pump with essentially equal pre-compression deflection and force from each side of the tube. That is, the tube is largely symmetrically captured from both sides and does not contact any substrate or platen or other flat surface of the pump, as is the case in prior art, but rather is positioned by and in contact with only the anvils in these major element positions and the end fitting capture slots. Thus, this symmetrical dual round anvil design, coupled with partial pre-compression of the pump tube, creates a profile of the flow tube wall, in longitudinal section, which is opposite sinusoidal, that is, asymmetrical sine curves which are 180 degrees out of phase, as shown in FIG. 5. This shape is unique when compared to the "periodic peaks" pattern of the known art. It is novel and highly beneficial in numerous ways. It allows static and dynamic hydraulic pressure balancing within the tube lumen. It also allows substantial load force balancing of externally applied actuations of the pump tube. This equilateral pressure and load distribution within and without the flow tube greatly increases the useful life of the pump tube. Just as important, it contributes to a high predictability and stability of pump performance from the time when a pump tube enters service to the end of its useful life.

Figure 5B:
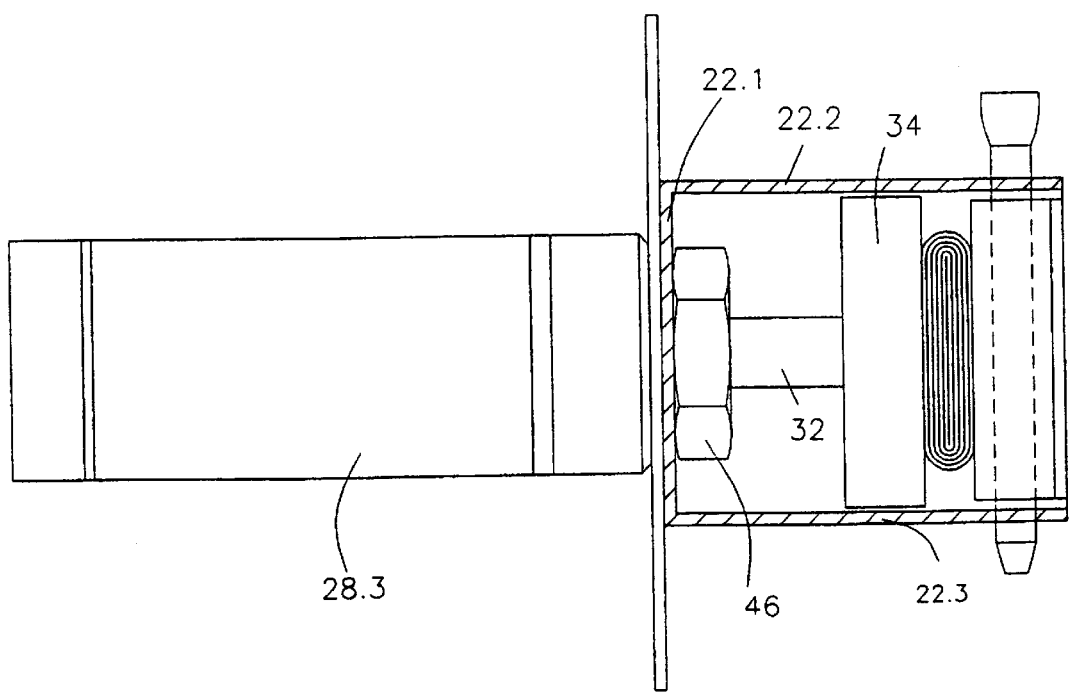
FIG. 5B is a view similar to FIG. 5A, but showing the pump tube fully occluded.
Figure 5C:
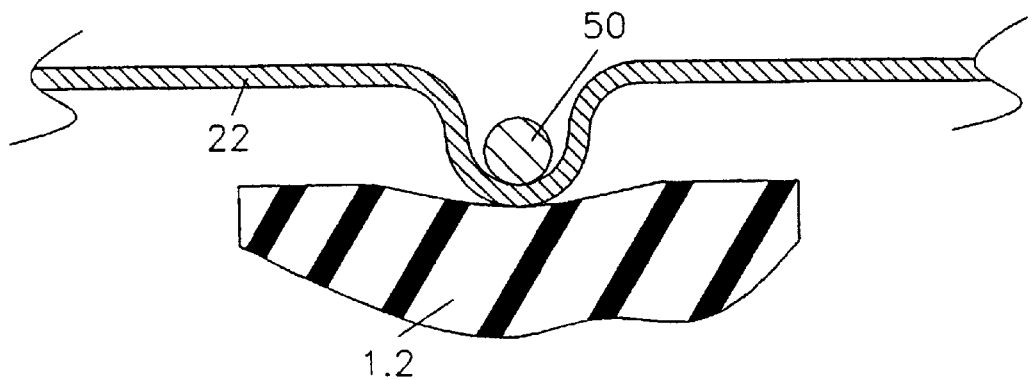
FIG. 5C is a sectional view showing the manner in which the top plate bears against the tube prior to compression.
Figure 5D:
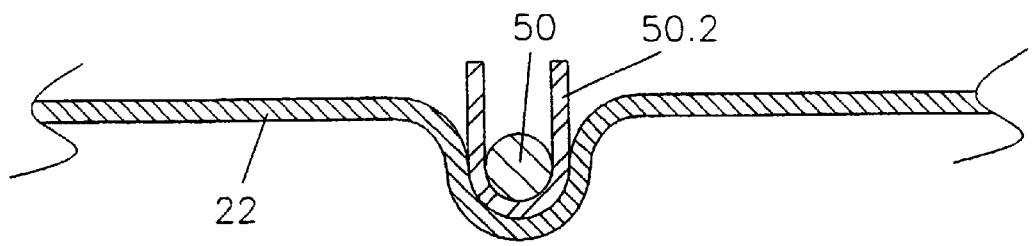
FIGS. 5D–5F are sectional views similar to FIG. 5C, but showing how differing shims may be employed.
Figure 5E:
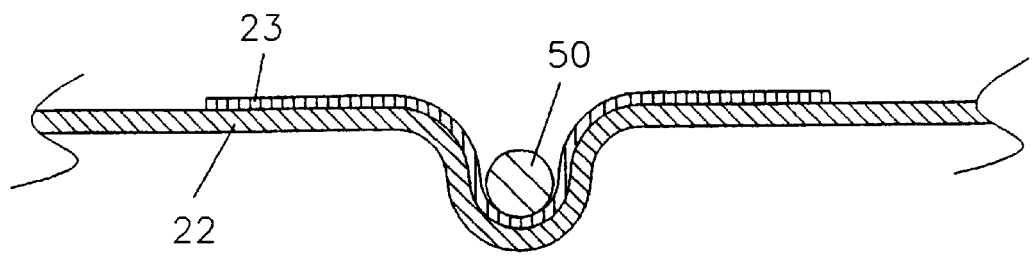
Figure 5F:
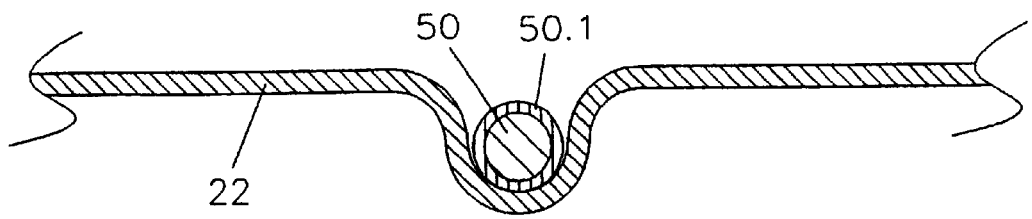
Figure 6:
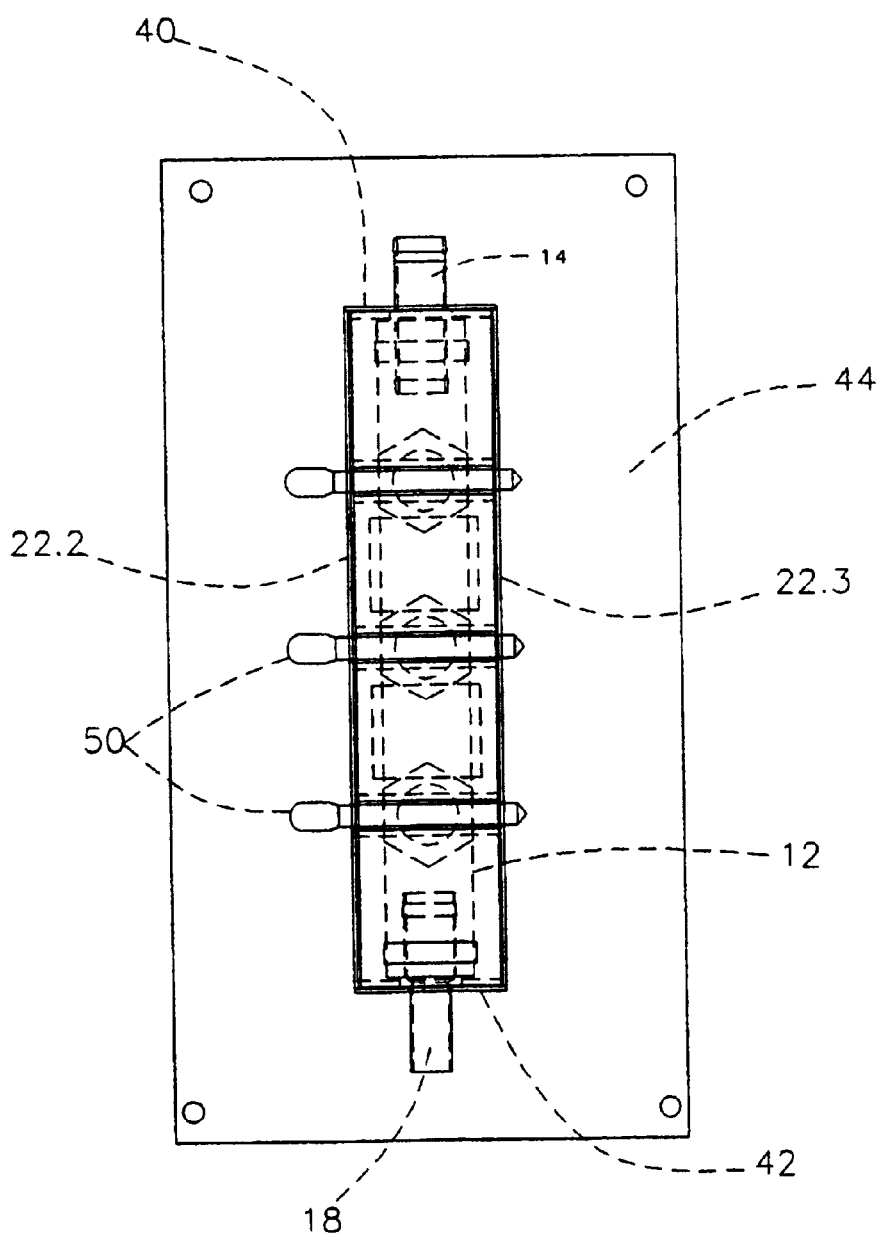
FIG. 6 is a front view of the pump shown in FIG. 5.
Figure 7:
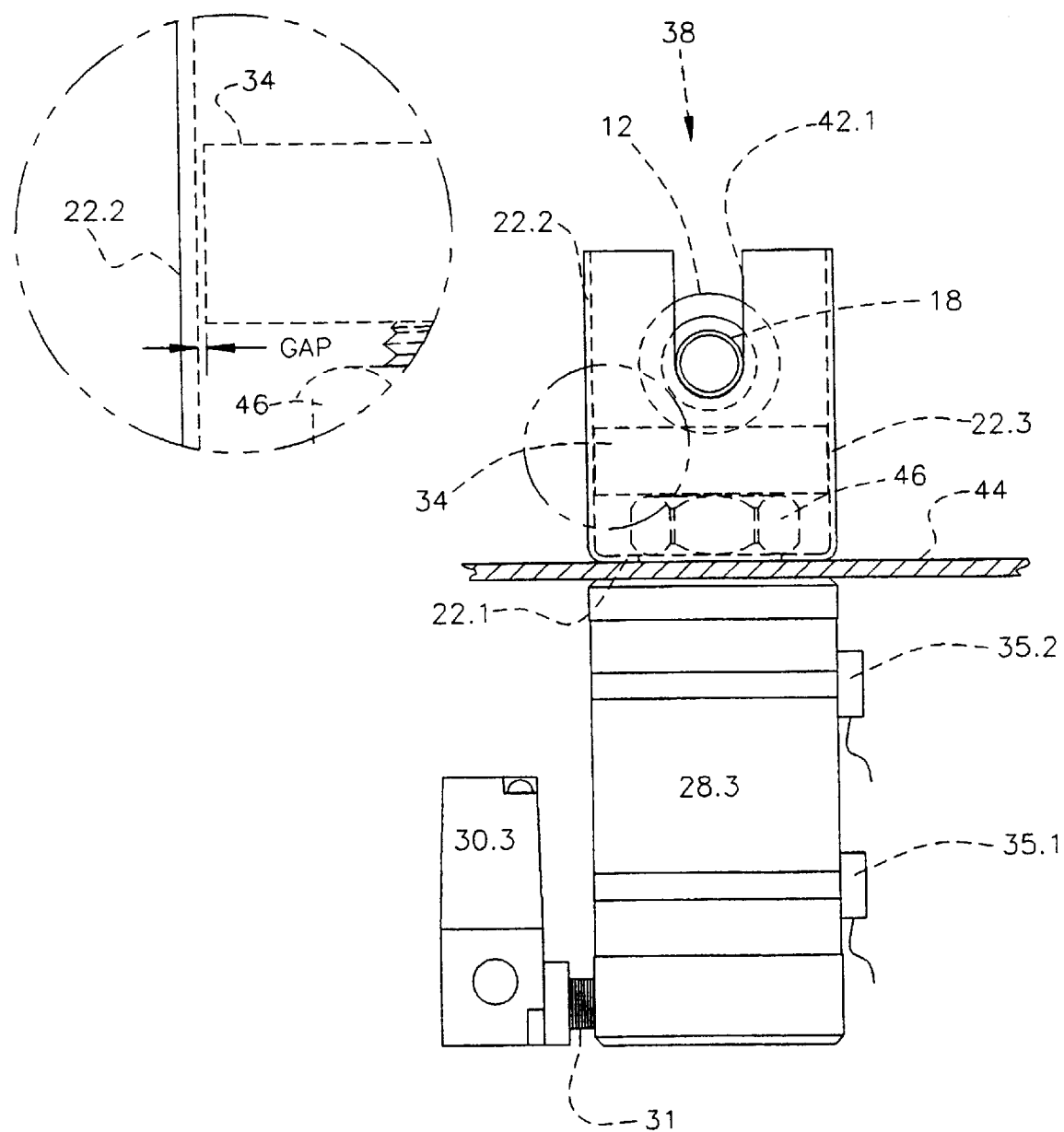
FIG. 7 is a bottom view of the pump shown in FIG. 5, parts having been eliminated for purposes of clarity.

Upon compression of the flow tube, which is complete to occlusion (wall to wall) at the IFV and OFV as shown in FIG. 5B, but may be complete or partial at the displacement element, it can be shown that relatively equal deflection occurs from each side of the tube. This is true because of the symmetry of the anvils, but also because the tube is unrestrained and free to move in the axis of compression. This means that tube compression is contributed to in a largely equal way be deflection of each opposite tube wall. Thus, for example in complete occlusion, each interior wall would contact the other near the longitudinal center line of the tube. This, in turn, greatly reduces the amount of flexure experienced by each wall of the tube as the pump is operated. This substantially reduces the repetitive stress on the tube wall and the rate and degree of compression set and fatigue the tube experiences. It can be empirically shown that this greatly reduces tube distortion and wear and thus allows greatly increased length of service life and durability of the liquid pump tube.

Another novel benefit of the symmetrical dual round anvil design is that the balanced, two-sided pump tube compression it allows causes the speed of hose recovery to be increased after complete occlusion. This follows to the fact each half of the hose must return only about one half the distance as would be the case with complete occlusion from one side of the hose as in the prior art. Another unique benefit of the symmetrical dual round anvil arrangement of the present invention is that, because it allows the tube to compress relatively equally from two sides and also allows the tube to pivot somewhat about each dual anvil engagement without pump body contact or restraint, the lever action or lifting effect upon adjacent sections of the pump tube caused by single-sided compression is substantially reduced. This, in turn, reduces these induced stresses upon the tube thus promoting longer useful life still further, but even more importantly, virtually eliminates any interaction upon other adjacent anvil compression points. This is very important to the improved control performance and predictability of performance embodied in the new design.

In linear peristaltic pumps of known type, when the pump liquid flow tube is compressed by the pump elements, the flow tube pressurizes and depressurizes, and thus expands and contracts or distends both radially and longitudinally. In these conventional designs, the flow tube rests upon a flat substrate and thus the tube motions caused by pressurization and depressurization, to significant degree, cause relative motion of the tube with the substrate. This motion induces stress, wear, and abrasion on the tube, which reduces its useful life. In the present invention, because the symmetrical dual round anvil geometry uniquely supports the tube within the pump only by the opposing anvil elements and away from the walls of the pump body, there can be no direct contact of the pump liquid flow tube with the pump body surfaces during pump operation, thus eliminating another wear mechanism upon the tube, and therefore extending pump durability and predictability of performance.

Another novel benefit of the symmetrical dual round anvil arrangement of the present invention is that it largely eliminates pump hose squirm and abrasion on the outer surface of the hose as a result of occlusive anvil action. Over time, in pumps of conventional design, the known tendency of the pump hose to be shifted or "walked" and stretched as a function of complete compression from one side of the hose can be shown to give rise to surface abrasion and cracking. It is well understood that small defects of this nature in many elastomeric materials tend to "run" or rapidly increase in depth and length once initially formed, and therefore to induce structural failure in the elastomer. Thus, by uniquely preventing the formation of such defects, the symmetrical dual round anvil arrangement of the present invention contributes substantially to the useful life of the elastomeric pump hose.

Studies conducted by way of perfecting the present invention clearly show that less force is required to collapse a high durometer elastomeric tube to occlusion with the symmetrical dual round anvil arrangement than is required to occlude the same tube placed upon a rigid flat surface and acted upon from only one side by the same actuator and anvil. This phenomenon has three fundamentally important and novel consequences relative to the pump of the present invention. First, the efficiency of the pump is directly related to the required force for desired operation. For example, in the case of the preferred method of pneumatic actuation (but not exclusive to it), the less pneumatic pressure required, the lower the net energy consumption required to gain the desired functionality. This is a means of measuring and expressing efficiency and the lower the force (pressure) required, the more efficient the pump. Second, at a given available occlusion or compression force, the force available to actually seal the occluded zone of the internal diameter of the pump hose is that remaining after the force to effect occlusion has been utilized. In effect, the differential pressure capability of an occlusion or pinch valve is largely a function of the occlusive force applied to it beyond that required for initial closure. Thus, the symmetrical dual anvil layout, because it requires less force to achieve tube occlusion, enhances the pump pressure operating capability at a given available force (pneumatic pressure in the preferred embodiment). Third, because liquid flow tube compressive forces are reduced, in any given particular preferred embodiment of the invention, a higher durometer pump flow tube can be utilized without sacrificing operating efficiency when compared to known conventional designs. As will be shown in great detail further on, the ability of the present invention to allow the use of a very stiff walled pump tube imparts unique and important capabilities to the pump of this invention.

THIRD NOVEL FEATURE

The third novel and unique feature of the present invention is derived from the design of the actuator-anvil element such that the square area of pressure acting upon the actuator (typically the piston of a pneumatic cylinder) is always substantially greater than the square area of the anvil acting upon the liquid flow tube. This will be referred to herein as force multiplication. As will be seen, force multiplication allows pressure multiplication which yields high pump discharge pressure capability.

As earlier stated, it is a primary objective of the present invention to provide a linear peristaltic pump which is capable of pumping at high discharge pressures. To be capable of such performance, the force acting upon the displacement element of the pump must be very high, as well as upon the occlusive valves IFV and OFV. In the present invention, air cylinders are used to urge the anvils 34 upon the pump hose 12. In the use of such pneumatic cylinders it is well understood that the force available at the rod of the cylinder is simply the square area of the piston in the cylinder multiplied by the gas pressure applied against the piston. Thus, by example, a 1.50 inch bore pneumatic cylinder has a piston area of 1.77 square inches. If 60 pounds per square inch of gas pressure is applied to this cylinder it will generate 106 pounds of force. If the anvil acted upon by the actuator has a square area acting upon the pump liquid flow tube of 0.75 square inches, in the worst case, then the 106 pounds of available force generates a pressure at the anvil of 141 pounds per square inch. Thus, by this method, it is possible to bring to bear on the flow tube of the pump a force sufficient to generate a high pump discharge pressure using a modest and practical actuating pressure. This method overcomes the pressure capability limitations of 3 element linear peristaltic pumps as known in the prior art. The particular unique and important advantages of this method of generating the high forces needed for high pump discharge pressures include the ability to continuously apply the desired force to the occlusive valve positions and to the compressive or occlusive displacement position as necessary, and regardless of variations in flow tube wall thickness from specimen to specimen or over time. It is important to understand that the wall thickness of the flow tube, types which will be described for use in the pump of the present invention, can vary substantially from one manufactured lot to another. Further, it is well known and understood that a flexible tube acted upon by repeated compressive occlusion will be measurably reduced in wall thickness over its cycle life. By particular design of the present invention, the pneumatic cylinders are constructed to assure that their stroke exceeds that required to actually occlude the flow tube. Because of this overtravel capability, the tube compression anvils, one from each side in each location, can continue to apply a defined and known force over a defined area of the tube wall regardless of variation in the required actuation distance to do so. This also uniquely allows the user of the pump to freely interchange or replace pump flow tubes regardless of life cycle effects or significant manufacturing lot dimensional variations. Further, because of this overtravel design, the ability to readily and inexpensively control the total force applied and thus the discharge pressure of the pump is precisely available as a function of gas pressure adjustment to the linear actuator. This is more fully explained further on.

In some prior art, in-line peristaltic pumps, it is conceivable to generate high anvil compression force using a cam driven system. However, because in such designs the cam profile defines the stroke distance as well, the necessary overtravel for occlusive valve service cannot be derived in an automatically variable manner as is clearly essential for high force and high pressure operation. The use of hydraulic valves and cylinders is also conceivable, but these devices are much more costly and typically operate properly and efficiently only at pressures much too high for the purposes of the present invention. In addition, they require an expensive hydraulic fluid power source which is much less commonly available, understood, or accepted in many likely uses of the pump. Direct application of hydraulic force upon the liquid pump hose is known in the prior art but is very difficult to control in practical terms and the fear of penetration of the working hydraulic fluid into the lumen of the liquid pump hose prevents general or critical use. In a few prior art designs, the use of springs to compress the liquid flow tube is known. Cams are used to remove the compressive elements from the tube. This method allows overcompression of the flow tube with varying stroke distance requirements as is necessary for high pressure operation, but the force generated by a spring is know to vary significantly one from the next, and to vary greatly over the life of the spring, particularly with repeated compression and relaxation. It is also difficult to variably adjust such springs to achieve a particular force and to match such a force to that applied by other compressive spring elements in the same pump. Adjustment is even more difficult and costly when applied forces can be in the many hundreds or thousands of pounds as contemplated and achieved in the present invention.

FOURTH NOVEL FEATURE

The fourth novel and unique feature of the three element linear peristaltic pump of the present invention is the use of a thick walled, multi-layer, laminated, compound reinforced, high durometer, high pressure rated liquid pump tube. The unique design elements of the present invention, particularly the method of construction, the symmetrical dual anvils, and the force multiplication actuator-anvil geometry allows high force to be brought to bear upon the pump flow tube 12. Because this is the case, the flow tube can be constructed in such a way as to benefit the high viscosity and high pressure design objectives of the invention. In any three element linear peristaltic pump design, when the back pressure acting on the pump or the feed pressure applied to the pump approaches or exceeds that required to cause distortion or swelling of the flow tube, pump operation can be adversely affected. In the case of back pressure, the compressive action of the pump displacement element will result in deformation or bulging of the tube wall, also referred to as distension. It is to be particularly understood that when the flow tube distortion occurs due to a pump back pressure which is too high, pumping is disrupted. The displaced volume may decrease substantially or even be reduced to zero. When partial pumping does occur, the displaced volume from cycle is unpredictable due to the variable ballooning of the tube as it is partially relieved and re-inflated. There is also the risk that the pump flow tube will rupture due to excess pressure. It is also to be particularly noted that the high pressure can be applied to the pump from the infeed side. When this pressure is high enough to cause flow tube distension, the IFV and displacement sections of the pump tube can swell, and pumping becomes indeterminate. In this instance, the risk of pump flow tube rupture is also present. Because of many other design considerations which are extensively discussed in the prior art, the liquid flow tube used in known linear peristaltic pumps is generally a single walled, homogeneous elastomeric material. Tubes of such construction, even when thick walled, are rarely capable of sustained pressurization above 25 to 30 pounds per square inch without substantial distension. Accordingly, the discharge pressure (otherwise referred to as back pressure) capability of in-line peristaltic pumps designed with such tubing are similarly constrained.

In the pump of the present invention the liquid flow tube is a thick walled tube as can be seen from FIG. 5. The tube is typically constructed such that the inner lumen layer is a smooth elastomer, such as silicone rubber, which is laminated with four plies of fiber reinforcement, such as Nomex®, the fiber reinforcement being alternated with additional layers of silicone rubber, and the outer surface is also a layer of silicone rubber. The reinforcing fibers are applied in a spiral manner with each layer alternating in direction. This construction is illustrated in the cutaway view of the hose shown in FIG. 8A. Thus, an inner lay of silicone rubber 12.1 is spirally wrapped with a first layer of Nomex® aramid fiber reinforcement 12.2 embedded in silicone. Another layer of Nomex® 12.3 embedded in silicone is then spirally wrapped in another direction. Further layers 12.4 and 12.5 of Nomex® embedded in silicone are then applied, and then a final silicone sheath 12.6 is applied, completing the tube. An example of a hose of this construction and suitable for use in the present invention is known as SMP series hose as manufactured by Pure Fit, Inc. of Allentown, Pa. (While aramid fibers and silicone rubber have been described above, other suitable fibers or rubbers may be employed in the manufacture of suitable tubes.) The result of such tube construction is seen in the case of a pump tube with a nominal internal diameter of 0.625 inches, which has a minimum burst pressure of 500 pounds per square inch and an extremely high durometer with the ability to withstand high pressures without significant radial or longitudinal swelling or distortion. The result of this tube construction is a pump hose that requires substantial force to compress and seal, (in the range of 68 pounds for a pump tube with a nominal internal diameter of 0.625 inches), but uniquely offers a means of achieving pumping performance across a very high pressure range, low to high, with the pressure being applied to either the infeed or outfeed of the pump.

Another benefit of the novel use of a high pressure pump liquid flow hose is the long term service and stability and predictability of pumping performance it affords. This is true particularly because the use of the symmetrical anvil arrangement affords the balanced pressure, minimal flexure motion benefits previously described, but also because the multi-layer laminated wall tube affords long term compression and occlusion capability without the substantial compression set or elastomeric fatigue observed in flow tube-pump combinations of previously known in-line type. It is well understood that a primary fatigue phenomenon associated with known peristaltic pump-tube combinations is the progressive reduction in suction or priming capability as the tube wears, fatigues, or sets. This problem is nearly completely avoided by use of high pressure pump tubing.

The use of a thick walled, high durometer liquid pump tube confers still another novel advantage to the design of the pump of the present invention, namely, a significant increase in cycle speed capability of the pump as a function of the very high rebound force of the tube following compression. The use of smooth, single walled flexible pump tube rebound as the return force for the actuators is not unknown in the prior art. However, it can be shown empirically that the laminated, extremely stiff wall construction of the pump tube utilized in the present invention greatly increases rebound force and thus reduces rebound time. This allows reduced times for actuator return motions and, thus, faster pump cycle times. Further, there is a much reduced loss in this rebound force over the useful life of the pump tube when compared to that of single layer flexible tubes used in the prior art. The elastomeric return spring effect is therefore more robust and long lasting and is restored completely with each replacement of the tubing.

FIFTH NOVEL FEATURE

The fifth novel feature of the three element linear peristaltic pump of the present invention is the use of pressure rings in conjunction with the pump tube.

As previously discussed, the use of a pump tube of reinforced construction allows high pressure containment and, in conjunction with the particular methods of construction of the pump, high pressure operation. The use of pump pressure rings further enhances this capability.

Pump tube pressure rings 52, which could also be termed pressure containment rings, consist of rigid rings or cylinders with an internal diameter only slightly greater than the outside diameter of the pump tubing. They are typically constructed of rigid material such as plastic or metal. In a three element in-line peristaltic pump of the present invention, where the displacement section consists of only one actuator, two pressure rings are placed over the tubing and positioned, respectively between the infeed valve anvils and the displacement anvils, and between the outfeed valve anvils and the displacement anvils. In embodiments where there is more than one displacement actuator, a pressure ring is also installed between each adjacent anvil position. The pressure rings typically slide freely over the tubing, the internal diameter of the rings being slightly greater than the outside diameter of the pump tube. Once positioned on the tube as described, the rings show no tendency to move, being symmetrically trapped and self centered between adjoining anvil locations. It is possible to affix the rings into position on the pump tube using mechanical or adhesive means, but this is done only as an assembly convenience and is not functionally necessary.

These simple devices serve two principal roles in the pump of the present invention. First, the rigid rings contain the tube wall which they surround, thus further limiting pressure mediated, radial distension or swelling of the pump tube during high pressure pumping. This enhanced containment increases the volumetric displacement of the pump with each complete pumping sequence, which is advantageous to the economy and efficiency of the device. This increase in flow as a result of the use of pressure rings can be empirically demonstrated by operating the pump of the present invention for a defined number of pumping cycles and measuring the displaced volume, first without pressure rings fitted to the pump tube, and again with pressure rings installed.

The total volume displaced with pressure rings in use significantly exceeds that displaced when pressure rings are not utilized.

The second major role of the pressure rings is to cause faster restoration or rebound of the pump tube to a round or uncompressed shape after compression. This speed up occurs as a function of the circular boundary which is established and maintained by the ring structure. In effect, as the tube cross section deforms with compression, the ring stops the tube from deforming beyond the edge of the ring. This has the effect of maintaining more elastomeric rebound force closer to the point of compression than would otherwise be the case.

This speed up tube opening after compression has beneficial effects on each of the three major pump elements. Faster opening speed of the pump tube at the IFV and displacement section improves the pumps priming performance substantially both by virtue of the speed increase itself, and by reducing and offsetting any long term effects of tube rebound fatigue and compression set with repeated flexure. The OFV is similarly accelerated in its restoration or rebound after occlusion. This allows a shorter OFV pre-open time prior to the compression of the displacement section, thereby allowing the pump to cycle faster. Thus, overall, the use of pressure rings results in greater displacement per pump cycle, and fast pump cycle times. Both benefits therefore sum to increase the flow rate capability of the pump. Further, pressure rings contribute favorably to the long term stability of performance of the pump, which is a primary object of this invention.

SIXTH NOVEL FEATURE

Figure 8:
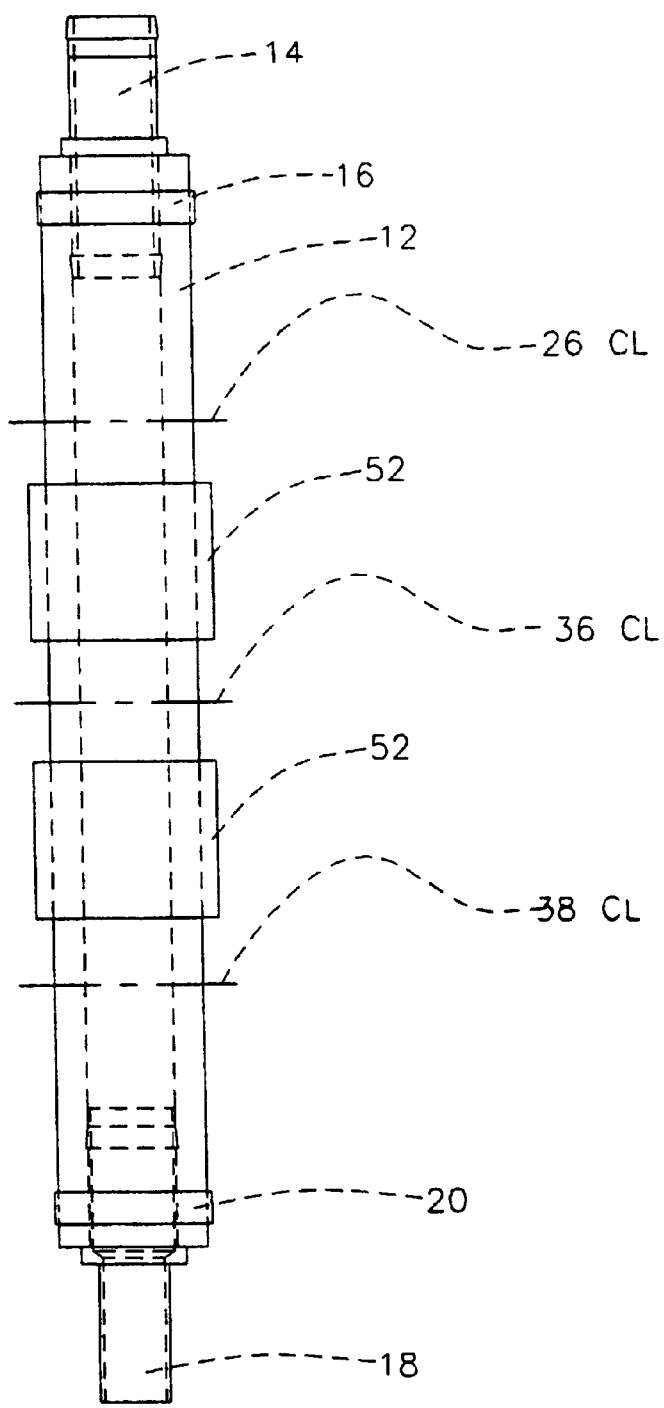
FIG. 8 is an enlarged detail view of a portion of the pump shown in FIGS. 4 and 5.
Figure 8A:
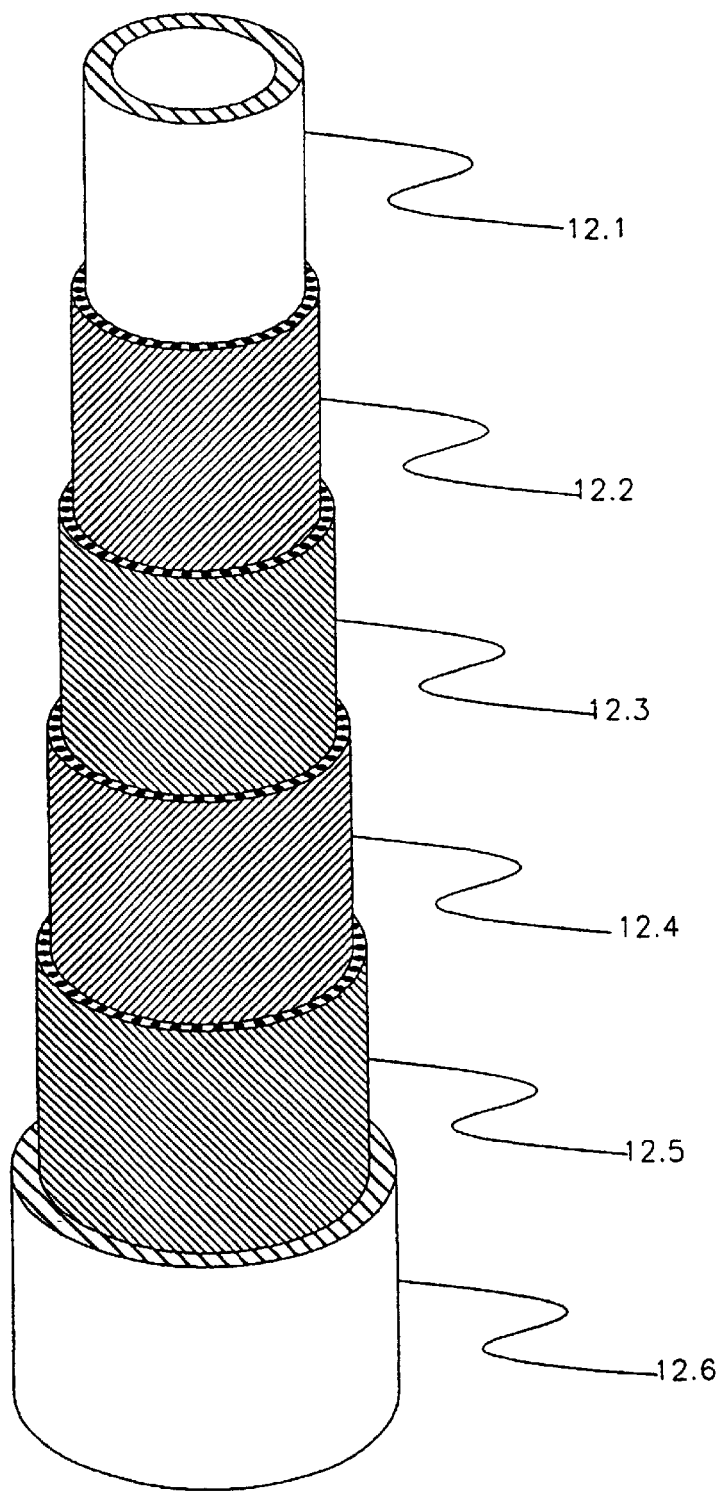
FIG. 8A is a cutaway view of the pump tube employed in the pump of this invention.
Figure 11:
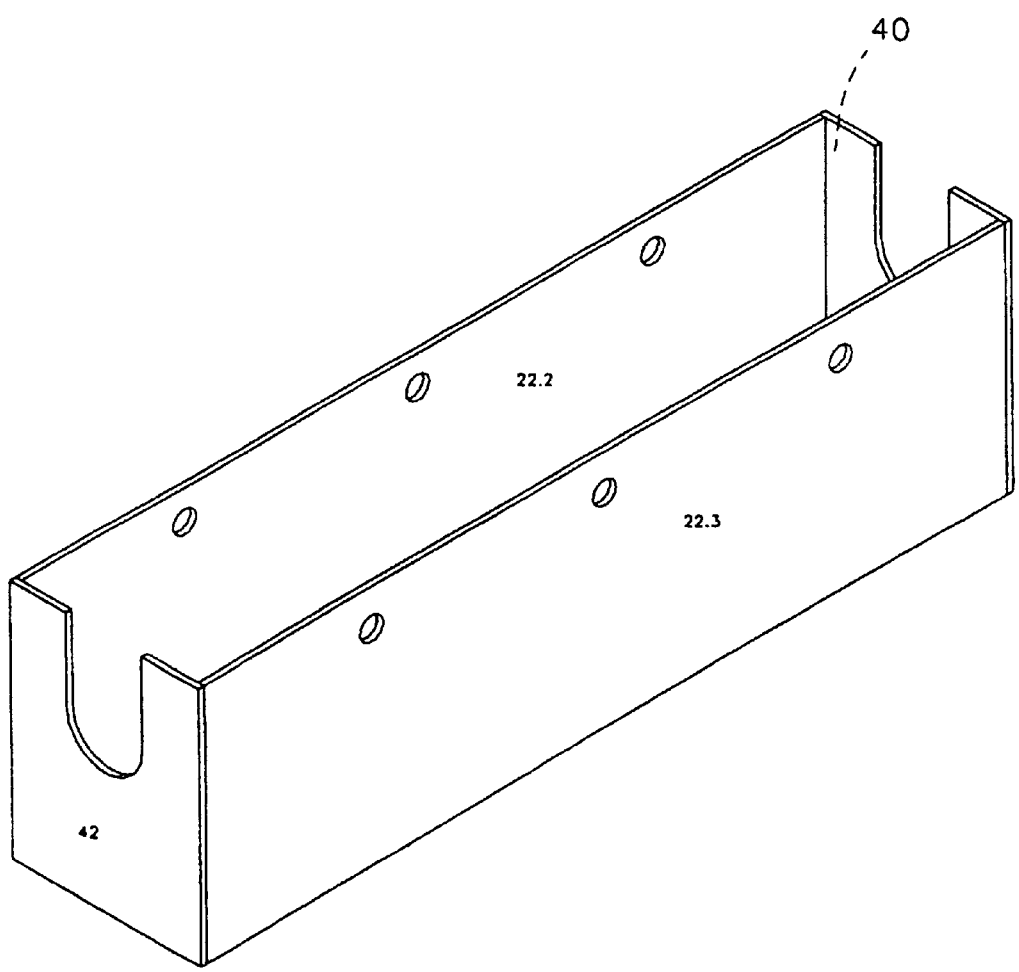
FIG. 11 is a isometric view of the U-shaped pump housing or channel member which receives the portion of the pump shown in FIG. 8.

The sixth novel feature of the three element linear peristaltic pump of the present invention is the positioning of the internal shank of the two pump tube end fittings 14, 18 such that each ends within a defined distance d of the center line of its respective anvil pair, the center lines being shown in FIG. 8 at 26CL, 36CL, and 38CL. This defined distance is the product of the internal diameter of the flow tube multiplied by any number between 1.20 and 2.00. This geometry is best illustrated in FIG. 5 wherein the defined distance "dd"

is between 1.2 to 2.0 times greater than the internal tube diameter "id". When this geometry is established, it can be shown empirically that a faster restoration or rebound of the pump tube to its uncompressed shape occurs after a compression event. The mechanism of this speed increase is akin to that previously described for the use of pressure rings, and the benefit is an increase in the flow rate of the pump as well as a reduction in the long term rebound fatigue effects associated with repeated tube flexure.

SEVENTH NOVEL FEATURE

The seventh unique feature of the three element linear peristaltic pump of the present invention is the use of an actuator for the implementation of the infeed valve (IFV) of the pump which acts with higher force than that used for the displacement and outfeed valve (OFV) elements.

In the pump of the present invention, the IFV must withstand the highest differential pressure of the three primary pump elements. This is the case because, when the OFV is open and the displacement section is not occluded, the IFV is exposed to the entire system pressure and in addition the valve is acted upon by the instantaneous pressure excursion which is created locally within the pump when displacement compression occurs. These two pressures are additive and represent the highest pressure condition to which the pump can be subjected. It will be understood that by the nature of the design of the infeed and outfeed valve elements, liquid pressure applied to either side of the occluded valves will act against the applied occlusive force. Thus both the IFV and OFV elements of the pump are, by design, capable of withstanding a finite cumulative liquid pressure while remaining free of liquid leakage across the valve.

To clarify the phenomenon by which the IFV is exposed to a higher total pressure than the rest of the system, recall that with the OFV open, and the displacement section uncompressed, the IFV is exposed to the entire pressure across the pump. Under these conditions the rapid compression of the pump displacement section can result in a rapid pressure excursion on the discharge side of the IFV which can raise the differential pressure above that which the IFV can seal against, resulting in lifting of the valve, loss of occlusion, and thus forced leakage of liquid across the valve, typically from the discharge side of the valve toward the infeed side. The rapid pressure excursion or pressure spike can occur because there is a latency to flow imposed by the discharge pressure and flow resistance of the pumped liquid, particularly as a function of liquid viscosity and discharge plumbing to which the pump is fitted. Thus, until discharge flow occurs to such a degree as to relieve this pump displacement pressure, the pressure at the IFV builds, and may exceed the occlusive seal force capability supplied by the IFV actuator.

These described pressure phenomenon can be experimentally demonstrated. When such IFV valve leakage is induced, it can be shown that the displaced volume per pump cycle is reduced. To overcome this problem of IFV leakage, even when the static differential pressure across the pump is below the leakage pressure of the pump valves, the pump of the present invention uses a pneumatic actuator to implement the IFV function which is larger in square area than those used in the displacement and OFV locations. The use of a larger square area actuator allows a single gas pressure, in the preferred embodiment, to be used at all actuator positions within the pump. This is the simplest and most economical means to achieve a higher force IFV valve and it assures a specified and fixed force relationship among the actuators regardless of the applied gas pressure. Thus, for example, one embodiment of this invention uses air cylinder actuators for the displacement section and the OFV which are 1.5 inches in diameter, while the IFV air cylinder actuator is 1.75 inches in diameter. This results in thirty-six percent more force applied by the IFV cylinder at any given gas pressure. It is possible to use an actuator in the IFV position which is of the same size as used for the displacement and OFV elements and apply a higher gas pressure to the IFV cylinder for higher force. However, the fixed force relationship is lost and the system becomes more complex.

EIGHTH NOVEL FEATURE

The eighth unique feature of the three element linear peristaltic pump of the present invention is the ability to incrementally add pump displacement actuator modules to increase liquid flow rate per pump cycle without the loss of pump discharge pressure capability, and without significant increase to pump cycle time.

It is possible to increase the displaced volume per pump cycle in a linear peristaltic pump of given pump hose size by increasing the square area of pump hose which is compressed by the pump displacement element. However, unless additional compressive force is supplied to the displacement element which is proportional to its increased area, the discharge pressure capability of the pump is impaired. It is impractical within the scope of known designs of linear peristaltic pumps to readily alter the square area of the displacement element and automatically alter actuator drive force as a function of a change in the compressed area of the pump hose in order to hold pump output pressure capability constant. The pump of the present invention provides means to do both.

Figure 13:
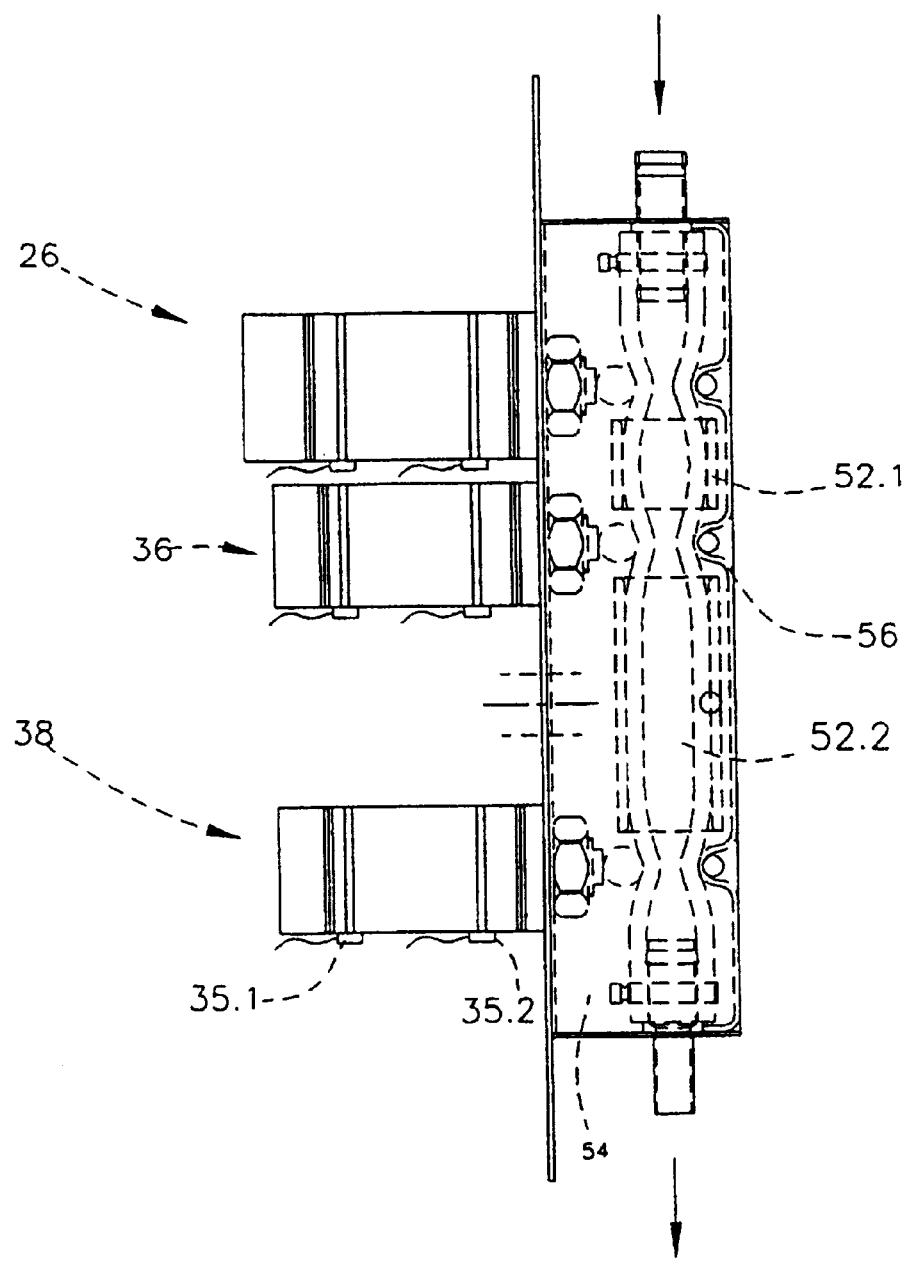
FIGS. 13 and 13A are views similar to FIGS. 5 and 6 but illustrate a pump which may receive an additional linear displacement actuator.
Figure 14:
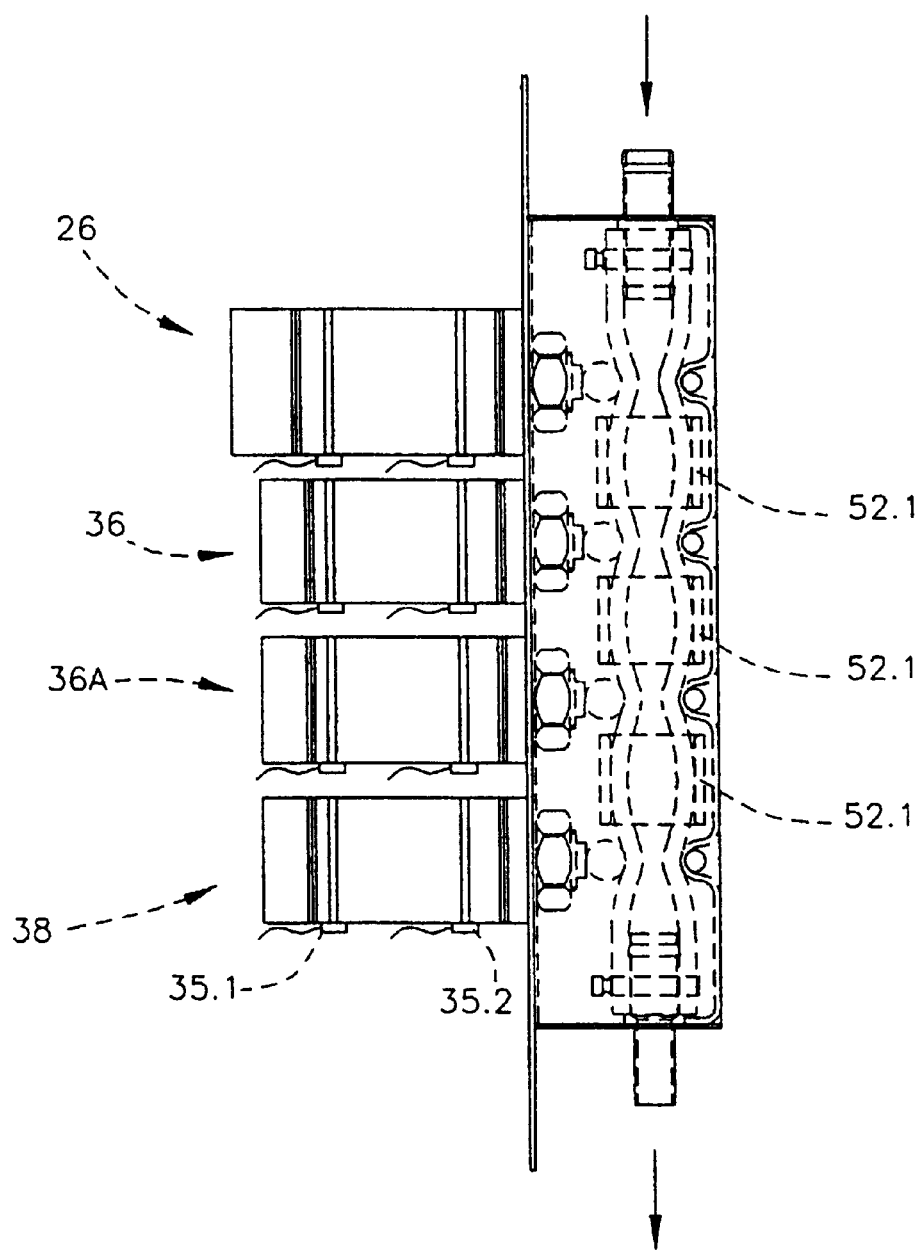
FIGS. 14 and 14A are views similar to FIGS. 13 and 13A but shown an additional displacement actuator mounted upon the pump.
Figure 14A:
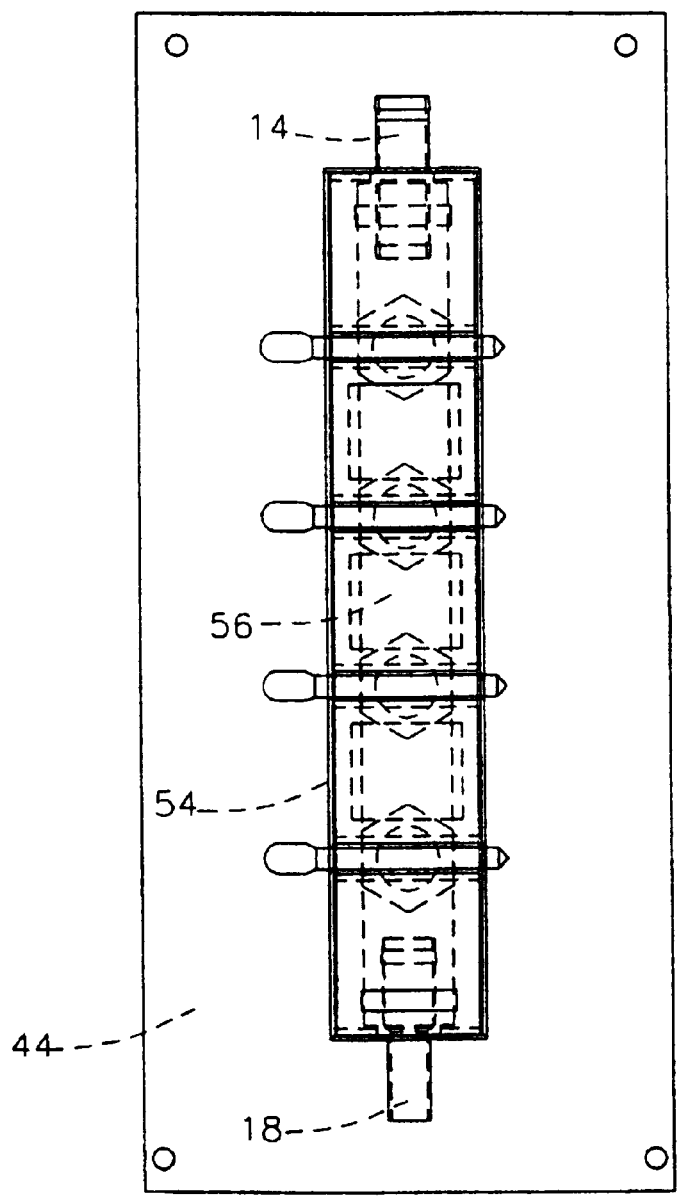

With reference to FIGS. 13–14A, the displacement of the pump per cycle of operation may be incrementally increased by the addition of a complete displacement apparatus. This includes the addition of an actuator, the symmetrical anvils and the solenoid valve associated with the actuator. By such addition, the displacement of the pump is altered in a completely known and predictable manner and the pump pressure capability is unaltered. This is true because each actuator in the pump has a defined compressive force per unit of compression area acting upon the pump tube. Therefore, the incremental addition to the pump of a complete displacement actuator adds a defined additional pump tube compression area at a defined compressive force, without having any effect upon the pump tube compressive force of any other actuator in the pump.

In other words, a pump of this invention can be designed in such a manner as to allow the incremental addition (or deletion) of compressive elements as desired, in a preplanned manner wherein the pump is manufactured with provision for such changes to be easily and quickly made at the site of pump usage.

Figure 13A:
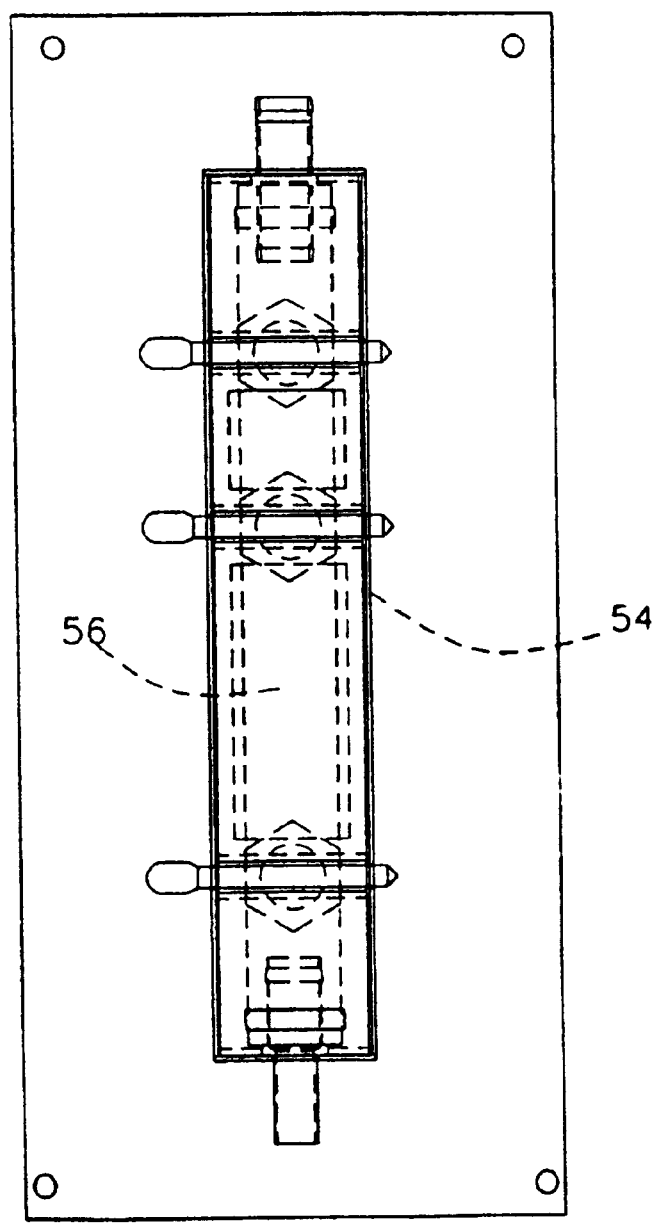

With reference to FIGS. 13 and 13A, a pump of the present invention is designed for the modular addition of compressive elements, and these elements are not fitted to the pump as shown in these figures. Thus, a longer U-shaped support channel 54 and a longer anvil plate 56 are provided. The length of the channel 54 and anvil 56 is such that it may receive an IFV 26 and OFV 38, and two displacement assemblies 36. However, as shown in FIGS. 13 and 13A, only one displacement assembly may be provided. In this design, the liquid flow tube is provided with pressure rings (the nature of which has been previously described), of sufficient length to span most of the interval between adjoining anvil locations. Thus, there is a pressure ring 52.1 of a standard length, and a long pressure ring 52.2. This assures radial pressure containment performance of the pump tube. As shown in FIGS. 14–14A, an additional compressive element 36A is fitted to the pump, two additional pressure rings 52.1 of suitable length are provided to correctly span the altered interval between adjoining anvil locations.

Figure 15A:
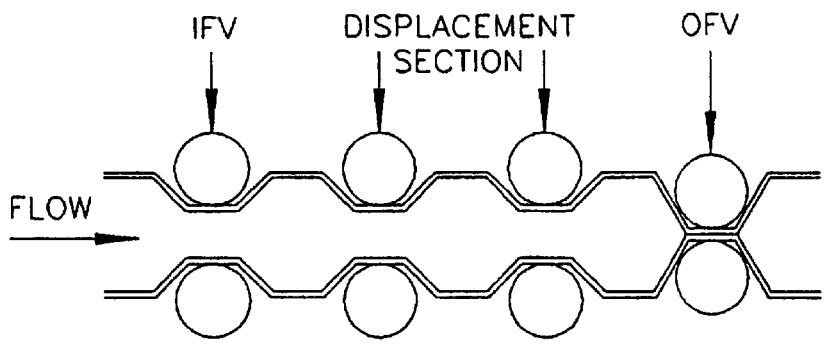
Figure 15B:
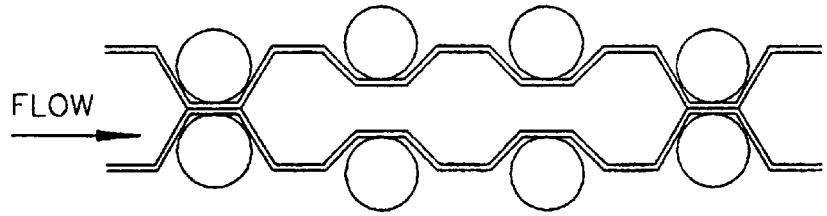
Figure 15C:
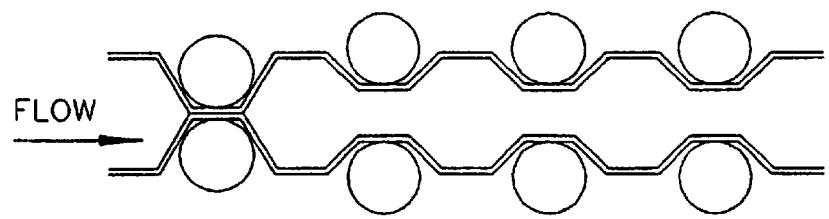
Figure 15D:
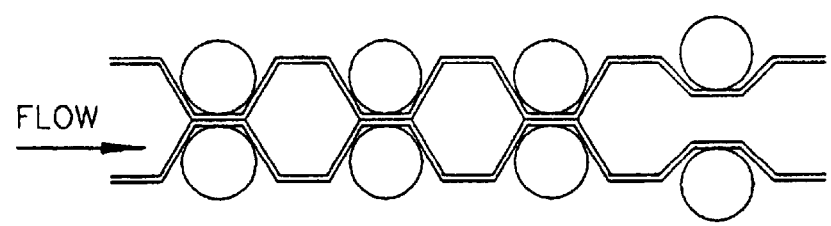
Figure 15E:
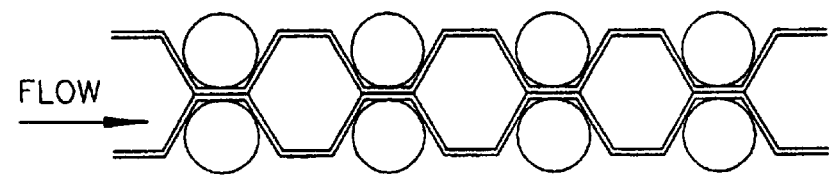
Figure 15F:
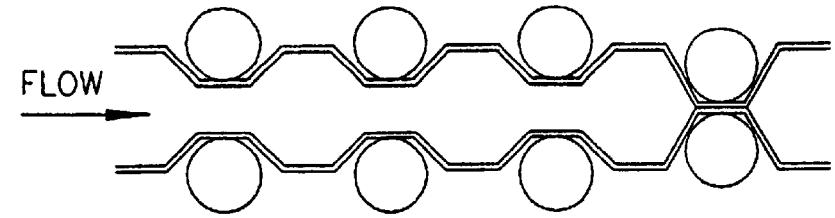
Figure 18A:
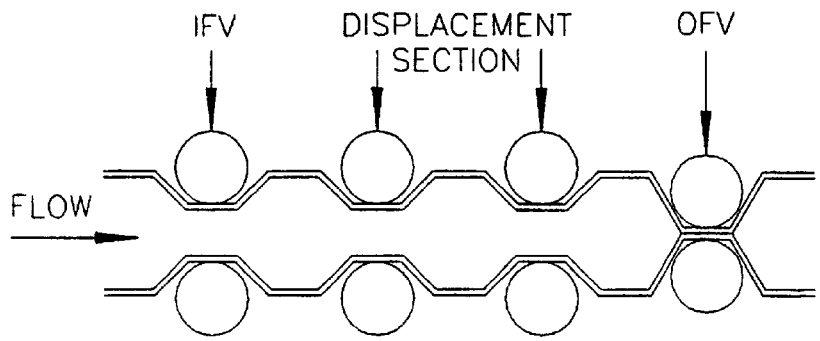
Figure 18B:
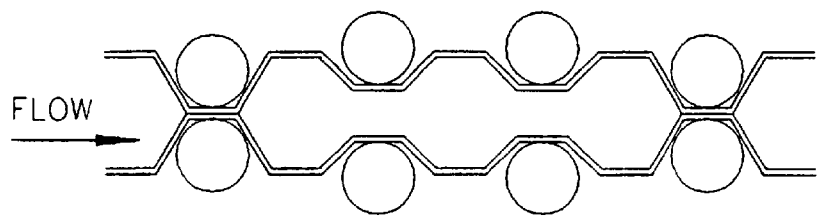
Figure 18C:
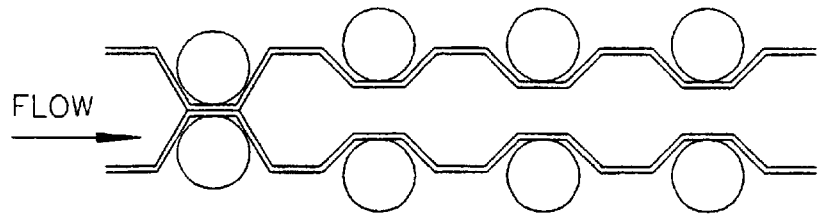
Figure 18D:
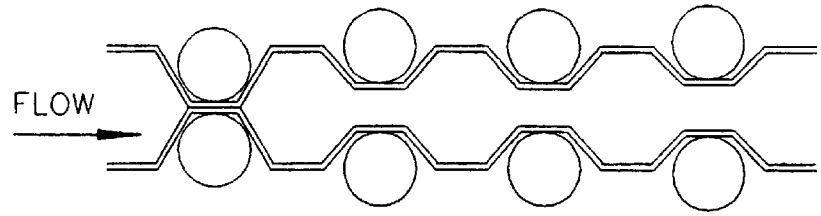
Figure 18E:
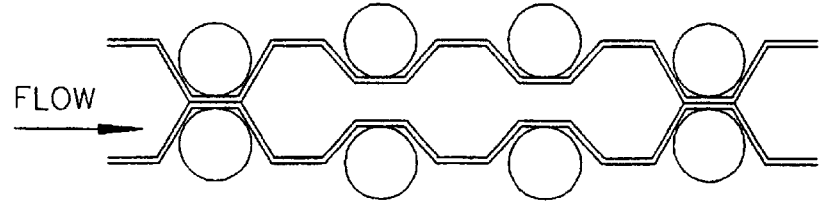
Figure 18F:
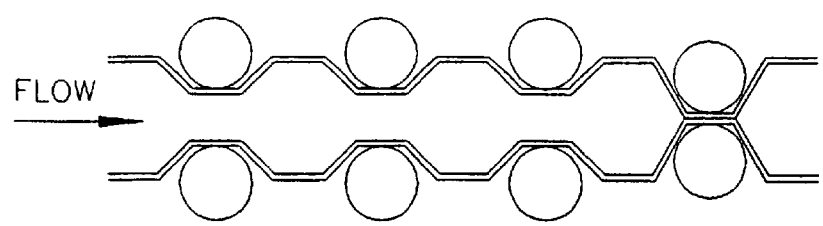
Figure 24:
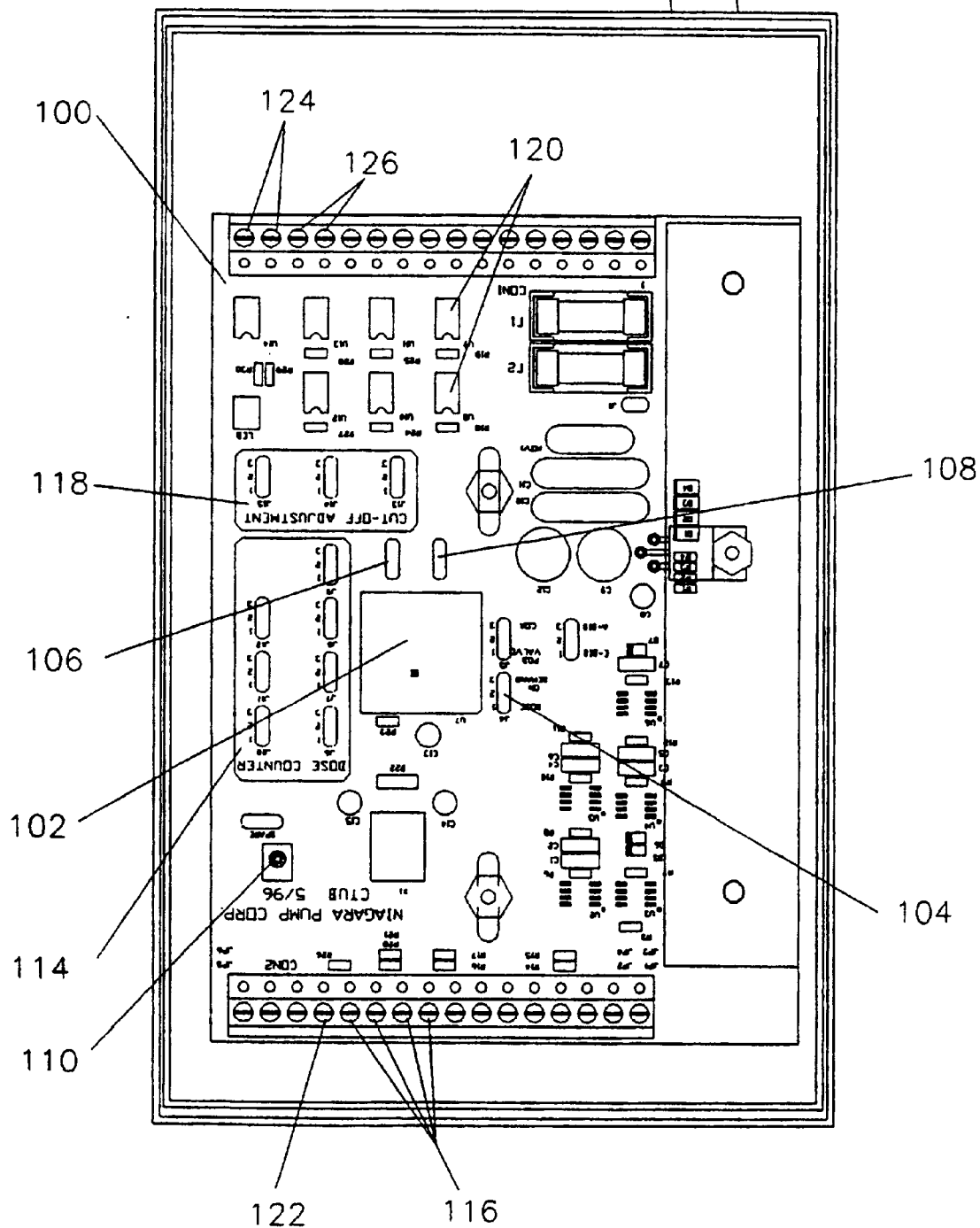
FIG. 24 is an enlarged view of the electronic control module.

When multiple compressive elements are fitted as shown in FIGS. 14 and 14A, the sequence of actuation of these elements must be considered. Pneumatic cylinders, each equipped with its own solenoid valve, are utilized as actuators. Thus, with the addition of displacement actuators, such that there are more than one in the pump, each can be discretely addressed and initiated by the pump's control electronics (FIG. 24). Accordingly, in the sequencing of the pump, when the displacement compression step arrives, each actuator can simply be actuated simultaneously as shown in FIG. 15D. Operation of the cylinders 28 is controlled by an electronic module 100. Where the displacement actuators 36, 36A are simultaneously actuated to compress the tubing completely to occlusion, increased displacement is achieved, as is desired. The intervening volume of liquid between adjacent actuators 36, 36A which is a function of the dual symmetrical anvil-force multiplication design, is not a functional problem in that as long as the displacement actuator 36A, which is closest to the outfeed valve of the pump, remains open, so that flow from the entire compressive section can continue. This flow is essentially hydraulic and thus the liquid flow tube lumen between adjacent displacement elements is irrelevant. Indeed, the flow during compression of the displacement elements is akin to that which would be derived from the displacement caused by a single continuous compressive element, such as a flat plate, wherein the direction of flow is entirely from the displacement lumen to the outfeed of the pump, and the relative velocity of the flow past the adjacent compressing tube walls generally increases as the dimension between them decreases. However, one skilled in the art will understand that with the use of discrete pneumatic actuators, it is possible for one such device to be slightly slower or faster than another of the same design and specification. This difference in speed is a function of normal manufacturing tolerances. Normal wear of the actuators will also cause changes in the speed of operation. When this expected variation in actuator speed results in the occlusion of the displacement actuator closest to the outfeed valve ahead of the other actuators, displaced flow can be cut off prior to completion of liquid displacement by the other actuator. This is an undesirable condition. There are two unique and preferred methods which can be utilized in the present invention to overcome this problem.

Figure 26:
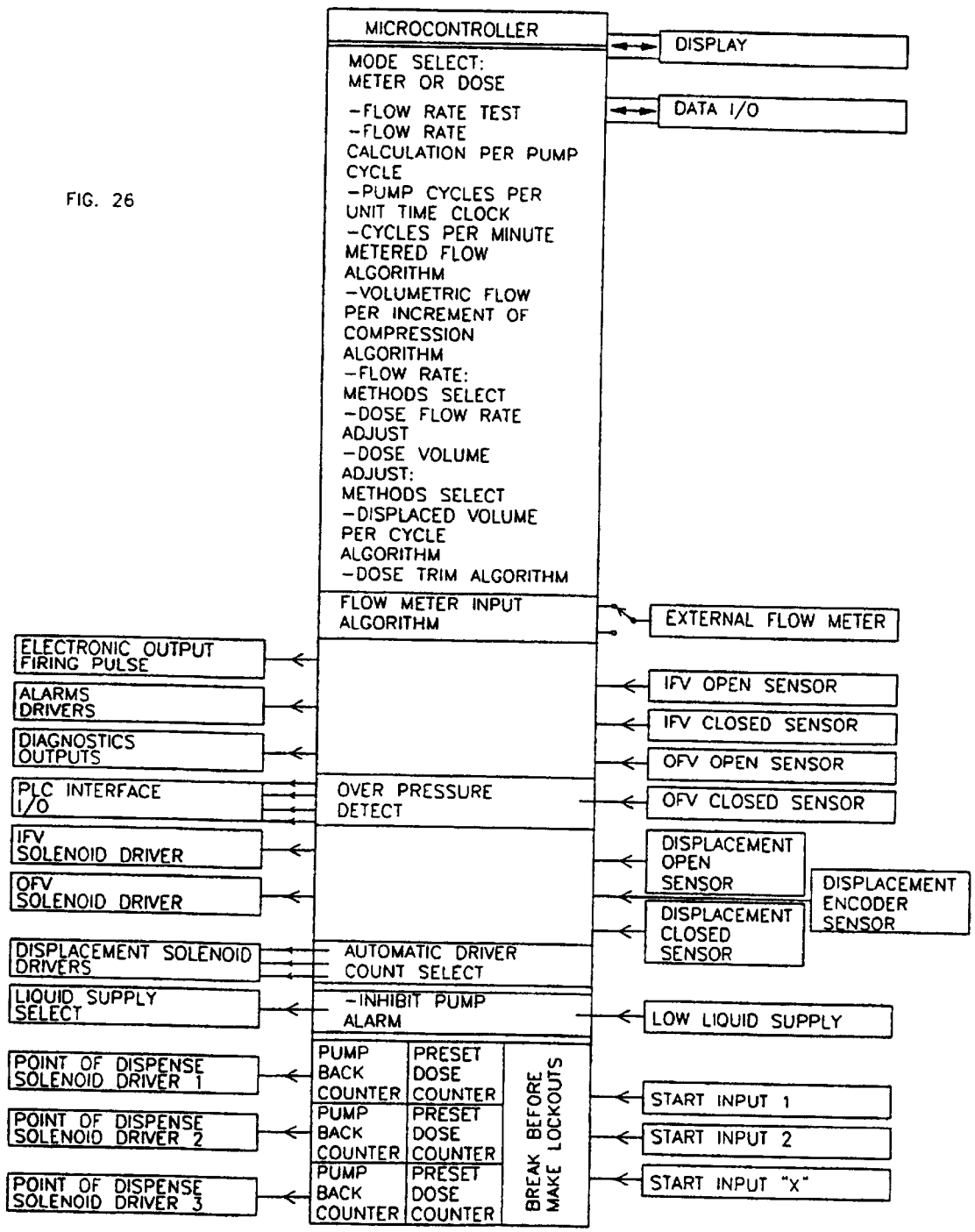
FIG. 26 is a chart of the implementation of the microcontroller.

In the first preferred method, which may be referred to as the sequential complete occlusion actuation method, each displacement actuator is still allowed to completely occlude the pump tube as initially described. This method is illustrated in FIGS. 16A to 16G. FIG. 16A shows the normal "at rest" position where the tube at the OFV 38 is closed, the tube 12 contacted by the anvils of other actuators 26, 36, 36A being open. The sequential operation of the actuators is illustrated in FIGS. 16A to 16G and is electronically altered such that at the displacement steps shown in FIGS. 16D and 16E in the pump sequence, the cylinder of actuator 36 closest to the IFV is actuated first, followed by the cylinder of the next adjacent actuator 36A. This sub-sequence of actuation assures that no displacement actuation can block the flow of any similar actuator located between it and the infeed valve of the pump. The delay time interposed between each actuation may be fixed and pre-determined, in which case the time is only a fraction of the typical actuator travel time from open to occluded. There is no need to establish a longer delay time between successive actuations, or even one establishing a complete sequential separation of displacement actuators, since the objective of the delay in this method is only to assure that the displacement actuator closest to the OFV does not close or occlude ahead of the others in the pump. This delay time may be selected by the electronic control system 100 of the pump as displacement actuators are added. For example, using a microcontroller 102, a series of inputs to the controller can read a binary number which signifies the number of displacement actuators in service in the pump, the number being set by a manual input device (FIG. 26). The required actuation delay items may then be automatically inserted into the sequence, as well as the necessary valve drives. In an even more automated version, the actuation delay times and valve drives may be inserted into the sequencing by galvanically detecting the installation of valve coils into the electronics system. In a more sophisticated version of the pump of this invention, the actuators in all positions are encoded such that end of travel sensors 35.1 and 35.2 on each actuator detect the fully open and fully occluded positions of the actuator, respectively. The particular advantages and benefits of this encoding will be extensively detailed further on. In a discussion of a first method of proper sequencing of multiple displacement actuators, the encoding of these actuators provides optimum adjustment, on an automatic basis. When operated with this configuration, the loss of signal from the open sensor fitted to the displacement actuator closest to the IFV causes the next displacement actuator to begin motion, which, in turn, causes the next to sequence, and so on. In effect, the delay time between actuations is closed loop and as minimal as possible. This variation of the first method of preventing displacement flow cut-off due to early closing of the pumping actuator closest to the OFV assures proper sequencing even when the actuation times of the elements change.

There is a special case of the sequential-complete occlusion method where a complete sequential separation of displacement actuators is favored. This occurs when the pump of the present invention is to pump liquids with large entrained solids or particulates or inclusions. Under these circumstances, the sequential movement of these inclusions, from a first displacement actuator closest to the IFV, to a second and so on, is best managed by allowing complete occlusion of each actuator in turn, before the next begins compressive movement. It is within the scope of the control electronics of the present invention to provide for a microcontroller input which serves as a selection function for pumping non-homogeneous liquids. When so selected, a sequence time long enough to assure complete overlap of displacement actuations can be defined, or, in the subcase of encoded actuators, the actuation of each displacement cylinder can be dependent upon the completion of compression of the previous one, as determined by the end of stroke sensors 35.2 on each cylinder.

In the second preferred method of actuating multiple displacement actuators, in order to prevent displacement flow cut-off due to early occlusion of the pumping actuator closest to the OFV, the problem is avoided by assuring that only the displacement element closest to the IFV can travel a sufficient distance to actually occlude the tubing, while all subsequent displacement actuators do not have sufficient mechanical stroke length to achieve complete liquid flow tube occlusion. This is illustrated in FIGS. 17A–17F. In a variation on this approach, all of the displacement actuators can be designed with stroke lengths which are equal and insufficient to allow complete occlusion of the pump tube as illustrated in FIGS. 18A–18F. Either variation allows simultaneous actuation and compression of all displacement actuators in the pump. This is the case because with this method it is not possible to trap or block the flow of any of the displacement actuators. This method is simple and effective but requires several evident compromises. Because complete tube occlusion is for the most part not allowed, displaced volume per displacement compression is reduced.

Thus, additive actuators provide a reduced volumetric increase in the case where the first displacement actuator is occlusive, but all other displacement actuators are not. In the case of non-occlusive compression in all displacement locations, pump volume per cycle is lessened in all configurations as compared to the complete occlusion methods. Furthermore, non-homogeneous liquids containing relatively large particulates or inclusions are not generally as well handled by the pump using this method, particularly from the perspective of the amount of degradation or size and shape reduction and change caused to the inclusions by the pumping action.

Figure 19:
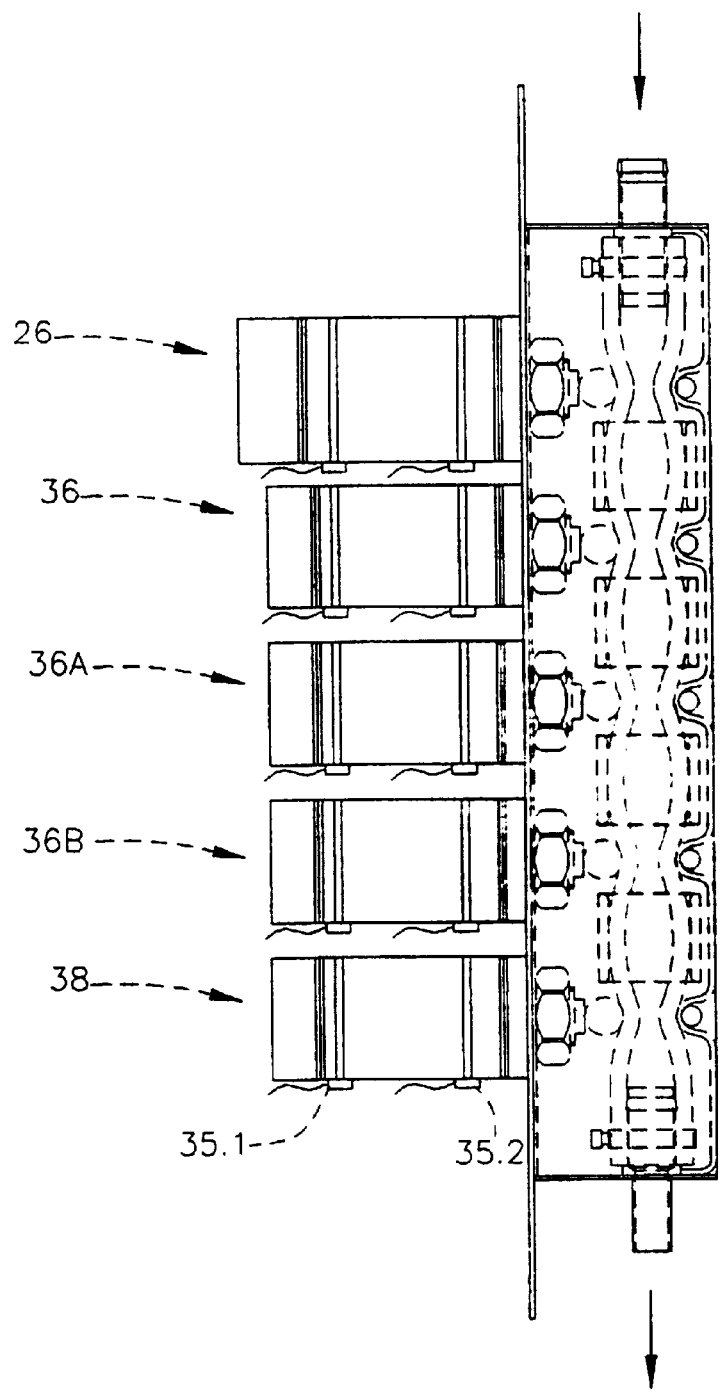
FIGS. 19 and 20 are views similar to FIGS. 14 and 14A but illustrate a still further embodiment wherein three displacement actuators are provided.
Figure 20:
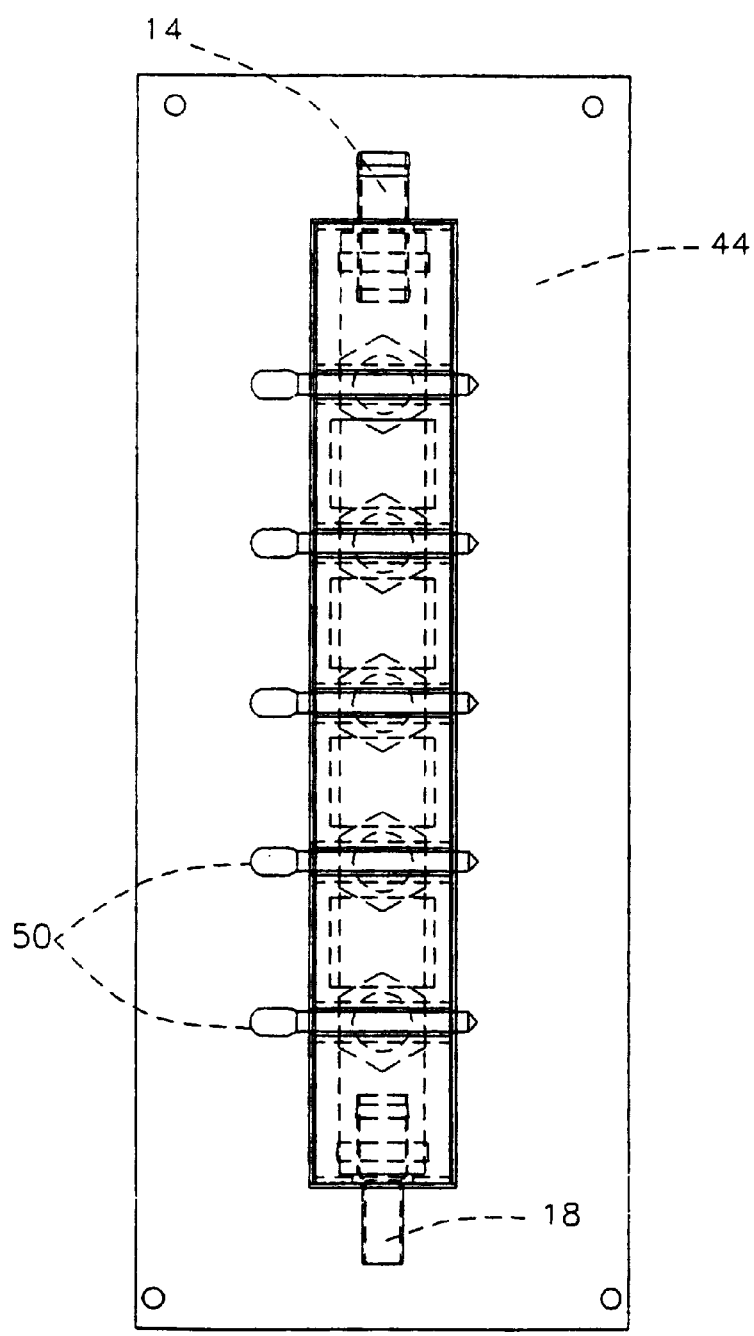

While a pump having two displacement actuators has been illustrated in FIGS. 14 and 14A, and its operation has been described in conjunction with FIGS. 15 to 18F, it should be appreciated that pumps can be constructed with more than two displacement actuators. Such a pump is illustrated in FIGS. 19 to 20, and it is provided with displacement actuators 36, 36A, and 36B. It may be operated in manners similar to that set forth in FIGS. 15 to 18F.

NINTH NOVEL FEATURE

The ninth novel feature of the three element linear peristaltic pump of the present invention is the direct close coupling of the electrically operated pneumatic solenoid valve to the pneumatic port 29 of each air cylinder actuator. It will be appreciated by the reader that the combination of a high durometer pump tube, a dual symmetrical anvil arrangement and force multiplication allows the pump of the present invention to operate at comparatively high cycle speeds. Thus, any refinement to the design which can augment the speed capability of the pump is of significance. The minimization of the gas lumen between the solenoid valve and the air cylinder is such a refinement and has several beneficial effects of significance. First, the speed of actuator compression upon the pump tube, and its removal to an uncompressed condition is optimized. The less compressed gas which must be moved downstream of the valve into the cylinder or through the valve as the cylinder is forced to the retracted position, the faster the actuation sequence can be. Since the cycle speed of the pump is the summation of the various actuations of each of the three elements of the pump, even slight improvements are meaningful. Indeed, the worthwhile improvements in speed as a result of minimizing the gas volume in the valve-actuator pathway can be experimentally demonstrated.

The second benefit of close coupling of the valve and cylinder is a measurable reduction in the gas consumption of the pump. This allows the pump to operate more efficiently and at lower utility cost.

The third benefit of this arrangement of the valve and cylinder is the ability to use a smaller solenoid valve to achieve cylinder actuation. The smaller valve actuates faster, has less bulk and weight, and is less expensive.

The degree of benefit of this method of construction of three elements of the pump is such that the pneumatic fitting or nipple 31 which serves to fasten the valve to the cylinder can even be optimized by reducing the internal diameter of the fitting to minimize system volume while not impairing the flow of compressed gas through the fitting.

TENTH NOVEL FEATURE

The tenth unique feature of the three element linear peristaltic pump of the present invention is the pump elements operating sequence wherein the infeed valve element (IFV) remains open or uncompressed and open (when the pump is not pumping.

The high durometer, stiff walled flexible tubing 12 previously described, in conjunction with the pressure rings 52, also previously described, contribute to a very robust rebound effect after the elements of the pump of the present invention have been compressed. The force of the restoration to open of the pump tube in the IFV is particularly important to the ability of the pump to re-prime with liquid after each pumping cycle, and the speed of restoration has substantial effect upon the time required to achieve such re-priming.

As has also been detailed, the stiff walled pump tube, compression rings, and dual symmetrical anvil arrangement 24.1, 34 all combine to provide very long term service of the pump tube with regard to the compression set and rebound fatigue effects so prominently evident in previous designs. These effects are principal causes of progressive weakening and slowing of re-prime capability and speed in such prior designs. It can be shown that maintaining a flexible tube in a compressed and occluded condition for prolonged periods has a detrimental effect upon the propensity of the tube to rebound to an open (not necessarily round) condition, as a function of rebound force and speed. Further, the longer the occlusion is maintained and the greater the force of occlusion, the more pronounced and severe the effect.

Those skilled in the design and use of positive displacement pumps understand that it is common for pumps to remain idle for prolonged periods of time or to operate only intermittently. Thus, the maintenance of the IFV of a linear peristaltic pump in a closed (occluded) condition, or an undefined condition where it may be occluded during periods when the pump is not operating, is clearly detrimental to the long term optimum operation of the pump. This is the case with linear peristaltic pumps of the prior art.

In the pump of the present invention, the electronic control sequence for the actuation of the pump elements is particularly designed such that the actuator of the IFV is retracted whenever the pump is not sequencing. Thus, the pump tube 12 in the IFV area remains open (unoccluded), and largely open, whenever the pump is not operating. Only the OFV remains occluded when the pump is not pumping. This is particularly beneficial in the pump of the present invention because the IFV, by design, is the highest force element of the pump acting upon the pump tube. Thus, if it were maintained in an occluded position when the pump was not functioning, the pump tube in the IFV would experience the greatest degree of compression set and fatigue, comparative to that of the displacement and OFV locations. Therefore, because the IFV is allowed to assume an open condition when the pump is at rest, this method uniquely avoids the long term static compression of the IFV pump tube section, resulting in a much slower rate of fatigue and compression set of the pump tube.

In a special operating case, where it is not required that the pump remain in a sealed condition such that it blocks liquid flow when it is not operating, or when some other valve in the system into which the pump is installed serves this purpose, all actuators can be retracted, further extending the service life of the pump tube. (This feature is not illustrated). When this is allowed, the electronic controller associated with the pump provides an "all open" selection which causes all elements to remain retracted when the pump is idle. This "all open" mode is also especially useful in some pump cleaning procedures where unrestricted flow through the pump is desired.

ELEVENTH NOVEL FEATURE

The eleventh novel feature of the three element linear peristaltic pump of the present invention is the use of encoded actuators.

As has been previously explained, the pump of the present invention embodies a particularly advantageous design from the perspective of long term stability of flow, pressure and suction characteristics. This is the case when the actuators are operated on an open loop basis where each sequential motion is based upon an electronically defined time. However, there are many enhanced capabilities of the pump and many operating conditions into which the pump may be placed where periodic knowledge of the location and status of the actuators is particularly beneficial, and where such position information allows unique and novel capabilities to be developed and utilized.

Encoding of the actuators in the pump of the present design consists primarily of detecting the extremes of motion of each device. That is, the full open and compressed (which may or may not be occluded) positions of the IFV actuator, the displacement actuator, and the OFV actuator are detected. Means to do this are many and varied and well known to one skilled in the art. They include, in the preferred embodiment, the use of reed switches 35.1 and 35.2 affixed to the pneumatic cylinder wall and detecting the proximity of a magnet affixed to the piston inside of the cylinder, or detection of the magnetic field using suitably positioned hall effect sensors. Other means include the use of inductive sensors, capacitance sensors, optoelectronic sensors, conductivity sensors, and mechanical switches. It is also possible to use pressure sensors to detect the end of stroke or travel of a pneumatic cylinder. It is also sometimes useful, particularly in the case of the displacement actuator, to further encode the motion of the device for intermediate positions between the designed extremes of motion, this being done by a linear encoder 58 shown in FIG. 21. These intermediate position encoding methods, purposes, and advantages are detailed in the portion of this patent application describing methods of pump flow rate control.

When end of actuator motion sensing is utilized, the status of each sensor is integrated into the electronic control system, typically a microcontroller 102. This allows the encoded actuators to be placed under closed loop cycle control. This, in turn, provides absolute and continuous control and optimization of the pump cycle rate and functions. This control capability allows alteration of pump cycle timing and motions as a response to varying operating conditions which cannot be achieved using a time based control scheme. The sensor based method also provides extensive operating diagnostic possibilities which are not obtainable in an open loop control system.

Encoded pump element actuators confer a number of specific and novel advantages to the pump of the present invention. Encoding allows very fast cycle times without the possibility of malfunction due to changing parameters of pump operating conditions. Indeed, because each successive step in the pumping sequence can be initiated as a function of a known location of each actuator, the cycle speed achievable with encoding, and thus the flow rate in a given embodiment of the invention, are maximized. The degree of control required of and provided by the encoded actuators may be better appreciated by considering that in many embodiments of the pump of the present invention the time for one complete pumping cycle can be less than 100 mS.

Another novel advantage conferred by the use of linear encoded actuators in the three element linear peristaltic pump of the present invention, is the ability to pre-open the OFV to any desired degree, including fully open, prior to displacement actuator compression. Partial OFV pre-opening allows a reduction in cycle time, where appropriate to the type of liquid being pumped, by reducing the OFV actuation time before displacement compression begins. If the liquid is not or relatively low viscosity or homogeneous, this shortened pre-open time may be inappropriate and the preferred full pre-opening of the OFV can be selected. When this is the case, the full open condition of the OFV can be verified by the encoding sensor in the cycle prior to displacement. The pre-opening of the OFV, to whatever degree, can be detected by the OFV actuator sensor 35.2 marking occlusion. This verification of motion is important because pre-opening of the OFV reduces the pressure shock and pump tube pressure loading caused by the actuation of the displacement compression element.

Figure 25:
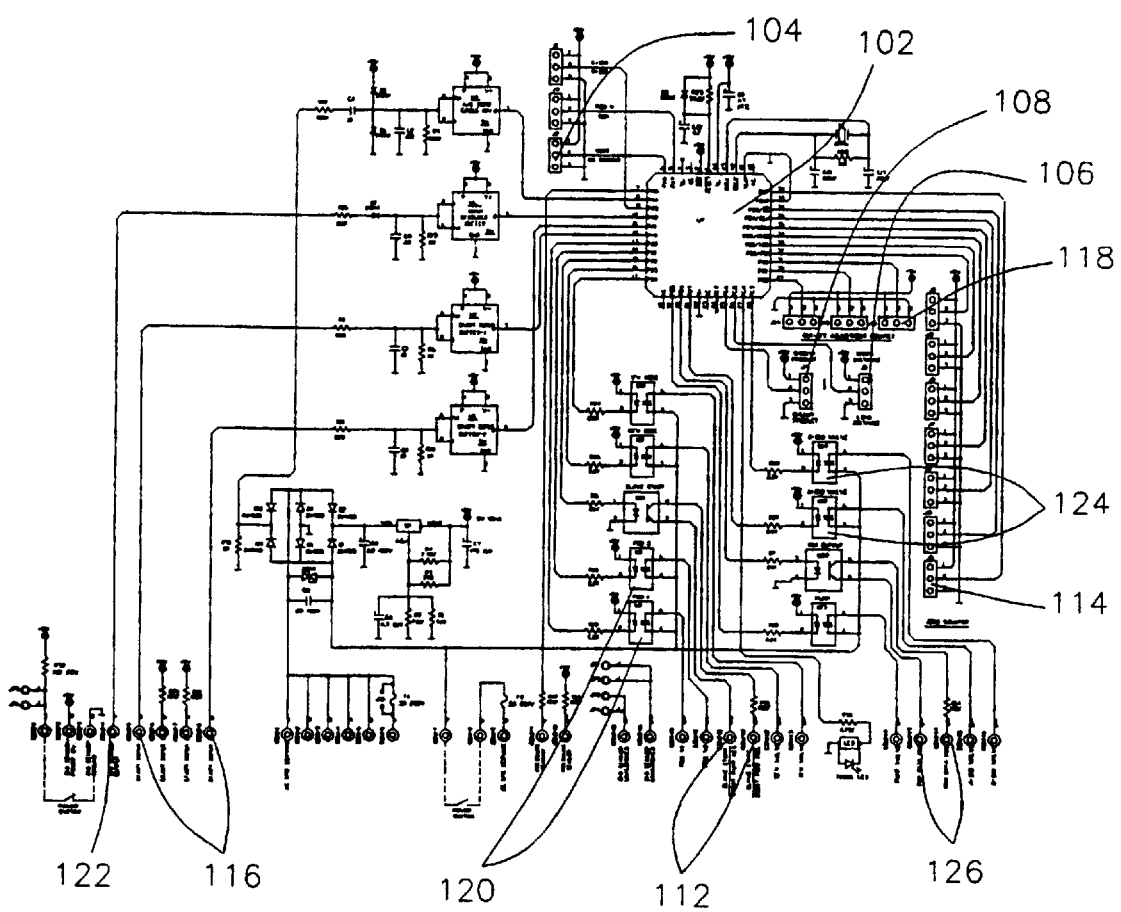
FIG. 25 is a circuit diagram of the electronic control module.

Another novel advantage of the use of encoded actuators is the ability they confer on the pump to adjust to changes in discharge pressure. It is well understood that the differential pressure across any positive displacement pump can vary, particularly as a function of changes in back pressure at the discharge of the pump (also referred to as discharge pressure). As large increases in back pressure occur in the pump of the present invention, it takes longer for the displacement actuator and the OFV to close. Because this is true, in a time based (non-encoded) embodiment, a sufficient period must be programmed into the pumping sequence to allow the displacement actuator and OFV to close and occlude completely within a certain pressure domain, before the next stages in the operating sequence occur. Thus, the cycle of operation cannot be optimized except for a worst case pressure and the system cannot detect or overcome a back pressure beyond some prescribed level. In the electronics illustrated in FIGS. 24 and 25 this problem is overcome by use of a jumper 106 which may be switched between two positions.

However, with encoding, on the other hand, the displacement and OFV actuation times automatically optimize and increase or decrease in duration as the back pressure on the pump varies. This can be critically important, in that it allows the aliquot volume displaced by the pump with each complete cycle to be maintained even as the pressure resisting displacement actuator and OFV occlusion increases. Equally important, the encoding of the OFV uniquely serves as an overpressure indicator to the control electronics. This can be derived either as an excessive open to occlusion transit time, or as a failure to make the OFV occlusion sensor. This novel means of detecting excessive pump discharge pressure is particularly beneficial. Many peristaltic pump designs of the prior art teach detection of high back pressure with the use of pressure sensors or detectors which are either discrete pressure sensing switches or sensors, or with the use of apparatus or mechanisms designed to evaluate pump flow tubing distension or flexure as an indicator of discharge pressure. These methods frequently used with the prior art are generally necessary because the pump actuators may not significantly change their rate of motion or stall with high back pressure because the pump flow tubing utilized can simply be too flexible. The ability to significantly slow or stall the pump OFV actuator and thus detect excess back pressure is unique to the present design and is a direct consequence of the ability of the design to use both a very rigid and essentially non-distending pump tubing and actuator encoding. It should also be understood that excess back pressure detection as described with an encoded OFV actuator can also generally be effected using the pump displacement actuator.

Another unique advantage conferred by the use of encoded actuators is the ability to detect excessively high system pressures. As has been previously explained, the OFV actuator exerts a continuous occlusive force upon the pump flow tube as a function of the applied pneumatic pressure. Acting against this occlusion force is the static system pressure. Thus, when the pump is not pumping, any applied system pressure beyond a certain magnitude can lift the outfeed valve, allowing leakage flow. This lifting is in and of itself uniquely beneficial in that it can act as a pressure relief mechanism within the system into which the pump is installed. Furthermore, such valve lift can be detected by the OFV closed sensor, and annunciated. This is a particularly valuable capability in critical systems where pressure spikes and other excess pressure excursions must not go undetected.

Another novel advantage conferred by the use of encoded actuators is the ability to detect the full open condition of the IFV. This is fully discussed in a separate section.

The use of encoded actuators also uniquely allows the pump to self adapt to its own wear and fatigue. Although the pump of the present invention is far more robust than previous designs, over the long term, as the pump tube is subject to a high actuation cycle count, the compression forces and rebound forces will change. These changes can be automatically sensed and measured as a result of the encoded actuator strategy. As such, it is possible to alter sequence times to maintain pump performance over the useful life of the system. It is also possible to detect the end of useful life of the pump tube and thus to annunciate the need for change, and catastrophic pump tube failures as a result of overuse of the pump tube can be largely avoided.

Overall, the encoding of each actuator in the pump, in conjunction with use of force multiplication geometry, high durometer pump tubing, and the use of dual symmetrical anvil geometry, fulfills a primary object of the present invention which is to embody a linear peristaltic pump with a high stability of output volume per pump cycle over time and thus offer a high predictability of performance.

TWELFTH NOVEL FEATURE

The twelfth novel feature of the three element linear peristaltic pump of the present invention is the high viscosity priming capability of the device.

The limitations of known linear peristaltic pump designs to handle viscous liquids at high discharge pressures has been previously discussed. It is also well understood that linear peristaltic designs of the prior art are typically constrained in their ability to pump viscous liquids as a function of their inability to overcome slow and incomplete priming of the pump due to the high flow resistance and suction drag imposed by such liquids.

The use of force multiplication geometry, symmetrical anvils, and pressure rings allows the use of a high durometer, compound wall, reinforced pump liquid flow tube to generate high pumping pressures. This ability to use very stiff tubing in the pump of the present invention, in turn, allows extremely high rebound forces to be generated by the pump tube after compression. These high rebound forces uniquely overcome the principal problems of liquid priming of prior designs; namely, lack of adequate opening force for suction priming and the substantial reduction in and eventual loss of restorative force as the tube undergoes extended cycle use.

In the pump of the present invention, the powerful rebound or opening capability of the pump tube is sufficiently forceful to return each actuator to full open in a rapid and positive manner, without the need for pneumatic or spring assistance. This is important to the simplicity, durability, and economy of the design. Further, when the pump tube is replaced, the return spring force available to each actuator is automatically renewed.

The extent of the capabilities of the pump of the present invention to prime with high viscosity liquids is dependent both upon the speed with which the tube can re-open in the IFV and displacement elements, and the force the tube can overcome and still return to its fully open condition (fully open typically and preferably being partially pre-compressed). In the present invention, if a vacuum equivalent to thirty inches of mercury is applied to the IFV and compression elements of the pump, with the OFV remaining sealed, the pump tube can be compressed and will overcome this force and rebound to open without significant reduction in restoration time when compared to the restoration time at full atmospheric pressure. A design for a pump where the lumen opens freely even against a nearly complete vacuum (the greatest force resisting opening which the pump can encounter) is unique to this linear peristaltic pump design, and places the present design on a par with positive displacement pump designs utilizing rigid materials.

It will be understood that the suction priming force which can be developed in a pump is limited by the degree of vacuum which the pump can generate. The differential pressure between atmospheric pressure and the pump induced vacuum largely defines the priming force available to move liquid into the pump lumen. The pump of the present invention is capable of producing a comparatively high vacuum at its infeed because of the robust nature of the pump tube. Because the pump can generate such a high vacuum condition and can operate without a slowing of the tube motion under high vacuum conditions, it is capable of priming high viscosity liquids and can do so without being slowed by the suction drag of the inflow rate of the liquid. In effect, the rebound force is so great that the tube will open to its allowed open state without measurable slowing, whether or not liquid can flow at a rate sufficient to fill the rapidly growing lumen. Thus the speed of priming actuation of the pump of the present design does not present a limitation to the high viscosity priming capability even under worst case suction pressure conditions.

One skilled in the art of pumps will recognize a condition where a viscous liquid cannot flow at a sufficient rate to fill a vacuum lumen as a condition known as starvation, or more properly as vacuum cavitation. This condition is generally viewed as undesirable in that it causes the volumetric efficiency of a pump to be lost. In the pump of the present invention, when such a condition occurs, the displaced volume per complete pump cycle will drop substantially. This is because while a complete lumen of prescribed volume is created when the IFV and displacement sections open, the viscous liquid being pumped cannot fill the lumen in the allotted time, and the IFV closes off on only a partially filled lumen. With the next displacement compression, the partial volume is displaced out of the pump and the cavitation process repeats. The present invention is uniquely capable of overcoming this problem of viscous priming by virtue of the ability of the control electronics, via jumper 108, to allow an increase in the IFV open time, This effectively increases the prime time as a discrete and separately adjustable time event in the pump cycle. Thus, when the flow rate of the pump, ultimately the volume displaced per cycle, is noted to decrease when pumping a viscous liquid, increasing the IFV open time allows the prime lumen time to completely fill with the liquid and thus the actual volumetric flow rate will increase by lengthening the cycle time of the pump. This effect can be empirically demonstrated in the pump of the present invention. The necessary control capability is provided for as part of the electronic controller, typically a microcontroller which forms an integral part of the pump.

The unique ability of the pump to be provided with linear actuators which are encoded provides the novel ability of the design to automatically compensate for pump tube priming fatigue by increasing the priming time (IFV open). The pump tube used in the present invention exhibits little reduction in rebound force over a prolonged useful life. However, in the very late stages of that life cycle, the force may drop sufficiently to slow tube opening at the IFV after compression and occlusion. The use of the open status sensor allows this time shift to be detected. As the rate of lumen creation slows, the rate of vacuum creation also slows and the rate of inflow of viscous liquids into the lumen may also decrease. Thus the microcontroller 102 can be preferably designed to increase the total IFV open time by adding time to the open period after the IFV open status sensor is detected. This can improve liquid feed and thus offset any volumetric flow decrease. The microcontroller can, using the same methodology, uniquely detect and annunciate an IFV opening time which can be considered to be so long as to constitute an end to useful pump tube life.

THIRTEENTH NOVEL FEATURE

The nature of the design of the pump of the present invention allows numerous unique means of liquid flow rate control, from very simple to relatively sophisticated. These methods of flow rate control constitute the thirteenth unique feature of the three element linear peristaltic pump of the present invention.

On the simplest level, a first method of flow rate control allows adjustment downward from the maximum volumetric flow rate of a particularly sized version of the present design, and consists of simply electronically increasing the duration of the IFV open time. As explained previously in this patent application, the IFV must be held open for some minimum time to effectively allow the lumen created by its opening to fill with liquid. This constitutes the priming portion of a pump cycle. It will be apparent that holding the IFV open for a period greater than the necessary priming time does not affect the volumetric dose of the pump, but does cause the total pump cycle time to increase. This increase results in fewer pump cycles in unit time, which constitutes a reduction in flow rate. One skilled in the art will note that a similar increase in the duration of essentially any discrete element of the pump cycle will allow the same result. However, increasing the IFV open time is the best choice for this means of flow rate control because it is also the sequence time adjusted for high viscosity liquid pumping. The net effect of this method is to reduce the frequency with which the displaced volume is produced from the pump. This reduction in pumping frequency is sometimes acceptable in terms of the usage of the pump, but is frequently objectionable for its consequences to other apparatus and purposes to which the pump might be employed.

A second unique method of changing the flow rate of the pump, also relatively simple in nature, consists of varying the gas pressure force to the encoded pump actuators. Reducing gas pressure can slow the rate of motion of the pump actuators, resulting in fewer pump cycles in unit time and thus a reduced flow rate. Conversely, increasing gas pressure could increase the number of cycles in unit time, raising the flow rate accordingly. The net effect is to change the frequency of pumping cycles. As in the first method of flow rate change, when the frequency is decreased using this second method, it is often objectionable due to its consequences within the scope of the pump's application.

A third method of flow rate control is unique to the design of the present invention. It allows adjustment downward from the maximum flow of a particularly sized version of the present design, and consists of electronically reducing the open time of the IFV. After the first pump cycle where the IFV typically has been open during any previous pump rest or standby condition, the IFV is opened for a prescribed time, whether marked and defined by end of travel sensors on the IFV actuator, or, in an open loop system, by an internal timer in the control electronics. By reducing the open time of the IFV, the displaced dose per pump cycle can be reduced. This constitutes a reduction in flow rate. This is the case because the volumetric size of the suction lumen created by the IFV is reduced as the amount of its motion is reduced. This methodology is effective, inexpensive to implement, and has a relatively large dynamic range of operation and preserves the differential and discharge pressure capabilities of the pump, and does not reduce the cycle speed of the pump. This method is unique to the present invention in that the extremely high durometer of the pump tubing combined with the dual symmetrical anvil design allows a very stiff and continuously loaded rate of motion of the actuators (the IFV element in this case), thus allowing a high degree of repeatability and stability in the method which could not be achieved in prior art designs. Effectiveness of the method can be further enhanced in the preferred embodiment where the actuators are encoded as previously described. However, this method is still subject to variations caused by changes in pump net inlet suction pressure, or product viscosity changes, since the amount of liquid entering the pump in unit time is influenced by these variables.

A fourth method of flow rate control is unique to the design of the present invention in that it relies upon the very high degree of repeatability and stability of actuator motion as afforded by the stiff design and the very repeatable force versus distance profile afforded by the dual anvil design. With this fourth method the cycle timing and motion relationship between the pump section and the OFV is electronically varied to effect a change in displaced pump volume per cycle. To understand fully how this can occur, recall that in a typical pump cycle the OFV first opens at least partially, followed by compression of the pump section, followed by closing (occlusion) of the OFV while the pump section remains at compression. The displaced pump volume per cycle is always the displaced volume of the pump section lumen since, if the OFV never opens completely, the pump section displacement is expelled from the pump except for that fraction consumed or taken up by the created lumen in the OFV, with that portion being also expelled from the pump with the subsequent compression or closing of the OFV. The volumetric sum of the two fractions is always equivalent to the displaced volume of the pump section lumen. In the case where the OFV opens completely followed by pump section occlusion followed by closing of the OFV, the volume displaced by the pump section is first primarily displaced into the OFV lumen, then with the closing of the OFV valve lumen, on out of the pump, in sequential fashion. Again, the total of volumetric displacement is always equivalent to the displaced volume of the pump section lumen, which is typically volumetrically identical to the displacement lumen created by the opening and closing of the OFV. With this in mind, it will be apparent that if the timing and motion relationship between the pump section and the OFV are altered such that before the OFV occludes completely and seals, the pump section is allowed to begin to return to an open or unoccluded condition, a portion of the volume previously displaced by the pump displacement section will be drawn back into the pump section in a manner akin to the entry of liquid into the pump section lumen from the infeed end of the pump during priming. The net result of this new method of motion of the two elements is the ability to electronically control the displaced volume per pump cycle in a smooth and repeatable manner with electronic adjustment. Further, the discharge pressure capability of the pump is not adversely affected, the feed of liquid into the pump is not altered, and the method is largely insensitive to variations in pump pressure. When the pump actuators are encoded, the precision and stability of this method are further enhanced.

A fifth method of flow rate control novel to the present invention consists of limiting the amount of compressive travel or occlusive motion of the pump actuator by controlling the time for which the actuator driven anvil is allowed to move toward the occlusive position, and by providing valving or other means, including a mechanical stop (FIG. 22) to hold the anvil in any desired intermediate position until the OFV has closed.

Taken together, the high durometer very stiff pump tubing utilized in the present design, and the symmetrical dual anvil arrangement along with the close coupling of the pneumatic valve to the cylinder actuator, allow a very repeatable and precise motion control which can be shown to be stable over time. This, in turn, allows a controllable and repeatable degree of motion in unit time which can be controlled to reduce the actuator stroke below the occlusive maximum, thus reducing the volume of liquid displaced from the pump section with each pump cycle.

In the instance where end of travel sensing of actuator stroke is utilized (encoded actuators), the precision and repeatability of the motion is further improved because the starting time of actual motion is known and marked. It is important to understand that the preferred version of this method of flow rate control requires the ability to hold the pump actuator motion at any desired intermediate travel position between fully open (fully open typically being a position where the pump tube is partially pre-compressed) and completely occluded. It is possible to utilize this method of limiting pump cycle displaced volume without holding the pump actuator travel at an intermediate position, but it requires arranging the control electronics so that the OFV begins opening simultaneously with the start of pump actuator compression, with the OFV being reversed in its travel well ahead of the time where the pump actuator motion is to be reversed. This is the case because it will take a finite time for the OFV to reverse and reach occlusion while the pump actuator is continuing to travel toward some desired partial compressive position. The result of this method is to limit the amount of opening of the OFV to such a restrictive degree that heterogeneous liquids such as slurries and particulate or chunky liquids can not readily pass the OFV occlusion point without degradation. Even homogeneous liquids pass through the restricted OFV opening only at higher velocities than is the case with the OFV more fully opened. This method can also result in momentary pump actuator over-travel against the closed OFV, causing an unwanted pressure spike to be applied to the closed IFV and to the OFV. It is possible to arrange the control electronics such that the OFV is opened completely as a function of a defined time or as signaled by the OFV full open end of travel sensor, followed by the immediate reversal of the OFV actuator such that it begins to move back toward an occluded position. During the OFV occlusion motion, the pump actuator begins to move toward occlusion. Because the "time of flight" motion and geometry of each actuator is essentially identical, the OFV will reach occlusion prior to the completion of the pump displacement actuator stroke, thus defining a partial displaced volume. Upon the completion of OFV occlusion, either as a function of a time defined by the electronic control system, or by the signal of the OFV full closed end of stroke sensor, the motion of the pump displacement actuator is instantaneously reversed. The functional limitations associated with this variation on the method are essentially the same as those previously described, wherein flow is occurring at an increasing velocity through a decreasing clearance orifice limiting flow and preventing passage of solid inclusions within the liquid, and wherein an unwanted pressure spike can be generated as OFV occlusion is reached. Thus it can be seen that the preferred version of this fifth method of pump flow rate control wherein the stroke distance of the pump displacement actuator is limited and then held in position until the OFV is again closed, is superior to alternative arrangements because the novel design elements of the present invention can continue to be used to advantage, including relatively low velocity of liquid movement past the OFV occlusion position, a large flow pathway past the OFV occlusion point allowing pumping of slurries, mixed phase liquids, and liquids with large solids inclusions, and closure of the OFV with little or no relative flow velocity from the pump displacement actuator and free of pressure spikes from the pump displacement actuator.

Figure 22:
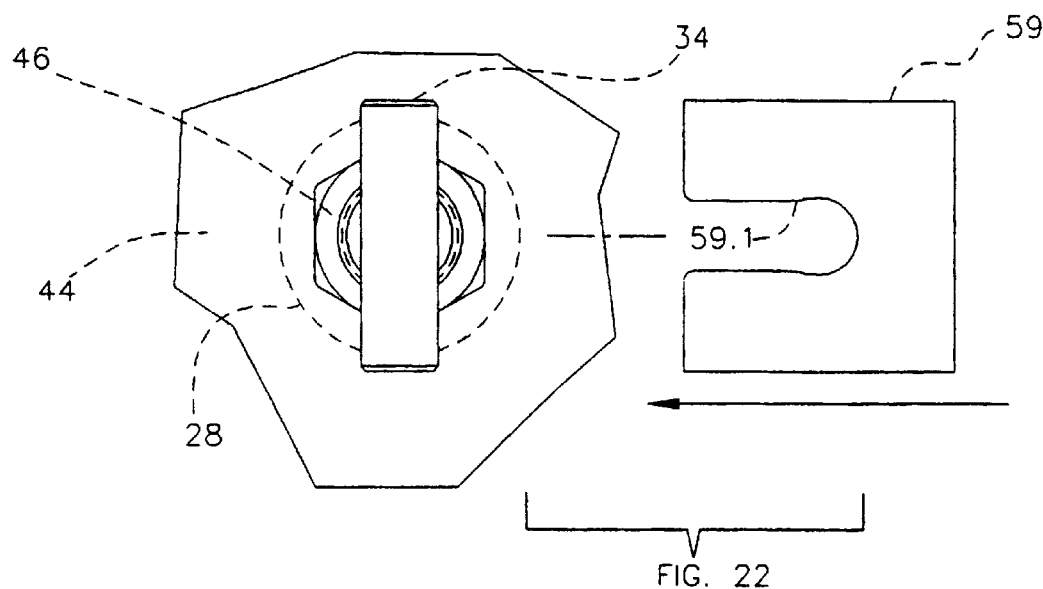
FIGS. 21 and 22 are side and end views, respectively, showing how a dose block may be mounted to limit movement of the displacement actuator.
Figure 21:
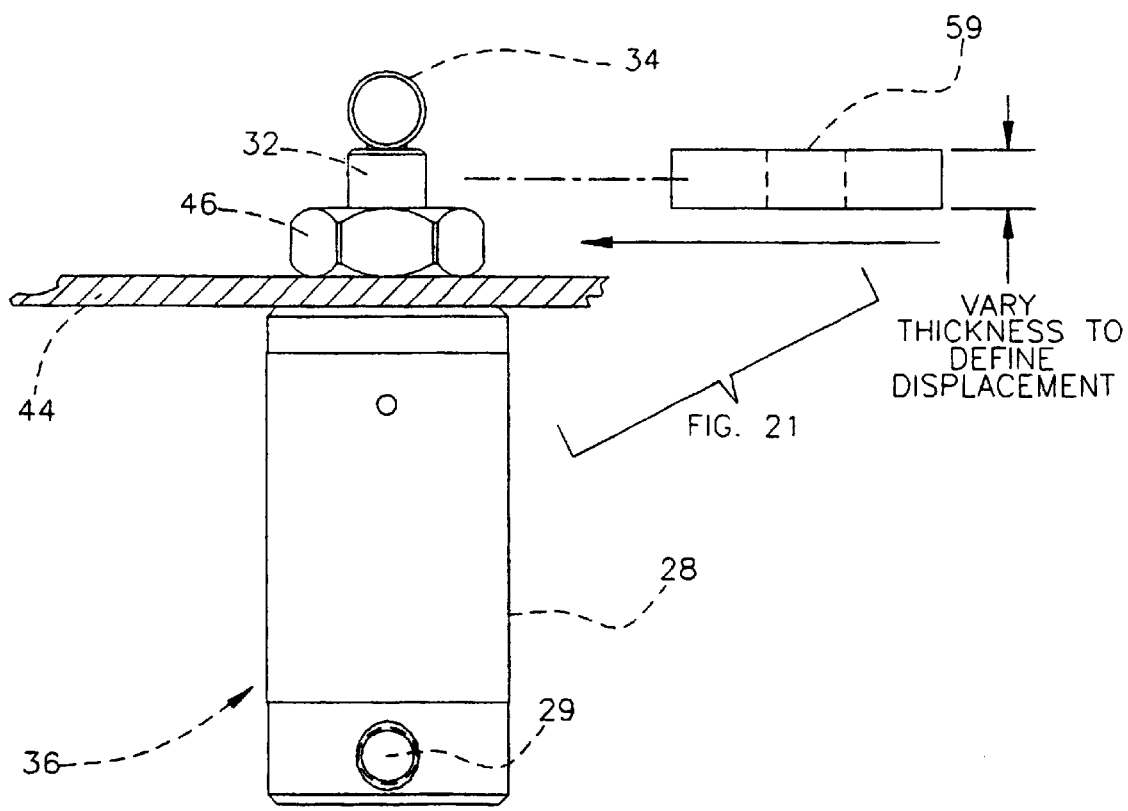

There are two methods of achieving a holding capability of the pump displacement actuator at some partial stroke distance. Either is preferred, the choice being one of commercial preference and economics. The first holding method, which is illustrated in FIGS. 21 and 22, consists of providing a mechanical stroke limiting stop 59, termed a dose block, or dose limiting block. The dose block may be designed such that it prevents the full return of the pump displacement actuator to its full open position thereby reducing the volume displacement capability of the pump. In the illustrated design, the dose block is provided with a keyhole slot 59.1 which is so dimensioned that the dose block will snap about the rod 32, the sidewalls 22.2 and 22.3 of the U-shaped channel holding it from rotation. The dose block may be made of varying thicknesses as desired. Alternatively, a dose limiting block of a different design can be inserted into or onto the pump displacement actuator such that the actuator is mechanically constrained from reaching its full occluded motion position. In either case the dose block is inserted such that it does not interfere with the geometry of the dual symmetrical anvil arrangement previously described. In addition, the physical dimension of the dose block in the axis which restrains actuator travel will define the displaced volume of the pump per cycle and can be specified to achieve essentially any desired flow rate within the overall design range of the particular pump. It is also possible to provide an adjustable stop serving the same purpose as a dose block.

Figure 23:
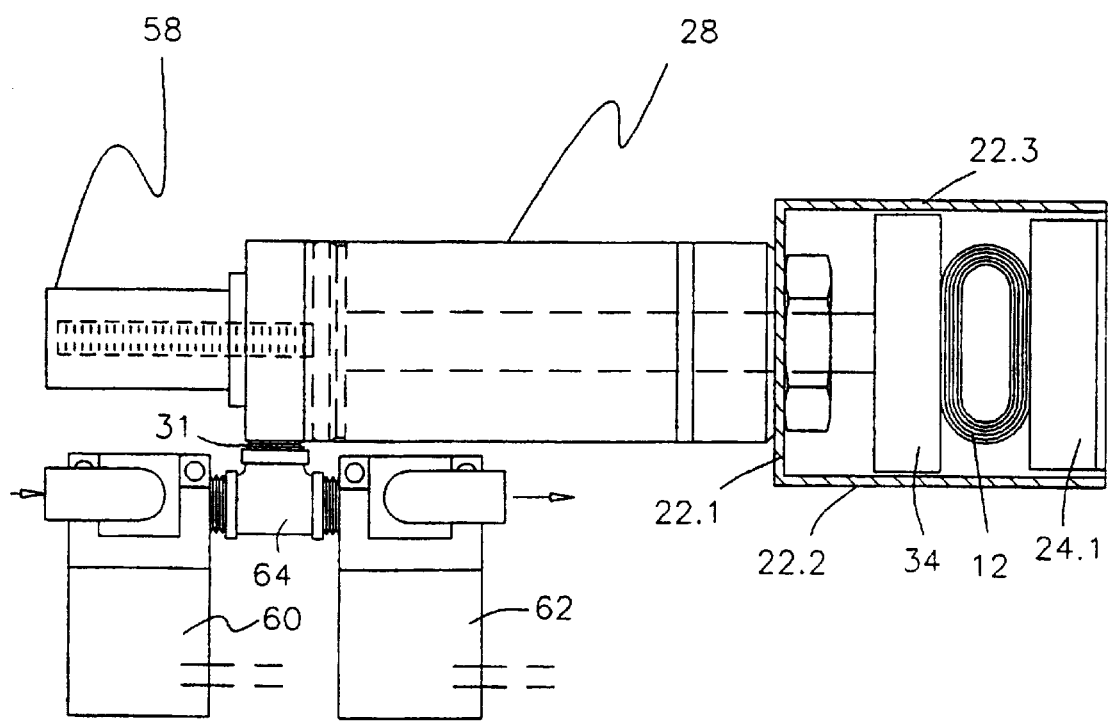
FIG. 23 is a side view showing a displacement actuator provided with a linear encoder and separate pressure and exhaust valves.

The second preferred method of achieving a holding capability of the pump displacement actuator at some partial stroke distance involves changing the pneumatic control valving of the actuator as shown in FIG. 23 (other actuator types such as hydraulic or linear electric being also possible). As previously described, the pump displacement actuator is controlled by a normally closed electrically operated pneumatic solenoid valve. To gain stroke control of the air cylinder, the valve means is changed to consist of two 2-way normally closed solenoid valves 60, 62 each closely connected to the pressure port of the cylinder actuator. Valve 60, which may be referred to as the pressure supply valve, is connected to the pressurized gas supply. Valve 62, which may be referred to as the exhaust valve, serves as a separately controllable exhaust valve. The valves are mounted on a T fitting 64 which is in turn connected to the nipple fitting 31. In operation, the pressure supply valve 60 is opened for a defined time, and then closed. This results in movement of the pump displacement actuator over a defined distance. Because the pressure supply valve closes after a pressure delivery period and the exhaust valve is closed, the actuator will remain at some intermediate displaced distance for an extended period of time, termed a holding time. During this holding time, the OFV, previously opened in the cycle in the usual manner, is closed, completing a displacement cycle in which a reduced volumetric displacement is achieved. After the OFV is closed, the complete pump cycle continues in the usual manner in which the valve 62 is opened, permitting the tube 12 to force anvil 34 to an open position. This preferred method may be used in pumps of the preferred embodiment without end of travel sensors in which case an open loop, electronically defined pressure supply valve time is used. The method may also be used in pumps of the preferred embodiment equipped with actuator sensors, in which case the start of the pressure valve time is marked by the loss of the full open sensor signal. This further improves precision. The advantages of this fifth method of pump liquid flow rate control include the ability to span a very large dynamic range of flow rates from the maximum of which the particular pump is capable to rates of a few percent of the maximum, reasonable precision, repeatability, and long term stability of flow rate, unaffected range of pressure and viscosity capability, preservation of the most favored sequence of operation of the pump elements and, consequently, the most advantageous pattern of liquid flow within the pump. Of particular note, the frequency of pump operation does not decrease with reducing rates of flow. In fact, as the pump displacement actuator motion is reduced to reduce flow, its actuation time decreases, which actually increases the frequency of pump operation. This can be advantageous in numerous applications, but where it is desired, it is comparatively simple to use the electronic controller, typically a microcontroller, to add time into the pump cycle as previously described in order to hold the pump operating frequency steady regardless of selected flow rate. It should be noted that any adjustment of flow rate as a function of the degree of compression of the lumen of a tube is inherently non-linear. However, it is comparatively straight forward and effective to use an algorithm or data look-up table in the software of a microcontroller to linearize the necessary compression adjustment of the pump displacement section to facilitate linear adjustment and calibration of flow rate of a pump of the present invention.

A sixth method of flow rate control of the pump of the present invention, which is novel to the present invention and a preferred method, consists of utilizing the dual valving arrangement and control means described in the fifth method of flow rate control, with the addition of a linear incremental encoder 58 to define the desired increment of motion of the pump displacement actuator.

The pump of the present invention can be operated open loop without encoding sensors or, for greater precision and flexibility of use, end of travel or stroke sensors can be added to periodically detect and interlock the pump sequence. In addition to these sensors, it will be appreciated that the motion of the pump displacement compression actuator can be further monitored, beyond fully opened and fully compressed as provided by end of stroke sensors, in order to allow closed loop control of the actuator motion to any intermediate location. The use of intermediate position encoding of the pump compression actuator provides further improvement to flow rate accuracy and stability because the movement of the actuator continues until a prescribed position is reached regardless of any change in actuator velocity or force as a function of any external influence. Thus, all of the benefits and advantages ascribed to the fifth method of flow rate control apply to this sixth method as well, with the additional benefit of still further improvement of precision of repeatability and stability of the actuator's motion. The means of encoding are many and well known to one skilled in the art and may include the simple provision of physically moving the end of stroke sensor to some intermediate position where it signifies the completion of a desired volumetric displacement. This may be thought of as an electronic equivalent of the mechanical dose block described earlier. Other means of encoding which provide the convenience of electronic adjustment of stroke include, but are not limited to, the use of linear potentiometers, the use of rotary potentiometers where the linear motion is converted to rotary motion by a suitable linkage or engagement, the use of a linear variable displacement transducer (LVDT), the use of a variable output capacitance sensor, the use of a variable output inductance sensor, the use of a linear digital encoder such as a glass scale type, or the use of a rotary incremental or absolute position encoder where the linear motion of the displacement actuator is converted to rotary motion by a suitable linkage or engagement.

The fourteenth novel feature of the three element linear peristaltic pump of the present invention concerns the electronic control capabilities of the design.

The electronic control system 100 of the present invention, typically using a microcontroller 102, can be selected by switch input 104 into one of two primary operating categories or modes. (This can also be done by display input). The first mode is termed metering, and the second is termed dosing. This self contained electronic capability to operate the linear peristaltic pump in either status is unique to this design.

The present design provides several unique capabilities when operated in the metering mode. Because, in one preferred embodiment, the actuators are position encoded, the control electronics is able to continuously monitor and analyze actuator positions and travel rates, and thus establish and maintain desired flow rates. This fundamental ability is not possible in linear designs of the prior art where the position and motion rate of each pump element is unknown and where each actuator is discretely controllable. The control electronics in one preferred embodiment of the present invention is able to establish and maintain a defined volumetric flow rate (termed metering) by first establishing the volumetric flow produced with each complete pump cycle. This is accomplished by placing the pump in its dosing mode (discussed in detail further on) and measuring the displaced volume of a test dose. This test dose can then be entered into the microcontroller, expressed in units such as milliliters, and the controller can then compute the volumetric displacement per cycle. For example, if a 25 cycle test dose produces a 60 milliliter displaced volume, the controller would compute that the volumetric displacement per cycle of the pump was 2.40 mL.

Once the volumetric flow per cycle of the pump is empirically determined, there are three unique methods by which metered flow can be established with the pump of the present invention. In the first, an algorithm in the controller computes the necessary number of pump cycles per minute required to establish the required flow. This cycles per unit time interval method is established by knowing the volumetric flow per pump cycle, and by knowing the cycle time for a complete pump sequence. With these data, the microcontroller can compute the necessary hold up time to be added to each cycle to yield the exact cycles per minute to define a desired flow rate. The added time is included preferably into the IFV open time portion of the pump sequence. Also uniquely, as the cycle time of the pump is altered, for example by an increase in back pressure, the pump cycle frequency is continually re-computed by the control electronics to maintain the requisite flow rate. Also uniquely, if the necessary cycle speed of the pump to maintain specified volumetric flow exceeds the pump's capability (that is when the IFV open time has been reduced to its allowed minimum duration) an alarm provision is provided to warn of this condition.

The second unique electronic control method by which the present invention may be utilized for metered flow utilizes the sixth method of pump flow rate control as previously described. The second metered flow method utilizes the same data as the first, but establishes and maintains flow in a different manner. Under this method, the displacement of the pump is adjusted as a function of the degree of compression of the displacement element. Thus, a metered flow consists of producing a known volumetric displacement per pump cycle at a known frequency. However, in this method, as the flow rate is detected by the control electronics to alter as manifested by a change in the continually measured cycle time of the pump, the displacement per cycle is electronically altered to re-establish the desired flow rate. Thus, in the first unique method, the cycle frequency is altered to compensate for a flow rate change as measured by cycle frequency, while in the second unique method, displacement per cycle is altered to compensate for a flow rate change as measured by cycle frequency. As with the first method, if the displaced volume cannot be further increased to compensate for reduced flow, an alarm function is provided by the control electronics.

The third unique electronic control method by which the present invention may be utilized for metered flow utilizes the variable analog or frequency signal supplied by an external flow meter 128 (FIG. 5) of suitable type. With this method, flow rate variations as measured by the meter are compensated for within the pump control electronics. As the meter signal varies, the error is compared to the desired set point and flow is adjusted by any of the six flow rate methods previously described until the feedback signal from the meter and desired flow set point eliminate the error component.

The second major mode by which the control electronics can be operated is termed dosing, which is selected by switch 104. In this setting, the electronics can control the pump to produce a defined volume of liquid with a high degree of repeatability. Two methods, unique to the present invention can be utilized to establish a desired dose volume. In each of these methods, the maximum volumetric displacement of the pump is first defined using the test dose method already described. In describing the first unique method of establishing a dose volume, it will be understood by the reader that a dose volume that is not an even increment of the unaltered volumetric displacement of each pump cycle could not be achieved without changing the displacement of the pump. The necessary mathematics to do so under the first method of defining dose volume is computed by the microcontroller. An example of the process will reveal the structure of the algorithm. Consider the instance where a test dose shows the volumetric displacement of the pump per cycle to be 2.40 mL, and a dose of 130 mL is desired. In this case, 2.40 is divided into 130 to determine that 54.1666 cycles are required to deliver the dose. Since, in this first method, a partial pump cycle is not possible, and the 2.4 mL per cycle displacement is the maximum the pump can deliver (in this example), 55 pump cycles must be used to deliver the desired 130 mL. Fifty-five pump cycles at 2.40 mL per cycle will produce a dose of 132 mL, an overdose of 2.00 mL. Thus, the displacement of the pump must be reduced by 2.00 mL over 55 cycles, which is a reduction in volume per cycle of 0.03636 Ml. Thus, displacement per pump cycle must be reduced from 2.40 mL to 2.3636 mL.

The means most preferred to achieve a change in the displacement per pump cycle has been previously described as method six for flow rate control under the heading "Thirteenth Novel Feature". It will be understood that an algorithm defining displacement as a function of the degree of compression of the displacement actuator of the pump can readily be constructed, and that a suitably encoded actuator as described in method six allows implementation of the calculated displacement change to achieve any desired dose volume within the design range of the pump.

As a practical matter, it should be explained that in dosing applications it is frequently desirable to select a suitable flow rate, and then select a dose volume. This poses no problem in the first dose volume setting method described, in that flow rate can be varied as desired using such input devices as a numerical keypad, rotary dial controls, thumbwheel control, or display input. Once the desired flow rate has been established, the same procedure previously described can be followed to define the dose, with no perceptible change in the desired flow rate of the dose volume.

The second unique method of electronically defining a desired volumetric dose consists of altering the displaced volume of only the last pump cycle associated with the dose. This method may be referred to as the dose trim method. Again, by example, and using the same data as in the previous examples, 54 pump cycles of 2.40 mL per cycle delivers a dose of 129.60 mL. A 55th pump cycle delivering 0.40 mL would define the desired 130 mL dose.

There are two means by which the displaced volume of the last pump cycle associated with a dose may be altered or trimmed. In the first, the compression travel of the displacement actuator motion control means as described in method six for flow rate control under the heading "Thirteenth Novel Feature". In the second, the displacement actuator travels for its full stroke, and part of this displaced volume is drawn back into the pump as the actuator returns toward its unoccluded position under linear encoder motion control and prior to the close of the OFV. This second means has been previously described as the fourth method of flow rate control under the heading "Thirteenth Novel Feature" and differs from that description only in that the change in the relative motion of the displacement and OFV elements is implemented in only the last pump cycle of the dose pump cycle grouping.

As with the first method of electronically establishing any incremental dose volume, this method allows for electronic adjustment of the flow rate of the system prior to establishing the dose volume set point.

Another unique feature of the control electronics of the three element linear peristaltic pump of the present invention is the provision for an electronic output firing pulse or signal which can be utilized to actuate other similar pumps of the present invention via terminals as shown at 112. This firing pulse or signal can be selected to occur at any desired point in the pump sequence, thus allowing a high degree of control over the configuration of a multiple pump system. This provision allows, in turn, three unique electronic control capabilities.

Figure 27:
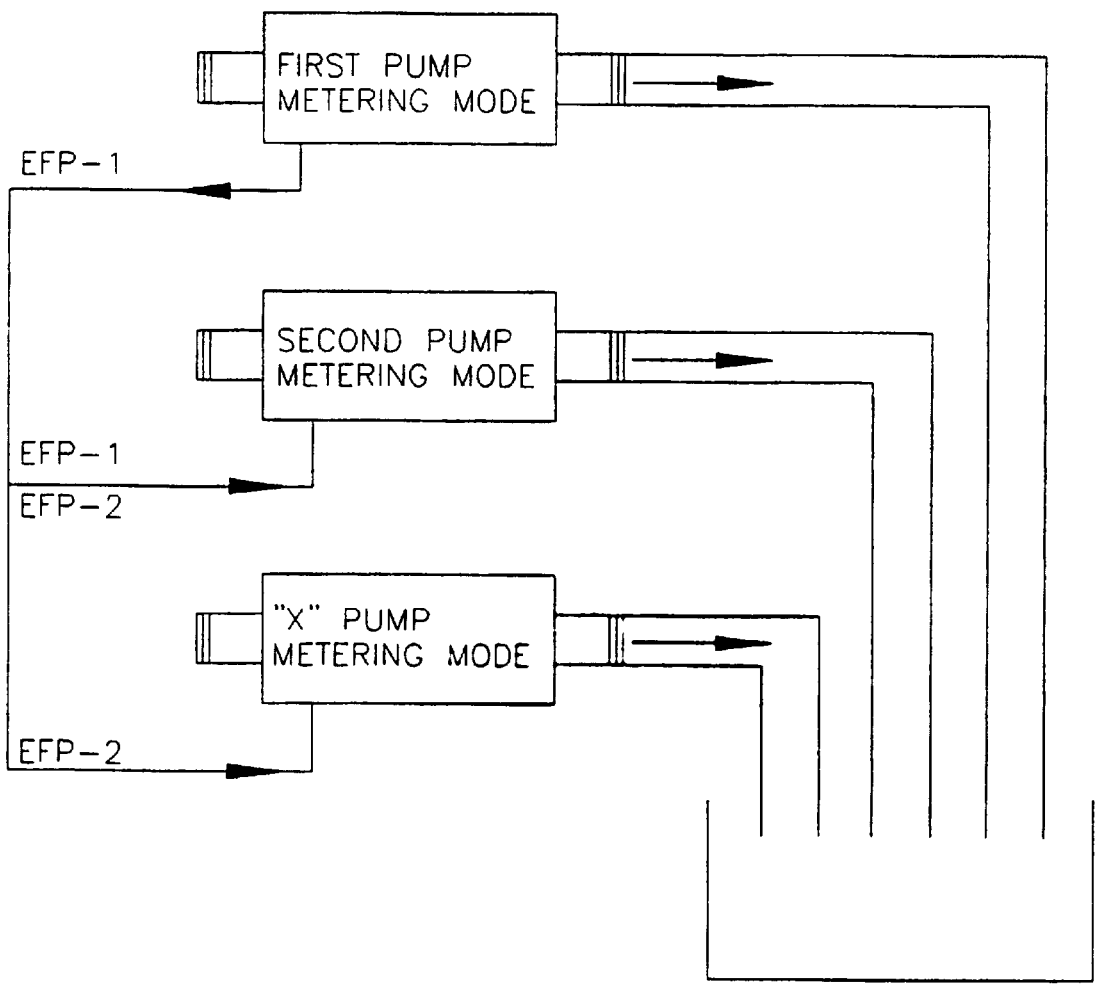
FIGS. 27–31 illustrate how two or more pumps may be controlled.
Figure 28:
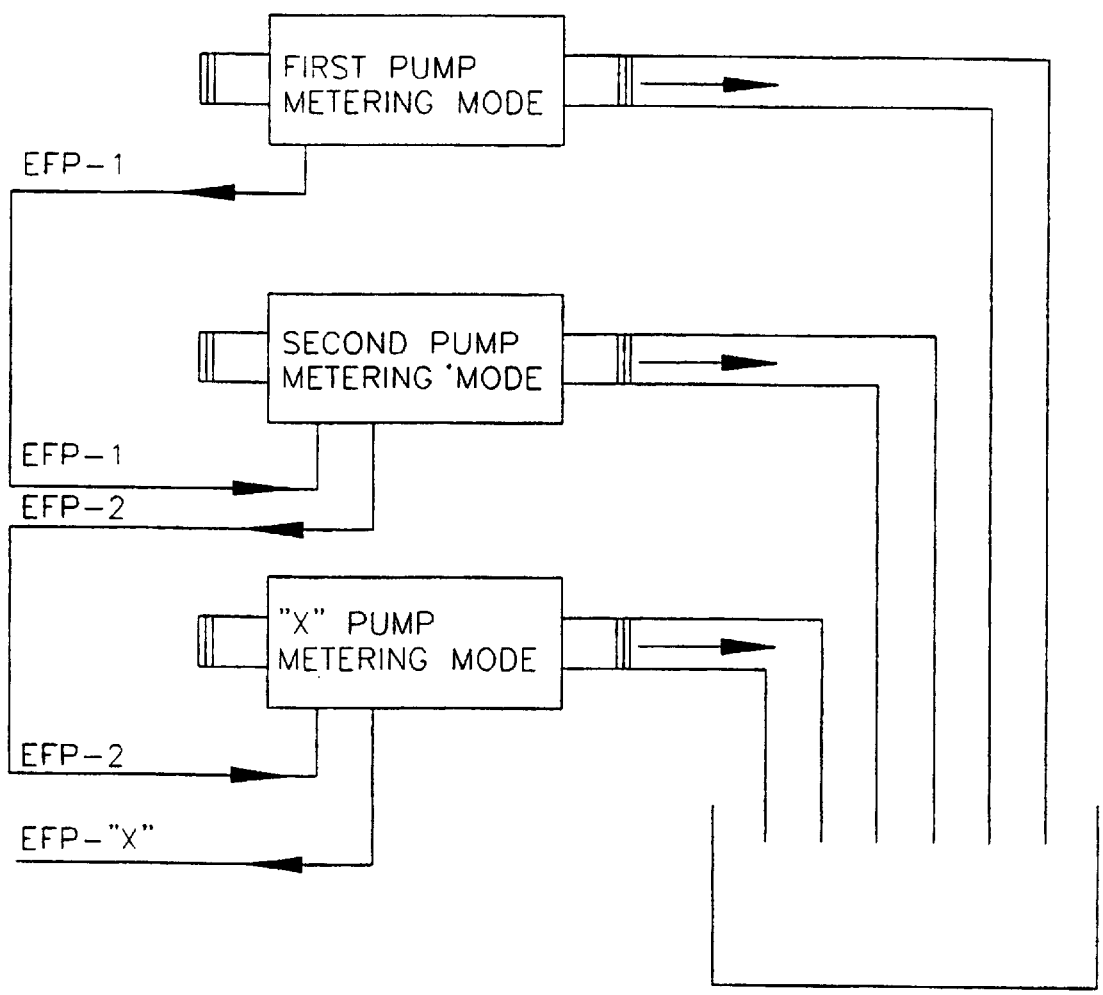
Figure 29:
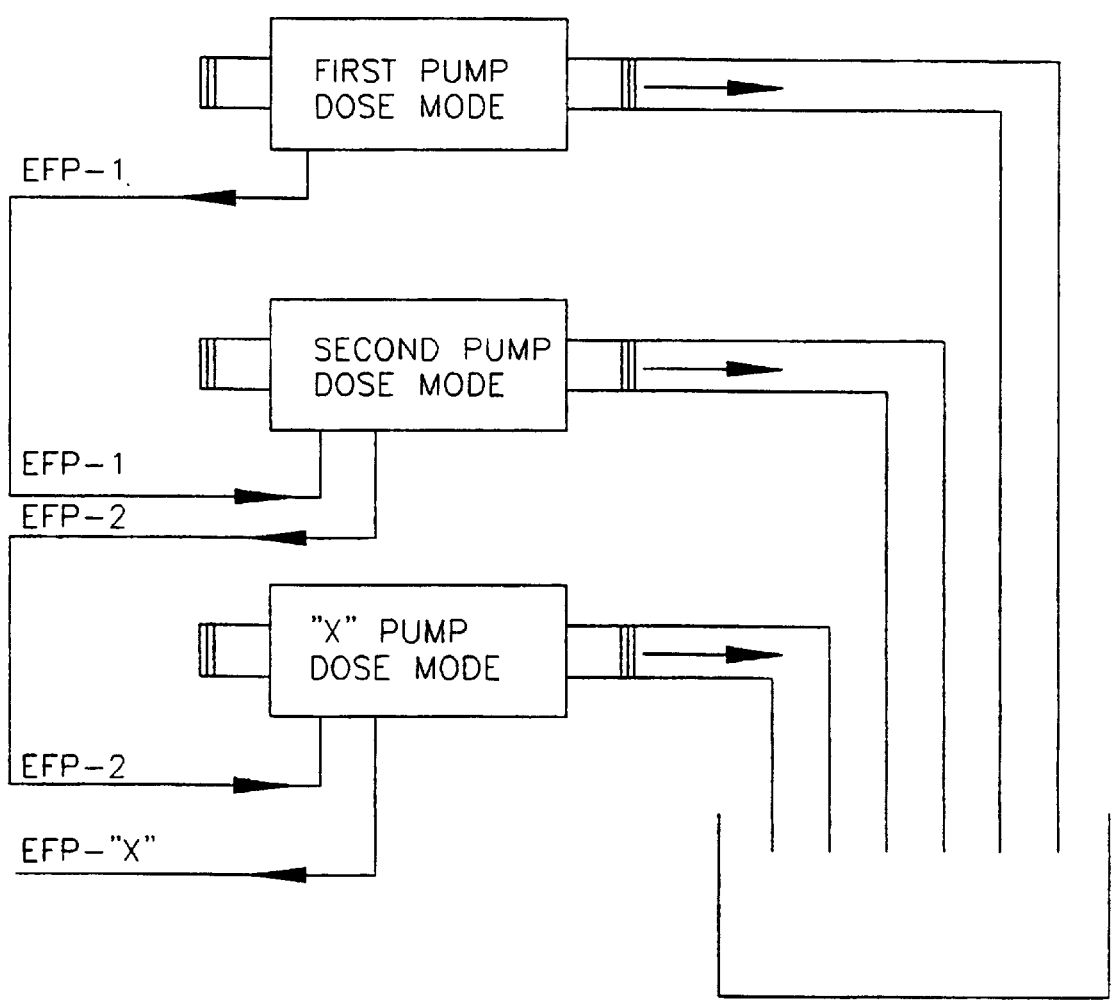
Figure 30:
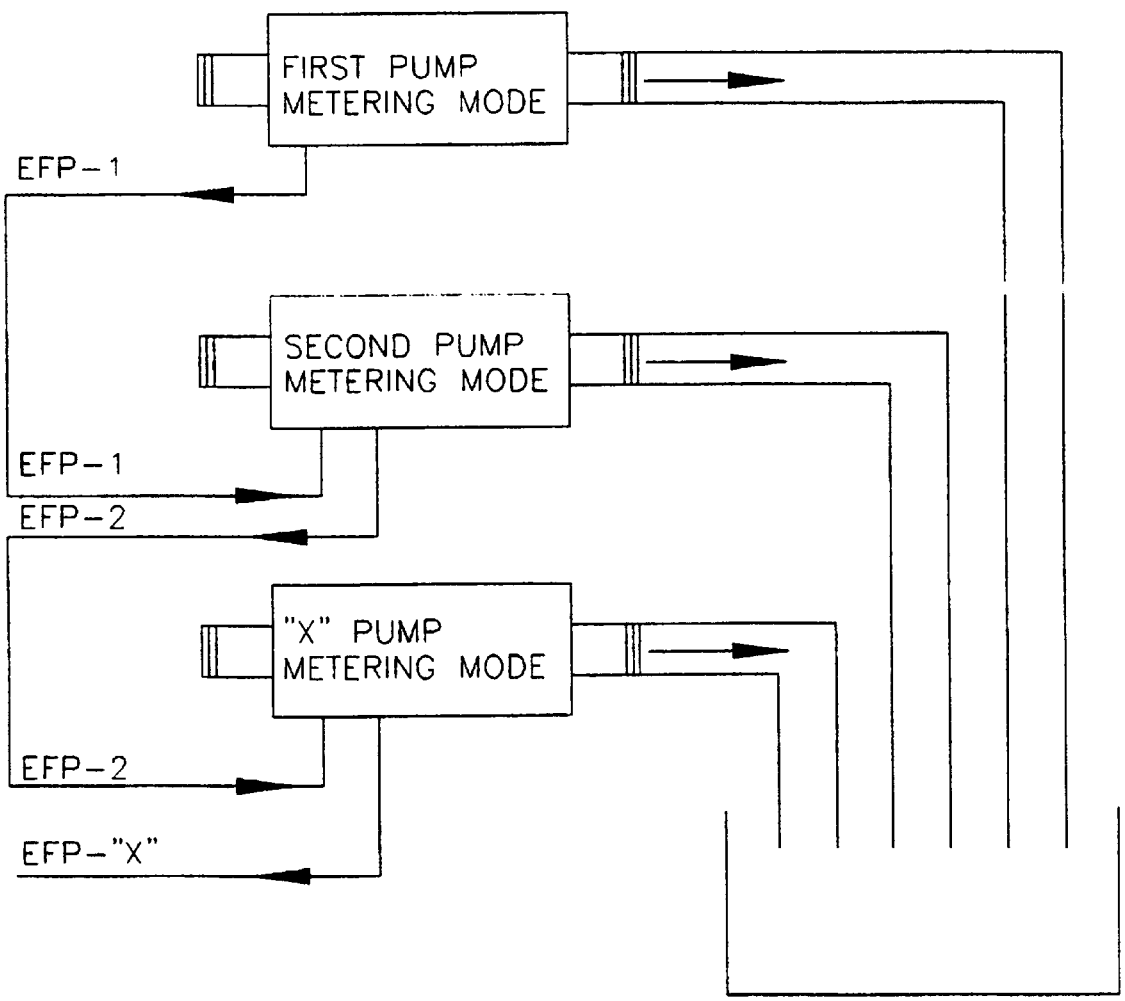

The first unique electronic control capability is the ability to simultaneously actuate two or more pumps of the present invention using a single initiation or start signal into a first pump. This allows the concurrent metering or dosing of one or more liquids which allows the batching or blending of liquids in any desired ratio or proportion, or the concurrent pump delivery of one or more liquids to the same location such as onto a common surface or into the same vessel or container. The electronic output firing pulse used to concurrently meter parallel flows from several pumps is configured as a signal which follows or mimics the start or run input status of the first pump. See FIGS. 27 and 28. The output firing signal of the first pump may be applied to the start or run input of each of the plurality of pumps (FIG. 27), or it may be applied to a second pump, and the output firing signal of the second pump can be applied to the start input of a third pump and so on in a cascading fashion (FIG. 28). When combined with the ability to readily adjust the flow rates of each pump in a plurality of pumps, this electronic control capability allows the simple and rapid configuration of metering, batching, and blending systems. The electronic output firing pulse, when used to concurrently dose from a plurality of pumps of the present invention, is configured in the same manner as for concurrent metering and may be distributed among the pumps in the same manner as well. See FIGS. 29 and 30. However, concurrent dosing may be arranged in two different ways. In one, the output firing pulse initiates a dose from each pump, FIG. 29, each dose volume being discretely electronically set in each pump controller as previously explained. Thus, while all dose cycles begin simultaneously, they may end at independently determined intervals. There are commonly encountered instances where it is desirable or necessary for a plurality of doses to begin and end simultaneously. Thus, the second arrangement of concurrent dosing allows the first pump to be operated in a dose mode, and the remainder of the plurality of pumps to be operated in the metering mode, as shown in FIG. 30. Because the electronic output firing pulse can be selected to be identical in duration to the start or run period of the first pump, the run period of all pumps matches the first pump. Because the volumetric flow rate of each pump when operating in the metering mode is adjustable, a desired dose may be established for each, and any such dose will match in duration the duration of the dose of the first pump.

Figure 31:
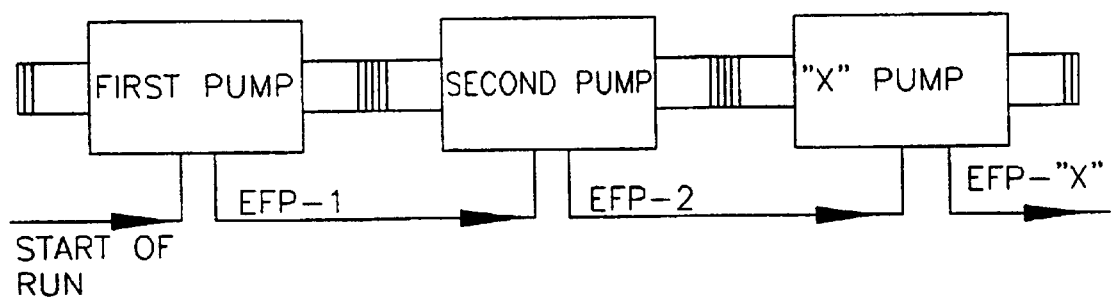
Figure 31A:
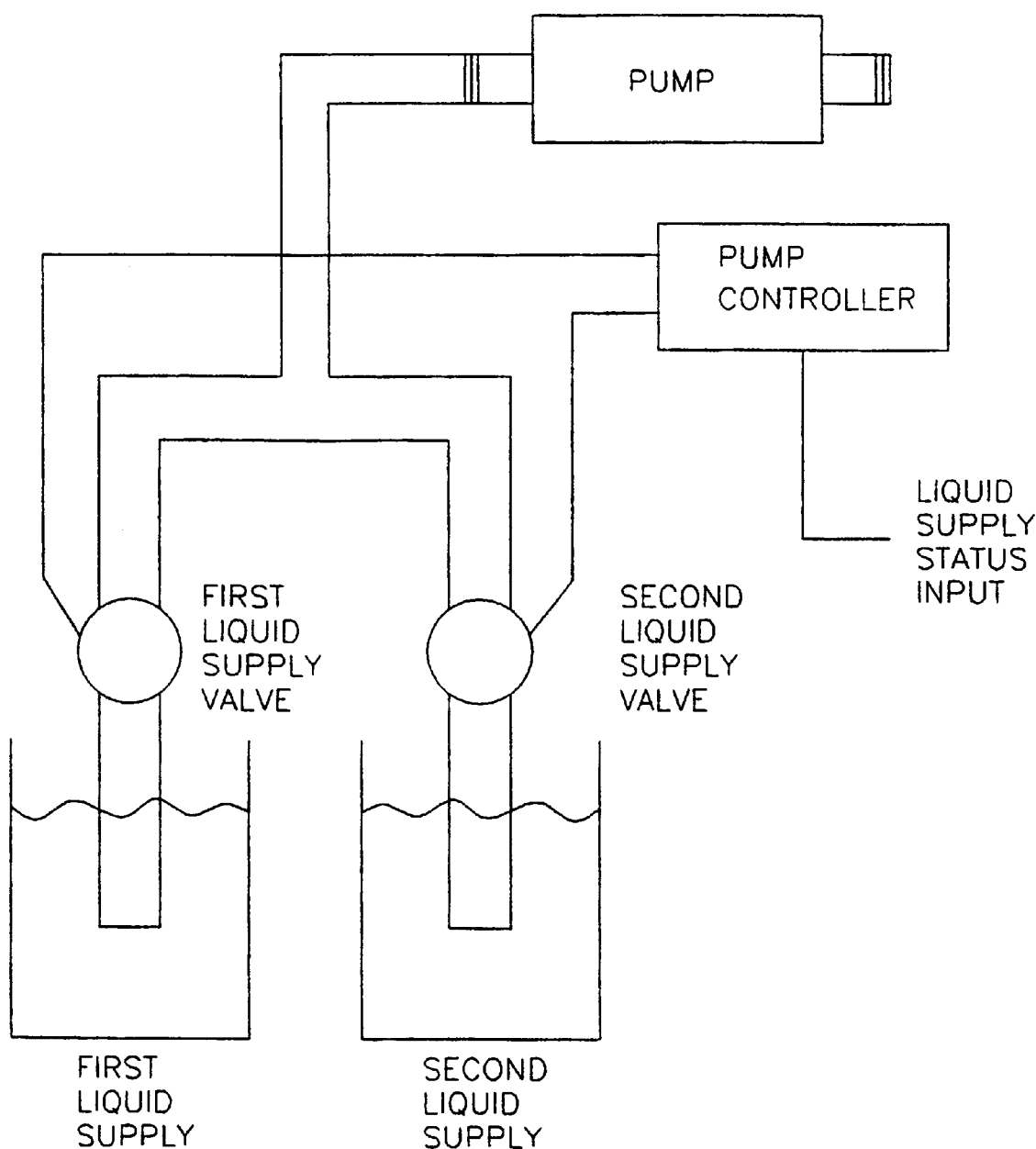
FIG. 31a illustrates multiple source of liquid supply being automatically connectable to the pump.
Figure 32:
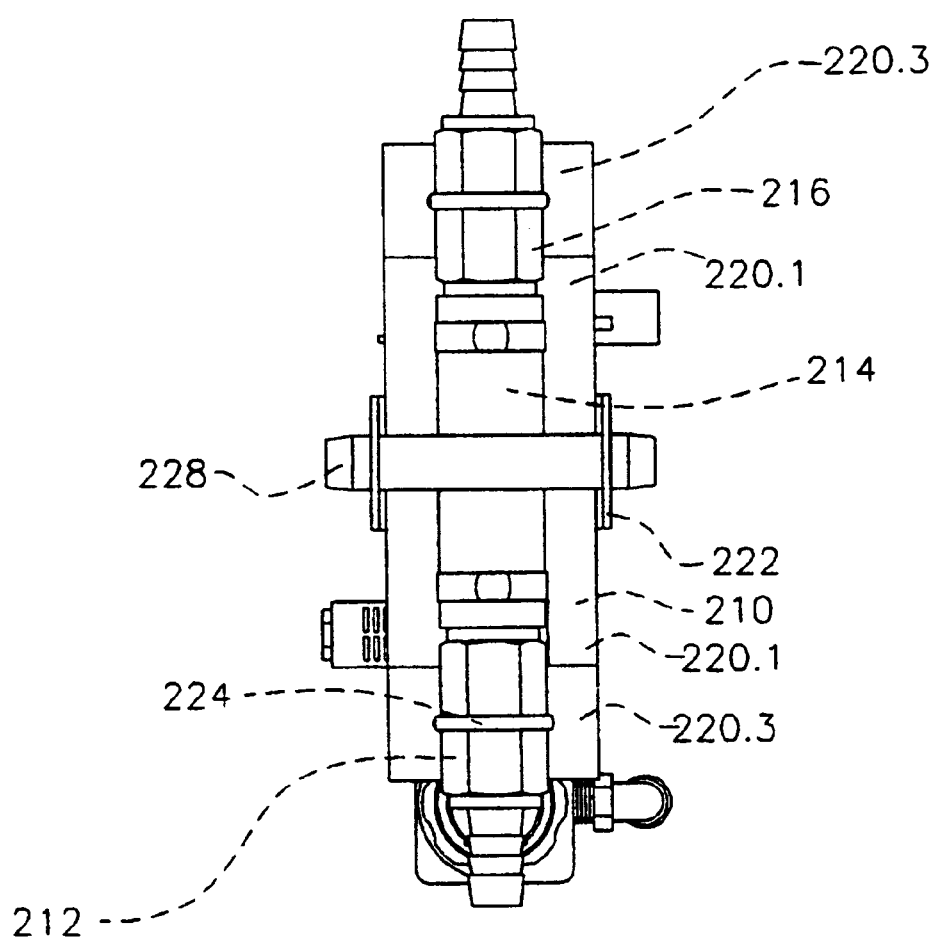
FIG. 32 is a front elevational view of a second embodiment of this invention.
Figure 33:
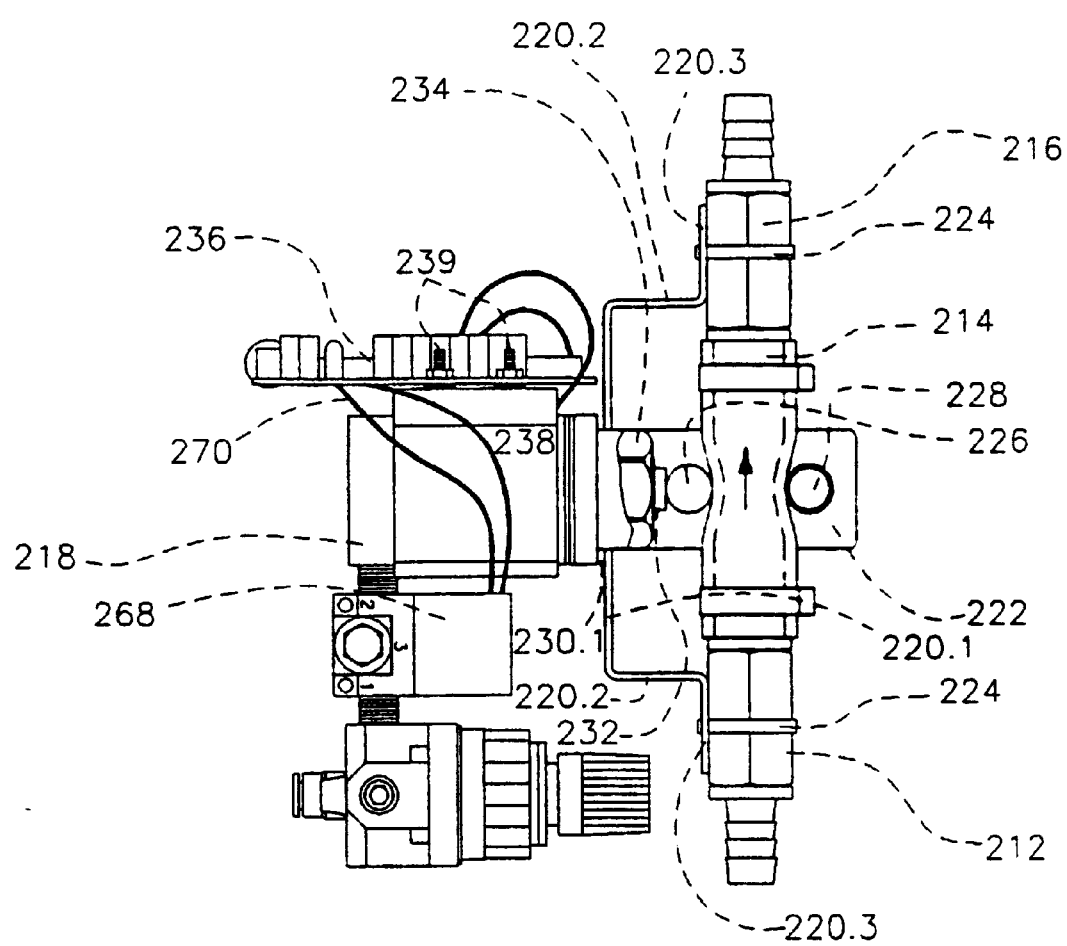
FIG. 33 is a side elevational view of the linear peristaltic pump apparatus shown in FIG. 32.

The second unique electronic control capability resulting from the novel design of a positionable electronic output firing signal is the ability to operate two or more pumps of the present arrangement in a series flow arrangement as shown in FIG. 31. It is a frequently encountered problem in pumping applications that a pump of particular size cannot provide a flow rate and/or pressure adequate to a particular requirement. A single larger pump is generally used to overcome this limitation rather than several pumps operating in series where the output flow of one pump serves as the infeed flow to another. This is because of the problems of control and coordination of operation of multiple pumps of known type. The electronic output firing signal provides a ready and simple solution to this control problem thus allowing multiple pumps of the present invention to operate in a series flow fashion thus allowing a more versatile and flexible solution to flow and pressure limitations than is the case with a single solution. This arrangement can be referred to as tandem pumping or as pressure boost pumping or as flow boost pumping.

The third unique electronic control capability made possible from the novel design of a positionable electronic output firing signal is the ability to electronically increase the pumping frequency of two or more pumps of the present invention operating in parallel in order to reduce the flow pulsations associated with the discharge of any single operating pump. Because the output firing signal can be positioned at any desired point in the pump sequence, two pumps can be operated with their sequences positioned, one relative to the other, to effectively double pumping frequency when their output flows are combined. Similarly, three pumps can be arranged to overlap their flows. In a typical operating environment, it can be shown empirically that when three or four pumps are operated in parallel with offset sequence timing, pulsating flow of the combined fluid outputs can be virtually eliminated. When operated in this manner, the positionable capability of the output is important. This is the case because establishing and maintaining the timing relationship between the plurality of pumps is crucial to the effect. In establishing this timing, typically a first pump is running in its metering (continuous pumping on demand) mode, while the second parallel flow pump is operating in its dosing mode with the dose set to one complete pump cycle. This arrangement allows the sequence initiation point of the second pump to be automatically or manually chosen and it ensures that the second pump remains synchronized to the first in the chosen manner in that each cycle of the first pump automatically re-establishes the pumping timing relationship with the second. If a third pump is added, it is set to operate in its dosing mode as the second, to a single cycle dose, and it is fired off of the electronic output firing signal of the second pump. The fourth is fired by the third, and so on.

Another unique feature of the control electronics of the pump of the present invention is the inclusion of presettable digital counters. These counters are incremented by a repeatable step in the pumping sequence and are primarily intended to allow the pump to provide self contained dose volumes(s) capability. Typically more than one counter 114 can be provided to allow the ability for the pump to deliver different dose volumes under different input commands. These counters may be pre-set using hard wired binary-coded decimal input devices, external pre-set commands, or display driven inputs to the microcontroller.

Another novel feature of the control electronics of the pump of the present invention is the provision for multiple start inputs 116. Multiple start inputs allow the pump to be operated by signals from several discrete locations. This capability can be useful when the pump is in the metering mode and is used in a complex flow system. However, multiple start inputs are especially beneficial when the pump is used in its dosing mode. When programmed for dosing, each start input can key a separate pre-set digital counter. This allows different dose volumes to be programmed into the pump controller and initiated by using a particular start input. The start inputs are particularly and uniquely designed to operate on a break before make basis. Thus, a valid or true input must become invalid or untrue before it can again become true. This is important, for example, in the case where an input initiates a dose. The dose self completes and the input cannot initiate a subsequent dose until it changes state. Another unique aspect of the start inputs is that the first valid start input of a plurality of such possible inputs locks out all other inputs until the valid input changes state.

Another unique feature of the control electronics of the pump of the present invention is the inclusion of presettable digital counters 118 expressly for the purpose of counting reverse pumping cycles. Although asymmetrical in terms of actuator size in some embodiments, the pump of the present invention is inherently flow direction reversible in all of its embodiments. This reversibility, which is instantaneously achievable at the completion of any given pumping cycle, is especially useful in dosing applications where it is frequently necessary to get a repeatable and orderly end of flow at the point of dispense of the dose. This need for a clean flow cut-off can frequently be achieved by reversing the pump at the end of a dose cycle and reversing flow. This is sometimes referred to as pull back or pump back or suck back. Whatever the term utilized, the use of reverse pumping counters in the design of the pump controller allows this function to be implemented in a defined and repeatable manner. Because of its intended use, each reverse pumping cycle counter is associated with a dose volume counter.

Another novel feature of the control electronics of the pump of the present invention is the provision of drivers 120 for initiating drive signals for positive shut-off valve at the point of outfeed flow termination or at the point of dispense. It is frequently necessary in both metering and dosing applications to create a clean and orderly termination of pump induced flow at some location remote from the pump. The use of a point of dispense valve allows this to occur. By providing a valve drive signal which directly tracks the on condition of the pump, system layouts are simplified, and accuracy and repeatability of the flow or dose is assured. It is important to note that each point of dispense valve drive signal is associated with a particular dose counter (if used) and a particular start input. Thus, as a control system, the electronics design allows start inputs at different locations to address different flow terminal locations.

Another unique feature of the electronic controller of the pump of the present invention is the provision for an input signal at terminal 122 which indicates to the microcontroller that the supply of liquid to the pump is low or exhausted. This signal is, in turn, used to inhibit the pump from further operation upon the completion of any in-progress pump cycle, and to drive an alarm output. Annunciation of the fault in the controller display, where fitted, is also provided for. This liquid supply input status capability is particularly important when the pump is used in critical metering or dosing applications.

The liquid supply input status capability may also be novelly used to drive output signals which can be utilized to shift valves to re-connect the pump infeed to an alternative source of liquid. Two such outputs are typically provided for, allowing the infeed to be shifted between two liquid supply sources. When this design feature is utilized, the liquid source presently connected to the pump infeed is indicated or displayed, and the connection is maintained as non-volatile data to allow power up and power down of the system without loss of connection status. This capability may be referred to as automatic liquid supply changeover.

Still another novel element of the design of the electronic controller of the pump of the present invention is the provision whereby the pumping sequence begins and ends with the actuators in precisely the same position, such position being determined by the electronic sequencing format designed into the controller in the first instance, and by the mechanical design in the second instance. This is an important improvement over prior art designs where the pump elements are actuated by means of a rotary cam assembly. In these designs, a reference means is typically provided and positioning relies upon a motor rotating the cam assembly until the reference is found. This method is vulnerable to error and failure. The novel method herein described is inherently digital, both on the electronic level as well as on the mechanical level. Electronically, by placing the drive signal to each actuator in a known state at the end of a pump cycle, typically low, the directed position of each element is absolutely determined. This is the case since when each actuator element is not driven it is essentially a digital device with only one stable or preferred position and that position is, in each case a mechanically determined and defined stop. In embodiments of the pump where the actuators are provided with position encoding sensors, the microcontroller can directly detect the actuator positions as a third level of verification.

Still another novel design aspect of the electronic controls of the pump, and a corollary to the known start and stop position feature, is the provision to assure that no partial pump cycles are allowed. Guaranteed cycle completion is achieved by a hardware or software requirement that no new start input is allowed until the last cycle step in the pump sequence (typically the opening of the IFV) has been achieved, and by the provision that once the pump cycle is initiated by a valid start input, the loss of the start input cannot stop or interrupt the completion of the sequence.

Still another unique aspect of the design of the electronic controller of the pump of the present invention is the provision for simplified interface to other forms of automation and control electronics. The pump of the present invention is designed for embodiment and use across the broad range of commercial and industrial applications. In these settings, electronic controls are frequently implemented using industrial versions of the personal computer (PC) or numerous versions of the programmable logic controller (PLC). The most common forms of inputs and outputs (I/O) to these devices are well known and typically consist of simple digital (on/off) formats. To simplify the interface of the pump to these control devices, the pump provides a group of automation I/O (FIG. 26). These include the pump start inputs already described, a control stop input allowing an overriding stop signal which can stop or inhibit the pump at the completion of any pumping cycle, and a run/count signal which allows external verification of pump status. The run/count signal is formatted to briefly change state at the end of each pump cycle. This allows pump cycles to be counted externally from terminal 126 for dosing or batching or data keeping applications. A fault signal output is also provided as well as a maintenance output.

Another novel provision of the electronic controller of the pump of the present invention, when the pump actuators are not encoded, is the ability to incrementally alter the IFV open time between a standard setting for operation with thin liquids and a viscous setting for thicker liquids via jumper 108. Similarly, the OFV close time may be progressively altered between a short distance (low back pressure) setting and a long distance (high back pressure) setting via jumper 106. These adjustments extend the range of capability of the pump in instances where the use of encoded actuators is not economically feasible.

Another novel provision of the electronic controller of the pump of the present invention is the diagnostics outputs provided as part of the design. Diagnostic information can be provided by simple serial coded output, or by discrete output positions. Diagnostic information includes excess back pressure (previously explained in reference to encoded actuators), loss or source change of liquid supply, on line (operable) or off line (inoperable) status of the pump, a dedicated cycle count output for external maintenance record keeping, and maintenance interval signal based upon internal record keeping. An example of internal maintenance record keeping would include a non-volatile internal counter in the microcontroller which accumulates cycle counts and annunciates a requirement to check the pump flow tube at specified intervals.

FIFTEENTH NOVEL FEATURE

The fifteenth novel feature of the three element linear peristaltic pump of the present invention concerns the ability of the pump to be adjusted to operate over a relatively broad range of actuator forces or pressures.

It is important to understand that in the linear peristaltic pumps of the previous art, where pneumatic or other linear actuators have been used, the use of open loop sequence timing where the true position of each of the actuator elements is unknown has been the practice. This makes the ability of these known pumps to operate over a broad range of adjustable actuator force largely unworkable. This is true because the correct motion and sequence relationship of each element to the other elements is necessary to produce pumping action.

When actuator forces change, as with an adjustment to reduced pneumatic pressure in the preferred embodiments of the present invention, the motion and timing relationships of the actuator devices change because of this force reduction. But if the electronically determined actuation times do not change, pump function is eventually lost beyond a limited range of pressure adjustment. Only with laborious and complete re-adjustment of the actuation times can correct pump function be established or restored at any given actuator pressure or force. This re-adjustment can be particularly difficult in prior designs in the art because there is no ready means to adjust each element in such a way as to observe or sense when a correct timing has been established for each sequential pump element.

With this as background, it is clear that the novel peristaltic pump of the present invention, when preferably equipped with sensors encoding for end of stroke or travel of each actuator, makes automatic timing sequence change as a function of adjustment in actuator pressure or force uniquely possible without any manual re-calibration or adjustment of the pumping sequence. This is the case since changes in actuation times are automatically accommodated because the required starting and ending positions of each actuator in the pumping sequence is known and each must be completed before the next can begin. Thus, correct sequential actuation function and pumping action is always maintained until the available actuator force is inadequate to effect complete actuator travel motion. The failure of any actuator to complete its travel in an allotted maximum time can be uniquely sensed and alarmed by virtue of the encoding method herein disclosed. Note that as the gas pressure applied to the actuators is reduced, the operating pressure capability of the pump is also reduced. The converse is also true. This is a useful and desirable characteristic in many pumping applications where the maximum allowable pressure which a pump can generate must be known and adjustable. Variations or fluctuations in back pressure can cause the flow rate of the pump to fluctuate. The means by which these externally generated pressure changes are dealt with are extensively discussed and disclosed in the sections of this patent application describing the encoded actuators and the electronic controls of the device.

Under some circumstances it is uniquely possible to maintain the encoded IFV and OFV actuators at a higher pressure to maintain high pressure valve action and separately supply the encoded pump displacement section actuator with variable pressure. This has the effect of maintaining the pumps differential pressure capability at a relatively high pressure while providing means to adjust and limit pumping pressure, but with a significant increase in cost and complexity.

SIXTEENTH NOVEL FEATURE

The sixteenth unique advantage of the three element linear peristaltic pump of the present invention is its ability to pump highly particulate, or non-homogeneous liquids and slurries.

Many liquids are heterogeneous in nature. These liquids are handled effectively by this design because the dual symmetrical anvil design serves to provide an efficient mechanism to move solids away from the occlusion contact areas of the pump elements. As a result, large solids are not trapped at the seal points of the pump elements and effective pumping is possible and large inclusions are essentially undamaged.

By way of example and illustration of the ability of the design to pump liquids with large inclusions, a pump of the present invention fitted with a flow tube with an internal diameter of 0.625 inches is able to pump a food preparation known as a Picante sauce. The sauce is tomato based and contains large irregularly shaped soft vegetable inclusions. A version of this sauce known as Pace Thick and Chunky Picante Sauce, manufactured by Pace Foods, Ltd. of San Antonio, Tex., contains vegetable chunks exceeding 0.375 inches in diameter and 0.750 inches in length. The pump is able to displace this liquid food product without measurable degradation or size reduction to the entrained solids. The liquid product described can be pumped without clogging or plugging or blockage of any kind within the pump.

It can be empirically demonstrated that the pump of the present invention can displace irregular soft inclusions in a liquid where such inclusions are sixty percent of the internal diameter of the flow tube. It can also be shown that hard irregular solids can typically be pumped when they do not exceed fifty percent of the internal diameter of the pump flow tube.

SEVENTEENTH NOVEL FEATURE

The seventeenth unique feature of the three element linear peristaltic pump of the present invention concerns its gas pumping capability.

It will be understood that when the displacement actuator compresses the liquid filled pump flow tube, a high pressure discharge flow is possible because liquids are relatively incompressible. Thus, even though the displacement actuator does not reduce the displacement lumen to a zero volume condition, the operation of the pump, when pumping liquids, is unimpaired.

However, because the displacement lumen of the pump of the present invention is not completely reduced to zero volume during displacement compression, this being true by the unique nature of the design, when the pump displaces a gas, the gas cannot become highly compressed and therefore cannot be pumped against or into high discharge pressures. This inability of the pump of the present design to displace gas at the relatively high pressures which can be developed with liquids provides a unique and valuable characteristic. In instances where liquid is being pumped and a gas embolism of a volume substantially equal to or greater than the uncompressed displacement lumen volume enters the displacement lumen, the pump essentially stops pumping. This is the case because the gas cannot leave the pump until it can be displaced from the pump and it cannot be displaced until the pressure at the discharge of the pump has decayed or reduced below the gas pressure the pump can generate. This characteristic is valuable in that large gas inclusions entrained in a liquid are not readily displaced by the pump. This is frequently a desirable condition in that in many applications gas entering a process can alter desired effects or reactions or cause inaccuracies of metering or dose. This characteristic is further advantageous in that in many instances it is inherently detectable within the pump. This is the case because the displacement actuator compression time can be measured by the pump control electronics and the sudden reduction in the actuator travel time resultant from a gas inclusion can be detected.

It is possible to increase the discharge gas pressure pumping capability of the pump by utilizing displacement anvils of larger size thus causing a greater part of the lumen to be collapsed with compression. However, if actuator force capability is held constant, the pump's liquid pumping pressure capability is reduced as anvil area is increased. This is a direct consequence of the relationship previously described relative to the force multiplication design. Thus, if a higher gas pumping pressure capability is desired without a loss of liquid pumping pressure capability, displacement anvil area must be increased and actuator force capability must be proportionately increased.

Another benefit of the characteristics exhibited by the pump of the present invention when pumping a gas embolism is the behavior of such a gas inclusion when it is pumped to atmosphere. It can be shown that in positive displacement diaphragm pumps where the displacement lumen is completely collapsed with each pump cycle, gas is displaced at comparatively high pressure and when such gas passes through a previously liquid filled tube attached to the discharge of the pump such that it is ultimately discharged to atmosphere, an explosive decompression effect is created. This decompression is violent and causes a wide dispersal of the liquid with which the pump discharge tube was previously filled. This can be inconvenient or even dangerous to people in the vicinity. It can be shown that with the pump of the present invention operating in an otherwise identical manner and configuration, no such explosive decompression occurs when gas is displaced to atmosphere.

SECOND EMBODIMENT

Figure 34:
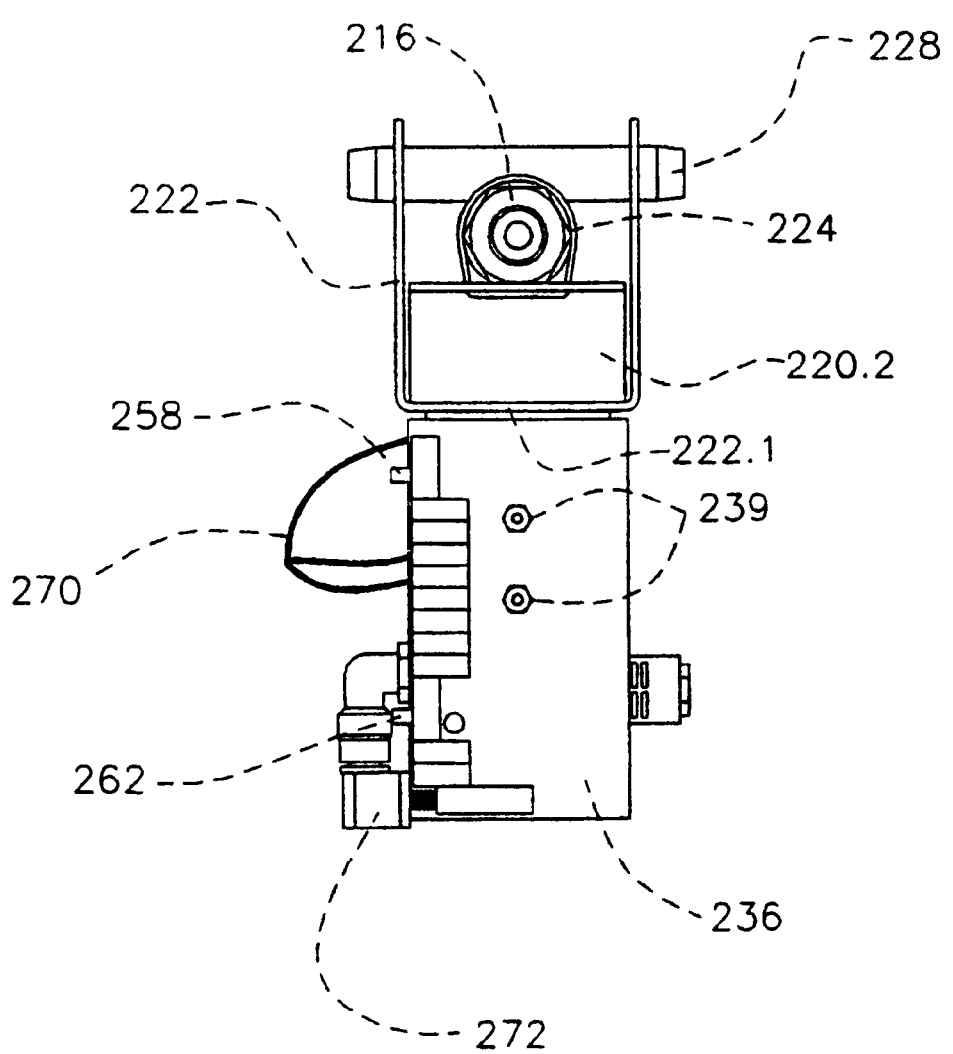
FIG. 34 is a top view of the pump apparatus shown in FIGS. 32 and 33.
Figure 35:
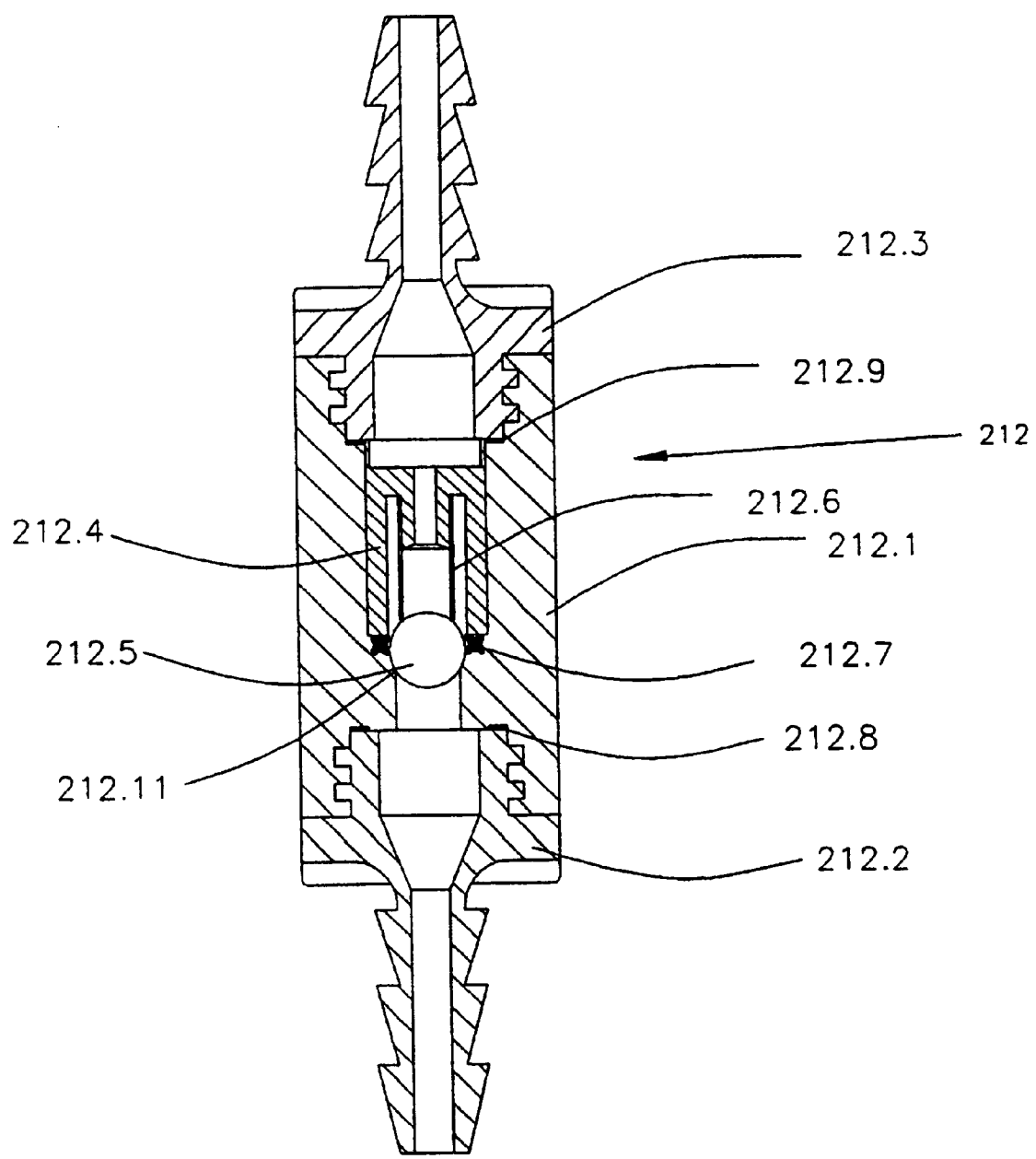
FIG. 35 is a sectional view of a check valve which is used in lieu of the occlusive valves of the first embodiment.

The second embodiment of the linear peristaltic pump apparatus of this invention, which is shown in FIGS. 32–35, uses check valves 212 and 216 instead of the occlusive valves of the first embodiment, and is modified in other ways. The second embodiment is more fully described in applicants copending U.S. provisional patent application Ser. No. 60/040,232, filed Mar. 11, 1997, the subject matter of which is incorporated herein by reference thereto. Briefly, the check valve pump apparatus consists of a suitable infeed check valve assembly 212 connected to one end of a short section of high durometer flexible tubing 214 of the same type employed above, with an outfeed check valve assembly 216 connected to the other end. The check valves, which allow fluid flow in only one direction, are fitted such that both allow flow in the same direction. Disposed between the two check valves is a pneumatically operated displacement assembly 218. Each of the valves 212 and 216 are essentially identical and a cross section of valve 212 is shown in FIG. 35. As can be seen from an inspection of this cross section, the valve consists of a valve body 212.1, infeed and outfeed barbs 212.2 and 212.3 which are screwed into the valve body 212.1. A cartridge 212.4 is disposed within the valve body 212.1. The valve body is provided with a seat 212.11 and when the parts are assembled, a ball 212.5 will be caused to bear against the seat 212.11 by a pressure spring 212.6. This spring is so selective that its cracking pressure will be 0.33 psi. In addition to the foregoing components, an annular seal 212.7 of the illustrated cross section is provided, the seal being positioned adjacent the seat 212.11 and in contact with the ball (when in its closed position) and the cartridge 212.4. O-ring seals 212.8 and 212.9 are also provided. The various components are made of suitable materials for use in a sanitary environment.

In the check valve pump shown in FIGS. 32–35, the pump frame, which supports the dual check valves 212 and 216, the flexible hose 214, and the compression element 218 used to cyclically compress the pump hose, is constructed using stainless steel sheet. The frame uniquely consists of only two parts, a check valve mount plate 220.1–220.3 and an upper anvil mount plate 222. The valve mount plate consists of a flat intermediate section 220.1 generally spanning the length of the flow tube. At each end of the flat section 220.1, the plate turns at 90 degrees and an extension section 220.2 extends toward each check valve. After an interval, the plate 220 again turns 90 degrees away from the center line of the pump. The result of this shape is to create a platform 220.3 at each end of the valve mount plate upon which the check valves rest and to which they are affixed. The check valves 212 and 216 can be fastened to their respective platforms by many means, but in the preferred embodiment a simple plastic cable tie 224 is used. To this end, two holes (not shown) are provided on each valve platform 220.3 suitably spaced apart to allow the cable tie 224 to pass around the valve and through the platform. Thus fastened, the pump tube is assured of being centered on compression anvils 226, 228 at right angles to the flow axis of the pump, compression anvil 226 being carried by the displacement assembly 218 and the other anvil being carried by the mounting plate 222. As best shown in FIG. 34, the upper anvil mount 222 is a U-shaped piece having a bight portion 222.1 which spans across the flat bottom section of the valve mount plate at 90 degrees to the long axis of the pump and is located at the center line of the anvil-actuator assembly. The upper anvil mount is located against the bottom surface of the valve mount plate such that it is captured between the shoulder 230.1 of the actuating pneumatic cylinder 230 and the valve mount plate. The result of this arrangement is the creation of a very stiff and strong anvil mount. The two frame pieces are assembled together using the threaded nose piece 232 and nut 234 of the actuating air cylinder. This single fastener uniquely serves to assemble the entire pump frame and actuator assembly.

The spaced apart sides 222.2 of the U-shaped upper anvil mount are each provided with hole, (no number) on each side, suitably spaced to allow insertion of the compression anvil 228 which is in the shape of a round rod, typically made of stainless steel. The anvil 228, when inserted, serves to capture and pre-compress the pump flow tube 214. The overall geometry and function of the compression anvils 226, 228 and the pneumatic actuator assembly 218 are analogous to that described for the displacement section of the three element pump described above, and will thus not be discussed herein.

The dual check valve pump of the present invention is novel in that the pneumatically operated cylinder displacement assembly 218 is provided to act directly upon the flexible and compressive pump tube in order to effect compression of the tube and hence liquid displacement. Pumps of the prior art disclose circumferential gas and hydraulic enclosures surrounding the pump tube, motor coupled linkage driven compression assemblies, and solenoid driven compressive elements, but fail to disclose direct compression of a dual check valve pump using a pneumatic cylinder assembly.

The means of pumping of the dual check valve pump 210 of the present invention is straight forward. The pneumatic air cylinder actuator 218, acting upon the flexible pump tube 214, serves to compress the tube, to variable degree as determined by the control electronics, thus causing the infeed check valve 212 to be reverse flow pressurized, and causing the outfeed check valve 216 to be forced open. When the pneumatic cylinder is depressurized, the stiff walled pump tube 214 forces it to reverse direction and the pump tube rebounds to a more open or uncompressed condition. This opening creates a lumen or volume greater than that at compression, thus causing the infeed check valve to be opened to flow due to the differential pressure created between the lumen (low) and the liquid in the infeed tubing (high) as acted upon by atmospheric pressure. (The terms "low" and "high" are relative to each other).

In its simplest embodiment, a control circuit card 236 is provided to be mounted directly onto the pump actuator by use of a suitable bracket or clip 238 which is secured to the card by suitable fasteners 239. In its simplest embodiment, the control card consists of an AC to DC power supply circuit, a timer circuit for actuator compression, a timer circuit for actuator retraction, a power-on initialization circuit, a run input buffer circuit, an on demand mode driver, an adjustable dose timer circuit, a pump valve driver, and a point of dispense valve driver.

In operation, a power switch 258 mounted on the circuit card 236 applies power to the circuit. The power-on initialization circuit assures that functions are properly initialized and also forces the pump actuator compression timer to fire, which, in turn, forces the pump actuator retract timer to fire. The retract timer then again fires the compression timer such that a self gated flip-flop or oscillator is established. Each timer period is separately established to achieve the desired pump function. An on card LED 260 is driven by the compression timer and provides a power on indicator and oscillator function indicator combined into the same device. Another circuit card mounted switch 262 allows selection between an on demand mode of operation and a timed dose mode of operation.

By omission of the infeed valve (IFV) and outfeed valve (OFV) control functions and capabilities dependent thereon, the novel capabilities and features embodied in the control electronics of the three element pump are directly applicable to the dual check valve pump particular to this application. These capabilities include the use of a microcontroller integrated circuit as the primary control engine, means of establishing metered flow, means of establishing dose volume, the provision for an electronic output firing signal, the use of presettable digital counters, the provision for multiple start inputs, the provision for a no liquid supply input signal to the pump with an associated pump inhibit and alarm output capability, the provision for automatic liquid supply changeover capability, and the provision for a run/count output signal.

While the best modes of this invention known to applicant at this time has been shown in the accompanying drawings and described in the accompanying text, along with variations of the illustrated best modes, it should be understood that applicant does not intend to be limited to the particular details illustrated in the accompanying drawings and described above. Thus, it is the desire of the inventors of the present invention that it be clearly understood that the embodiments of the invention, while preferred, can be readily changed and altered by one skilled in the art and that these embodiments are not to be limiting or constraining on the form or benefits of the invention. In the following claims references, such as "top" are for descriptive purposes only, and should not be considered limiting. Similarly the word housing should be interpreted broadly to include any suitable mounting structure.

What is claimed is:

1. A linear peristaltic pump apparatus for pumping liquids comprising:

a pump housing (22);

a high durometer compressible elastomeric liquid flow tube (12) carried by the housing (22);

an infeed valve assembly (26);

an outfeed valve assembly (38);

a discrete extensible and retractable displacement actuating assembly (36) including a movable actuator anvil (34) having a round surface which engages the flow tube (12) at all times;

a spaced apart top anvil (24.1) mounted in a location directly opposite from the actuator anvil (34), the top anvil (24.1) having a round surface in engagement with the flow tube at all times, the flow tube being held between the movable actuating anvil and the top anvil in a slightly compressed state when the actuating assembly is retracted, and the lumen of the flow tube not being completely reduced to zero volume during displacement compression whereby gas embolisms do not erupt or explode when discharged; and control means (100) for sequentially extending and retracting the actuating assembly (36) to cause flow within the flow tube (12) from a location adjacent the infeed valve assembly (26) to a location adjacent the outfeed valve assembly (38).

2. The linear peristaltic pump apparatus as set forth in claim 1 wherein the infeed valve assembly (26) and the outfeed valve assembly (38) are discrete infeed and outfeed extensible and retractable actuating assemblies, each including a movable actuator anvil (34) having a round surface which engages the flow tube (12) at all times, each of the infeed and outfeed valve assemblies further including a spaced apart top anvil (24.1) mounted in a location directly opposite from the associated actuator anvil (34), each of the top anvils (24.1) having a round surface in engagement with the flow tube at all times, the flow tube being held between the movable actuating anvils (34) and the top anvils (24.1) in a slightly compressed state when the actuating assemblies are retracted.

3. A linear peristaltic pump apparatus for pumping liquids comprising:

a pump housing (22);

a high durometer compressible elastomeric liquid flow tube (12) carried by the housing (22);

at least three discrete extensible and retractable actuating assemblies carried by the housing, including one occlusive infeed valve actuator assembly (26), one or more displacement actuator assemblies (36), and one occlusive outfeed valve actuator assembly (38), each actuating assembly including a movable actuator anvil (34) having a round surface which engages the flow tube (12) at all times;

spaced apart top anvils (24.1), each mounted in a location directly opposite from the corresponding actuator anvil (34) and having a round surface in engagement with the flow tube at all times, the flow tube being held between the movable actuator anvils and the top anvils in a slightly compressed state when the actuating assemblies are retracted; and control means (100) for sequentially extending and retracting the actuating assemblies (26, 36, 38) to cause flow within the flow tube (12) from a location adjacent the infeed valve actuator assembly (26) to a location adjacent the outfeed valve actuator assembly (38), whereby the apparatus can pump highly particulated or non-homogeneous liquids and slurries effectively because of the dual symmetrical anvil design which serves to provide an efficient mechanism to move solids sway from the occlusion contact areas of the pump elements such that large solids are not trapped at the occlusion points of the pump elements and the large inclusions pass through the pump essential undamaged.

4. The linear peristaltic pump apparatus as set forth in claim 3 wherein each of the actuators is a linear actuator.

5. A linear peristaltic pump apparatus for pumping liquids comprising:

a rigid generally channel shaped pump housing (22);

a high durometer compressible elastomeric liquid flow tube (12) mounted within the channel shaped pump housing (22);

at least three discrete extensible and retractable actuating assemblies carried by the housing, including one occlusive infeed valve actuator assembly (26), one or more displacement actuator assemblies (36), and one occlusive outfeed valve actuator assembly (38), each actuating assembly including a linear actuator and a movable actuator anvil (34) having a round surface which engages the flow tube (12);

a cover plate (24) provided with spaced apart round shaped top anvils (24.1) such that when assembled to the housing (22) each top anvil (24.1) is in a location directly opposite from a corresponding actuator anvil (34);

cover plate mounting means (50) for assembling the cover plate (24) to the housing (22) with the top anvils (24.1) bearing against the flow tube (12) in such a manner that the flow tube is slightly compressed; and control means (100) for sequentially extending and retracting the actuating assemblies (26, 36, 38) in such a manner as to cause flow within the flow tube (12) from a location adjacent the infeed valve actuator assembly (26) to a location adjacent the outfeed valve actuator assembly (38).

6. The linear peristaltic pump apparatus as set forth in any one of claims 1, 3, or 5 wherein the pump housing (22) has spaced apart sides (22.2, 22.3), the distance between the sides being adequate to assure no contact between the flow tube (12) and sides (22.2, 22.3) when the flow tube (112) is fully compressed to occlusion.

7. The linear peristaltic pump apparatus as set forth in any one of claims 1, 3, or 5 wherein the liquid flow tube (12) consists of a thick walled, multi-layer, laminated, compound reinforced, high pressure rated construction.

8. The linear peristaltic pump apparatus as set forth in any on of claims 1, 3, or 5 wherein the flow tube (12) is fitted with pressure rings (52) such that they contain the tube that they surround, thus limiting pressure mediated radial distension or swelling of the pump tube during high pressure pumping, such enhanced containment advantageously increasing the volumetric displacement of the pump with each complete pumping sequence.

9. The linear peristaltic pump apparatus as set forth in any one of claims 1, 3, or 5 wherein the pump housing is U-shaped.

10. The linear peristaltic pump apparatus as set forth in any one of claims 1, 3, or 5 wherein the round surface of each of the actuator anvils (34) has the same effective diameter as each of the round shaped top anvils (24.1).

11. The linear peristaltic pump apparatus as set forth in any one of claims 1, 3, or 5 wherein each actuator assembly includes a pneumatic cylinder (28).

12. The linear peristaltic pump as set forth in claim 11 wherein each pneumatic cylinder assembly has a pneumatic port (29) for receiving compressed gas, and further characterized by the provision of an electrically operated pneumatic solenoid valve (30, 60) closely coupled to the pneumatic port for the purpose of reducing the volume of compressed gas required to operate each actuator, thus increasing actuator speed and pump speed, reducing gas consumption required to operate the pump assembly and allowing the use of smaller pneumatic solenoid valves.

13. The linear peristaltic pump apparatus as set forth in claim 11 further characterized by the provision of a regulator (33) to vary the pressure to the actuators, whereby the cycle time may be varied.

14. The linear peristaltic pump apparatus as set forth in any one of claims 1, 3, or 5 further characterized by the provision of an external flow meter capable of measuring the displacement of the pump apparatus.

15. The linear peristaltic pump apparatus as set forth in either claim 3 or 5 wherein the occlusive infeed valve actuator assembly (26) is capable of applying more force than either the occlusive outfeed valve actuator assembly (38) or the one or more displacement actuator assemblies (36) to allow the pump apparatus to operate at relatively higher pumping pressure than can be achieved with all actuating assemblies having the same force capability.

16. The linear peristaltic pump apparatus as set forth in either claim 3 or 5 wherein each actuator assembly includes a pneumatic cylinder assembly, the diameter of the piston within the pneumatic cylinder assembly of the occlusive infeed valve actuator assembly being greater than the diameter of the pistons within the other pneumatic cylinder assemblies, whereby a constant force ratio is established between the occlusive infeed valve assembly and the other actuating assemblies when the same pressure is applied to each pneumatic cylinder assembly.

17. The linear peristaltic pump apparatus as set forth in either claim 3 or 5 wherein each of the actuator anvils (34) is formed of bar stock, circular in cross section.

18. The linear peristaltic pump apparatus as set forth in either claim 3 or 5 wherein each of the actuators is a pneumatic cylinder assembly having a cylinder (28) and an operating rod (32) extending out of the cylinder, each of the actuator anvils (34) being mounted on an end of an operating rod remote from the associated cylinder, wherein the cover plate is a serpentine rigid sheet stock element, wherein the housing has spaced apart apertured side walls, and wherein the cover plate mounting means is a plurality of pull pins (50), one for each of the top anvils, the pull pins passing through the apertures in the side walls, each pull pin (50) being located at the center of a force line applied by each actuating assembly along the centerline of the operating rod thus creating an extremely rigid assembly capable of withstanding very high compressive forces.

19. The linear peristaltic pump apparatus as set forth in either claim 3 or 5 wherein each of the actuators is a pneumatic cylinder assembly having a cylinder (28) provided with a movable piston, an operating rod (32) extending out of the cylinder, each of the actuator anvils (34) being mounted on an end of an operating rod remote from the associated piston, the area of each of the pistons being greater than the area of the each of the actuator anvils which contact the flow tube during occlusion to achieve force multiplication, and wherein the flow tube (12) is fitted with pressure rings (52) such that they contain the tube that they surround, thus allowing high rebound forces to be generated by the pump tube after compression, these high rebound forces generating a high suction priming force adequate to overcome the high flow resistance and suction drag associated with priming viscous liquids.

20. The linear peristaltic pump apparatus as set forth in either claim 4 or 5 wherein each of the linear actuators is a pneumatic cylinder assembly, further characterized by the provision of a linear incremental encoder (58) fitted to at least one of the displacement actuator assemblies, wherein the control means (100) includes a microcontroller (102), and wherein the control means may operate the pump in a metering mode of a given flow rate per minute in response to signals received by the microcontroller from the linear encoder.

21. The linear peristaltic pump apparatus as set forth in either claim 4 or 5 wherein each of the linear actuators is a pneumatic cylinder assembly, further characterized by the provision of a linear incremental encoder (58) and end of travel encoders (35.1, 35.2) fitted to at least one of the pneumatic cylinder assemblies, and wherein the control means (100) includes a microcontroller (102), the control means being capable of operating the pump apparatus in a dose mode wherein a defined volume of liquid is pumped with a high degree of repeatability.

22. The linear peristaltic pump apparatus as set forth in claim 21 wherein the linear incremental encoder is mounted on the pneumatic cylinder assembly for a displacement actuator assembly, and the end of travel encoders are mounted on the pneumatic cylinder assemblies for the infeed and outfeed valve actuator assemblies.

23. The linear peristaltic pump apparatus as set forth in either claim 4 or 5 wherein each of the linear actuators is a pneumatic cylinder assembly having a cylinder (28) and an operating rod (32) extending out of the cylinder, each of the actuator anvils (34) being mounted on an end of an operating rod remote from the associated cylinder.

24. The linear peristaltic pump apparatus as set forth in claim 23 wherein the of the pump housing has spaced apart sides (22.2, 22.3), wherein each of the actuator anvils (34) is formed of bar stock, circular in cross section and having a length slightly less than the distance between the sides, the spaced apart sides (22.2, 22.3) preventing rotation of the anvils (34) about the operating rods (32).

25. The linear peristaltic pump apparatus as set forth in claim 23 wherein a piston is mounted in each of the cylinders, the area of each of the pistons being greater than the area of the each of the actuator anvils which contact the flow tube during occlusion to achieve force multiplication.

26. The linear peristaltic pump apparatus as set forth in claim 23 wherein a piston is mounted in each of the cylinders, the maximum stroke of the piston being greater than the movement required to occlude the flow tube.

27. The linear peristaltic pump apparatus as set forth in claim 23 wherein the rebound or opening force of the pump tube is sufficient to return each operating rod to its retracted position, even when a vacuum is being applied to the inlet end of the pump tube.

28. The linear peristaltic pump apparatus as set forth in claim 23 further characterized by the provision of a mechanical stroke limiting stop (59) to limit return movement of the actuator anvil, thereby reducing to some desired degree the volume displacement capability of the pump.

29. The linear peristaltic pump apparatus as set forth in claim 23 further characterized by the provision of a pressure supply valve (60) and an exhaust valve (62) associated with each of the one or more displacement actuator assemblies, each of the supply valves and exhaust valves being a 2-way normally closed solenoid valve, and further characterized by the control means including timer means, whereby the pressure supply valve is opened for a defined time as determined by the pump electronic controller, and then closed, this resulting in movement of the pump displacement actuator over a defined distance, the actuator remaining at some intermediate displaced distance of extension for a holding time during which time the outfeed valve is closed completing a displacement cycle of the pump in which a reduced volumetric displacement is achieved, and whereafter the pressure exhaust valve is opened, allowing the displacement actuator to return to its fully open position; and wherein this method of flow rate control is easily varied and linearized electronically and is repeatable and operable over a broad range of flow within the capability of the pump and where the flow rate is stable over extended periods of time and the pressure and viscosity capabilities of the pump are preserved; and wherein as flow rate is reduced, pump cycle frequency increases of may be electronically adjusted to be held steady at the full displacement cycle rate.

30. The linear peristaltic pump apparatus as set forth in claim 29 further characterized by the provision of full open and full closed encoding sensors (35.1, 35.2) mounted on the actuating assemblies for detecting the end of stroke of each actuating element, whereby the start is marked by the change in state of the full open sensor (35.1) signal thus allowing actual actuator motion to be determined, thus further improving the precision of this method of pump flow rate control.

31. The linear peristaltic pump apparatus as set forth in claim 29 further characterized by the provision of a linear incremental encoder (58) fitted to the pneumatic cylinder assembly to precisely define its desired displacement motion, thus providing a closed loop control of said motion to any intermediate location and thereby further improving the pump flow rate accuracy and stability of the method; and wherein the use of an incremental encoder on the pump displacement actuator assures that the movement of the actuator continues until a prescribed position is reached regardless of any change in actuator velocity or force as a function of any external influence.

32. The linear peristaltic pump apparatus as set forth in claim 23 further characterized by the provision of a pressure supply valve (60) and an exhaust valve (62) associated with each of the one or more displacement actuator assemblies, each of the supply valves and exhaust valves being a 2-way normally closed solenoid valve, and further characterized by the displacement actuator including encoder means whereby the pressure supply valve is opened to allow movement of the pump displacement actuator to a defined location.

33. The linear peristaltic pump apparatus as set forth in claim 5 wherein the pump housing (22) has spaced apart sides (22.2, 22.3), the distance between the sides being adequate to assure no contact between the flow tube (12) and sides (22.2, 22.3) when the flow tube (12) is fully compressed to occlusion, and wherein the round surface of each of the actuator anvils (34) has the same effective diameter as each of the round shaped top anvils (24.1).

34. The linear peristaltic pump apparatus as set forth in claim 33 wherein the liquid flow tube (12) consists of a thick walled, multi-layer, laminated, compound reinforced, high pressure rated construction to allow relatively high pump feed and discharge pressures to be contained by the tube with minimal distortion, swelling or bulging or stretching of the pump tube, thus allowing comparatively high pressure operation of the pump.

35. The linear peristaltic pump apparatus as set forth in any one of claims 5, 33, or 34 wherein the cover plate (24) is a serpentine rigid sheet stock element.

36. The linear peristaltic pump apparatus as set forth in claim 35 wherein the cover plate is symmetrical.

37. The linear peristaltic pump apparatus as set forth in 35 wherein a unitized spacer (23) consisting of a single serpentine shaped piece is overlaid onto the original cover plate (24) and then assembled to the pump body (22) utilizing the cover plate mounting means (50) so that the round shaped top anvils (24.1) are forced closer to the actuator anvils (34), thus establishing the desired and proper degree of symmetrical compression capture when a smaller diameter tube is used.

38. The linear peristaltic pump apparatus as set forth in claim 35 wherein the housing has spaced apart apertured side walls, and wherein the cover plate mounting means is a plurality of pull pins (50), one for each of the top anvils, the pull pins passing through the apertures in the side walls, the foregoing assuring a simple and self evident procedure for assembly.

39. The linear peristaltic pump apparatus as set forth in claim 38 wherein a spacer (50.1 or 50.2) is inserted about each of the pull pins (50) so that the round shaped top anvils (24.1) are forced closer to the actuator anvils (34), thus establishing the desired and proper degree of symmetrical compression capture when a smaller diameter flow tube (12) is used.

40. The linear peristaltic pump apparatus as set forth in claim 5 wherein the liquid flow tube (12) consists of a thick walled, multi-layer, laminated, compound reinforced, high pressure rated construction, wherein the pump housing (22) has spaced apart sides (22.2, 22.3), the distance between the sides being adequate to assure no contact between the flow tube (12) and sides (22.2, 22.3) when the flow tube (112) is fully compressed to occlusion, wherein the round surface of each of the actuator anvils (34) has the same effective diameter as each of the round shaped top anvils (24.1), and wherein a piston is mounted in each of the cylinders, the area of each of the pistons being greater than the area of the each of the actuator anvils which contact the flow tube during occlusion, the foregoing allowing long term pump tube operating fatigue phenomenon such as progressive reduction in suction or priming capability or discharge pressure capability as the tube wears fatigues or compression sets to be nearly completely avoided.

41. The linear peristaltic pump apparatus as set forth in claim 5 wherein the housing has inlet and outlet end plates (40, 42), and wherein the flow tube (12) has a length just slightly less than the distance between the end plates.

42. The linear peristaltic pump apparatus as set forth in claim 41 wherein the inlet and outlet end plates are provided with slots (40.1, 42.1), and further characterized by the provision of pump hose fittings (14, 18) mounted within opposed ends of the flow tube (12), the pump hose fittings being captured by the slots in the end plates.

43. The linear peristaltic pump apparatus as set forth in claim 42 wherein the cover plate is provided with locking tongues (24.2, 24.3) for locking into position the pump hose fittings at each end of the flow tube (12).

44. The linear peristaltic pump apparatus as set forth in claim 5 further characterized by the provision of pump hose fittings (14, 18) mounted within opposed ends of the flow tube (12), each of the hose fittings having an internal shank with an end that terminates within the flow tube, the distance (dd) between the end of the internal shank of the hose fitting and the center line of its respective anvil pair being within the range of 1.20 to 2.0 times the internal diameter of the pump hose, this arrangement causing a faster restoration of the compressed pump hose when the adjacent actuating assembly is retracted.

45. The linear peristaltic pump apparatus as set forth in any one of claims 1, 3, or 5 wherein the control means can be selected to operate in one of the two primary liquid flow operating modes, the first mode being termed metering mode and the second being termed dosing mode; wherein the metering mode allows the pump to establish and maintain a defined volumetric flow rate, and wherein the dosing mode allows the pump to deliver a defined volume of liquid with a high degree of repeatability.

46. The linear peristaltic pump apparatus as set forth in claim 45 wherein the control means (100) includes a variable potentiometer (110) which may be used to adjust the last pump cycle when volumetrically dosing.

47. The linear peristaltic pump apparatus as set forth in any one of claims 1, 3, or 5 wherein the control means includes a microcontroller (102), and further characterized by the provision of an external flow meter (128), the output of which is interconnected with the microcontroller in order to control the flow output from the pump.

48. The linear peristaltic pump apparatus as set forth in any one of claims 1, 3, or 5 wherein the control means (100) produces an electronic output firing pulse, which firing pulse is selected to initiate at any desired point in the pump sequence, and which pulse may be used to simultaneously actuate two or more similar pumps, thus allowing concurrent metering of one or more liquids which allows the batching or blending of liquids in any desired ratio or proportion, or allowing concurrent dosing or one or more liquids, or allowing cascaded dosing, or allowing two or more pumps of this invention to be operated in series as in pressure boost pumping, or in parallel with the outputs combined into a single flow and wherein the flow pulsations are progressively reduced.

49. The linear peristaltic pump apparatus as set forth in any one of claims 1, 3, or 5 wherein the control means (100) is provided with multiple presettable digital counters to allow the control means to provide self-contained dose volume capability where each counter can be set to a different count in order to provide different dose volumes under separate and discrete start inputs.

50. The linear peristaltic pump apparatus as set forth in claim 49 wherein at least on presettable digital counter is provided for the express purpose of counting reverse pumping cycles.

51. The linear peristaltic pump apparatus as set forth in either claim 1, 3, or 5 wherein the control means (100) is provided with multiple presettable digital counters and with multiple start inputs in order to allow it to be operated by signals from multiple discrete locations, wherein each start input can address a different preset digital counter.

52. The linear peristaltic pump as set forth in claim 51 in which the electronic controller is provided with valve driver outputs for initiating drive signals to remote shut-off valves at the point of pump output flow termination or at the point of dispense, said signals directly reflecting the on/off status of the pump.

53. The linear peristaltic pump as set forth in claim 52 wherein each valve driver output signal is associated with a particular dose counter and a particular start input, thus allowing start inputs at different locations to address different flow termination points.

54. The linear peristaltic pump apparatus as set forth in either claim 1, 3 or 5 wherein the control means includes a microcontroller (102) and an input signal terminal which can indicate to the microcontroller that the supply of liquid to the pump is low, and where the input signal can cause the controller to reconnect the pump to an alternate supply of liquid.

55. The linear peristaltic pump apparatus as set forth in either claim 1, 3 or 5 further characterized by the provision of start means associated with the control means, the control means assuring that no new start input is allowed until the last cycle step in the pump sequence is complete, and further assuring that once a pump cycle is initiated by a start input, the loss or change in state of the start input cannot stop or interrupt the completion of the pump sequence, and further assuring that a control stop input can be implemented only at the completion of the pump sequence.

56. The linear peristaltic pump apparatus as set forth in either claim 1, 3 or 5 wherein the control means includes a pump start input circuit, a control stop input circuit, a run/count output signal circuit which allows external verification of pump status and external counting of pump cycles, and a fault signal output.

57. The linear peristaltic pump apparatus as set forth in claim 1, 3 or 5 wherein the control means provides for diagnostic outputs which can be serially encoded or discrete, consisting of outputs for excess back pressure, excess system pressure, loss of liquid supply, operable or inoperable status, cycle count, and maintenance interval.

58. The linear peristaltic pump apparatus as set forth in either claim 1, 3 or 5 wherein a linear incremental encoder (58) is fitted to at least one of the displacement actuator assemblies, wherein the control means (100) includes a microcontroller (102), the control means being capable of making automatic sequence changes as a function of adjustment of actuator pressure or force without manual recalibration or alteration such that correct sequence motion relationship required among actuators for correct pumping action is maintained.

59. The linear peristaltic pump apparatus as set forth in either claim 1, 3 or 5 wherein the control means causes the infeed valve actuator assembly and all displacement actuator assemblies to be retracted to their unoccluded positions at the completion of operating cycles, thus greatly reducing the duration of occlusion and minimizing compression set and tube rebound fatigue.

60. The linear peristaltic pump apparatus as set forth in claim 59 wherein the control means is further provided with an alternative operating mode which will cause all actuator assemblies to be retracted when unrestricted flow through the flow tube (12) is desired.

61. The linear peristaltic pump apparatus as set forth in either claim 3 or 5 wherein the control means may control the infeed valve actuator assembly valve open time effectively increasing the priming time as a discrete and separately adjustable event in the pump cycle, thus allowing the priming lumen of the pump tube to completely fill with liquid, thus allowing the volumetric displacement of each pumping cycle to be maintained.

62. The linear peristaltic pump apparatus as set forth in either claim 3 or 5 wherein the control means may detect and signal when the infeed valve actuator assembly valve open time becomes longer in time than desired, thus constituting an end to effective useful pump tube life or pump tube fatigue.

63. The linear peristaltic pump apparatus as set forth in either claim 3 or 5 wherein the control means includes an internal timer, the open time of the infeed valve actuator assembly being adjusted by the timer to adjust the volumetric flow rate of a pump apparatus.

64. The linear peristaltic pump apparatus as set forth in either claim 3 or 5 wherein the control means functions to allow the flow rate of the pump to be controlled by electronically altering the timing and thus the motion relationship between the one or more displacement actuator assemblies and the outfeed valve actuator assembly to effect a change in displaced pump volume per cycle, such that after the one or more displacement actuator assemblies has compressed, and before the outfeed valve actuator assembly has occluded, the one or more displacement actuator assemblies is allowed to partially return to an open condition, a portion of the volume previously expelled thus being drawn back into the lumen of the flow tube, the outfeed valve actuator assembly then being closed to occlusion; wherein this method of flow rate adjustment is smoothly variable and repeatable and operable over a broad range of flow within the capability of the pump and where the discharge pressure capability of the pump is not impaired and the feed of liquid into the pump is not altered and the method is largely insensitive to variations in pump discharge pressure.

65. The linear peristaltic pump apparatus as set forth in either claim 3 or 5 wherein each of the control means will insure that all actuators begin and end the pumping sequence in the same position.

66. The linear peristaltic pump apparatus as set forth in either claim 3 or 5 wherein the control means may vary the open time of the occlusive infeed valve actuator assembly to permit operation with liquids of varying viscosities.

67. The linear peristaltic pump apparatus as set forth in either claim 3 or 5 wherein the control means may vary the close time of the occlusive outfeed valve actuator assembly to permit operation with a low back pressure setting and a high back pressure setting.

68. The linear peristaltic pump apparatus as set forth in either claim 3 or 5 having more than one displacement actuator assembly in order to increase the liquid flow rate per pump cycle without a reduction of pump discharge pressure capability and without a significant increase in pump cycle time.

69. The linear peristaltic pump as set forth in claim 68 wherein the displacement actuator assembly nearest the infeed valve actuator assembly can move a distance sufficient to occlude the flow tube (12), the other displacement actuator assemblies not being able to move a distance sufficient to occlude the flow tube thus allowing simultaneous compressive actuation of all displacement actuator assemblies in the pump apparatus without the possibility to trap or block the displaced flow of any of the displacement actuator assemblies.

70. The linear peristaltic pump as set forth in claim 68 wherein all of the displacement actuator assemblies are not able to move a distance sufficient to occlude the flow tube thus allowing simultaneous compressive actuation of all displacement actuator assemblies in the pump apparatus without the possibility to trap or block the displaced flow of any of the displacement actuator assemblies.

71. The linear peristaltic pump apparatus as set forth in claim 68 wherein all displacement actuator assemblies are the same, whereby the displacement of the pump is altered by the addition of displacement actuator assemblies in a known and predictable manner and with no change in the pumps discharge pressure capability.

72. The linear peristaltic pump apparatus as set forth in claim 68 wherein the control means (100) is operated such that the displacement actuator assembly furthest from the occlusive outfeed valve actuator assembly is actuated first, with a time delay being imposed between this first displacement actuator assembly and the actuation of the next adjacent displacement actuator assembly, said delay being electronically determined by pump control electronics and of a duration less than the displacement actuator assembly occlusion travel time, and the same delay being interposed before the actuation of each successive displacement actuator assembly, such that each displacement actuator assembly closer to the occlusive outfeed valve actuator assembly cannot occlude ahead of the displacement actuator assembly immediately preceding it, thus assuring that no displaced flow can be cut off prior to sequential compression by each displacement actuator assembly.

73. The linear peristaltic pump apparatus as set forth in claim 68 wherein the control means (100) includes a microcontroller (102), the control means also including input means for inputting the number of displacement actuator assemblies in the pump apparatus or automatically detecting the number of displacement actuator assemblies, whereby the pump control sequence is altered to insert the required sequence actuation delay times.

74. The linear peristaltic pump apparatus as set forth in claim 73 wherein the input is automatic.

75. The linear peristaltic pump apparatus as set forth in claim 68 wherein each of the displacement actuator assemblies is provided with an end of travel sensor (35.1, 35.2).

76. The linear peristaltic pump assembly as set forth in claim 68 wherein the control means includes a microcontroller (102) and each of the actuators is provided with travel encoding sensors (35.1, 35.2) in such a way as to allow detection of the fully retracted and fully extended positions of each actuator element in the pump, such that the status of each encoding sensor is integrated into the microcontroller providing absolute and continuous control, diagnostics, and optimization of the pump apparatus.

77. The linear peristaltic pump assembly as set forth in claim 75 wherein the control means (100) senses the signals from the end of travel sensors to provide optimum adjustment, on a completely automatic basis, of the proper sequencing of multiple displacement actuator assemblies, such that the loss of signal from an open position end of travel sensor fitted to the displacement actuator assembly closest to the infeed valve actuator assembly causes the next displacement actuator assembly to begin motion, which, in turn, causes the next to sequence, thus allowing the time delay between actuations to be under directly sensed control and thus to be as minimal as possible.

78. The linear peristaltic pump apparatus as set forth in claim 68 wherein the control means (100) is operated to accommodate the pumping of large entrained solids within the flow tube by insuring that each displacement actuator assembly is allowed to complete pump tube occlusion before the next downstream displacement actuator assembly begins compressive movement, the sequence delay being established on a time basis in which case the delay is equal to or greater than the compress to occlusion time of the displacement actuator assemblies.

* * * * *